(12) United States Patent
Siahaan et al.

(10) Patent No.: US 9,573,983 B2
(45) Date of Patent: Feb. 21, 2017

(54) COMPOSITIONS INCLUDING I-DOMAIN ANTIGEN CONJUGATE COMPOUNDS AND METHODS FOR TREATMENT OF AUTOIMMUNE DISORDERS

(71) Applicant: University of Kansas, Lawrence, KS (US)

(72) Inventors: Teruna J. Siahaan, Lawrence, KS (US); Prakash Manikwar, Lawrence, KS (US); Paul Kipkemboi Kiptoo, Lawrence, KS (US); Ahmed Badawi, Overland Park, KS (US); Barlas Buyuktimkin, Lawrence, KS (US); John M. Stewart, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 342 days.

(21) Appl. No.: 13/733,991

(22) Filed: Jan. 4, 2013

(65) Prior Publication Data
US 2013/0183327 A1 Jul. 18, 2013

Related U.S. Application Data

(60) Provisional application No. 61/583,736, filed on Jan. 6, 2012.

(51) Int. Cl.
*C07K 14/47* (2006.01)
*C07K 14/705* (2006.01)

(52) U.S. Cl.
CPC ..... *C07K 14/4713* (2013.01); *C07K 14/70553* (2013.01); *C07K 2319/00* (2013.01)

(58) Field of Classification Search
None
See application file for complete search history.

(56) References Cited

PUBLICATIONS

Shetty, A., et al. Neurol. Neuroimmunol. Neuroinflamm. 2014;1:1-11.*
Ransohoff, R.M. Trends in Immunol. 2006;27(4):167-168.*
Sriram, S. and Steiner, I. Ann. Neurol. 2005;58:939-945.*
Badawi AH, Kiptoo P, Wang WT, Choi IY, Lee P, Vines CM, Siahaan TJ. Suppression of EAE and prevention of blood-brain barrier breakdown after vaccination with novel bifunctional peptide inhibitor. Neuropharmacology. 2012; 62: 1874-1881.
Badawi AH, Siahaan TJ. Immune modulating peptides for the treatment and suppression of multiple sclerosis. Clin Immunol. 2012; 144: 127-138.
Bagert, B. A. Epstein-Barr virus in multiple sclerosis. Curr Neurol Neurosci Rep 9,405-410 (2009).
Barnes T, Moots R. Targeting nanomedicines in the treatment of rheumatoid arthritis: focus on certolizumab pegol. Int J Nanomedicine. 2007; 2: 3-7.
Blanchfield, J. L., and Mannie, M. D. (2010) A GMCSF-neuroantigen fusion protein is a potent tolerogen in experimental autoimmune encephalomyelitis (EAE) that is associated with efficient targeting of neuroantigen to APC. J. Leukoc. Biol. 87,509-521.
Brennan, R. M. et al. Strains of Epstein-Barr virus infecting multiple sclerosis patients. Mult Scler16, 643-651, doi:10.1177/1352458510364537 (2010).
Bruno, V., Battaglia, G. & Nicoletti, F. The advent of monoclonal antibodies in the treatment of chronic autoimmune diseases. Neurol Sci31 Suppl 3, 283-288, doi:10.1007/s10072-010-0382-6 (2011).
Buyuktimkin B, Wang Q, Kiptoo P, Stewart JM, Berkland C, Siahaan TJ. Vaccine-like controlled-release delivery of an immunomodulating peptide to treat experimental autoimmune encephalomyelitis. Mol Pharm. 2012; 9: 979-985.
Cadavid D, Wolansky LJ, Skurnick J, Lincoln J, Cheriyan J, Szczepanowski K, Kamin SS, Pachner AR, Helper J, Cook SD. Efficacy of treatment of MS with IFN beta-1b or glatiramer acetate by monthly brain MRI in the BECOME study. Neurology. 2009; 72: 1976-1983.
Caliceti P, Veronese FM. Pharmacokinetic and biodistribution properties of poly(ethylene glycol)-protein conjugates. Adv Drug Deliv Rev. 2003; 55: 1261-1277.
Carson, K. R., Focosi, D., Major, E. O., Petrini, M., Richey, E. A., West, D. P., and Bennett, C. L. (2009) Monoclonal antibody-associated progressive multifocal leucoencephalopathy in patients treated with rituximab, natalizumab, and efalizumab: a Review from the Research on Adverse Drug Events and Reports (RADAR) Project Lancet Oncol. 10, 816-824.
Ebers GC. Environmental factors and multiple sclerosis. Lancet Neurology. 2008; 7: 268-277.
El-behi, M., Rostami, A. & Ciric, B. Current views on the roles of Th1 and Th17 cells in experimental autoimmune encephalomyelitis. J Neuroimmune Pharmacol, 189-197, doi:10.1007/s11481-009-9188-9 (2010).
Falk, K., Rotzschke, O., Santambrogio, L., Dorf, M. E., Brosnan, C., and Strominger, J. L. (2000) Induction and suppression of an autoimmune disease by oligomerized T cell epitopes: enhanced in vivo potency of encephalitogenic peptides. J. Exp. Med. 191, 717-730.
Fletcher, J. M., Lalor, S. J., Sweeney, C. M., Tubridy, N. & Mills, K. H. T cells in multiple sclerosis and experimental autoimmune encephalomyelitis. Clin Exp Immunol, 1-11, doi:10.1111/j.1365-2249.2010.04143.x (2010).
Goodin DS, Cohen BA, O'Connor P, Kappos L, Stevens JC. Assessment: The use of natalizumab (Tysabri) for the treatment of multiple sclerosis (an evidence-based review)—Report of the therapeutics and technology assessment subcommittee of the American Academy of Neurology. Neurology. 2008; 71: 766-773.
Haak, S. et al. IL-17A and IL-17F do not contribute vitally to autoimmune neuro-inflammation in mice. J Clin Invest, 61-69, doi:10.1172/JCI35997 (2009).

(Continued)

*Primary Examiner* — Gerald R Ewoldt
(74) *Attorney, Agent, or Firm* — Thomas Horstemeyer, LLP

(57) ABSTRACT

The present disclosure provides IDAC compounds capable of presenting two or more signal 1 moieties to a host immune system and methods of using the IDAC compounds to treat or prevent autoimmune disorders in a subject. The present disclosure provides compounds including a modified I-domain peptide having two or more modified lysine residues and two or more signal 1 moieities conjugated to the modified lysine residues of the I-domain peptide and methods of using an making the compounds.

13 Claims, 53 Drawing Sheets

(56) References Cited

PUBLICATIONS

Haines JL, et al. A complete genomic screen for multiple sclerosis underscores a role for the major histocompatability complex. The Multiple Sclerosis Genetics Group. Nat Genet. 1996; 13: 469-471.

Higgins PJ, Weiner HL. Suppression of experimental autoimmune encephalomyelitis by oral administration of myelin basic protein and its fragments. J Immunol. 1988; 140: 440-445.

Ikehata, K., Duzhak, T. G., Galeva, N. A., Ji, T., Koen, Y. M., and Hanzlik, R. P. (2008) Protein targets of reactive metabolites of thiobenzamide in rat liver in vivo. Chem. Res. Toxicol. 21, 1432-1442.

Kappos L, Antel J, Comi G, Montalban X, O'Connor P, Polman CH, Haas T, Korn AA, Karlsson G, Radue EW. Oral fingolimod (FTY720) for relapsing multiple sclerosis. New Engl J Med. 2006; 355: 1124-1140.

Keller, A., Nesvizhskii, A. I., Kolker, E., and Aebersold, R. (2002) Empirical statistical model to estimate the accuracy of peptide identifications made by MS/MS and database search. Anal. Chem. 74, 5383-5392.

Kobayashi N, Kiptoo P, Kobayashi H, Ridwan R, Brocke S, Siahaan TJ. Prophylactic and therapeutic suppression of experimental autoimmune encephalomyelitis by a novel bifunctional peptide inhibitor. Clin Immunol. 2008; 129: 69-79.

Kobayashi, N., Kobayashi, H., Gu, L, Malefyt, T., and Siahaan, T. J. (2007) Antigen-specific suppression of experimental autoimmune encephalomyelitis by a novel bifunctional peptide inhibitor. J. Pharmacol. Exp. Ther. 322, 879-886.

Kress-Bennett JM, Ehrlich GD, Bruno A, Post JC, Hu FZ, Scott TF. Preliminary study: treatment with intramuscular interferon beta-1a results in increased levels of IL-12Rbeta2+ and decreased levels of IL23R+ CD4+ T- Lymphocytes in multiple sclerosis. BMC Neurol. 2011; 11: 155.

Larche, M. & Wraith, D. C. Peptide-based therapeutic vaccines for allergic and autoimmune diseases. Nat Med, S69-76, doi:10.1038/nm1226 (2005).

Lee, S. J. & Benveniste, E. N. Adhesion molecule expression and regulation on cells of the central nervous system. J Neuroimmunol98, 77-88 (1999).

Luca, M. E., Kel, J. M., van Rijs, W., Wouter Drijfhout, J., Koning, F., and Nagelkerken, L. (2005) Mannosylated PLP (139-151) induces peptide-specific tolerance to experimental autoimmune encephalomyelitis. J. Neuroimmunol. 160, 178-187.

Manikwar P, Buyuktimkin B, Kiptoo P, Badawi AH, Galeva NA, Williams TD, Siahaan TJ. I-domain-antigen conjugate (IDAC) for delivering antigenic peptides to APC: synthesis, characterization, and in vivo EAE suppression. Bioconjug Chem. 2012; 23: 509-517.

Manikwar, P. et al. Utilization of I-domain of LFA-1 to Target Drug and Marker Molecules to Leukocytes. Theranostics, 277-289 (2011).

Manikwar, P., Kiptoo, P., Badawi, A. H., Buyuktimkin, B. & Siahaan, T. J. Antigen-specific blocking of CD4-specific immunological synapse formation using BPI and current therapies for autoimmune diseases. Med Res Rev, doi:10.1002/med.20243 (2011).

Manikwar, P., Zimmerman, T., Blanco, F. J., Williams, T. D. & Siahaan, T. J. Rapid Identification of Fluorochrome Modification Sites in Proteins by LC ESI-Q-TOF Mass Spectrometry. Bioconjug Chem, 1330-1336, doi:10.1021/bc100560c (2011).

Marriott JJ, Miyasaki JM, Gronseth G, O'Connor PW. Evidence Report: The efficacy and safety of mitoxantrone (Novantrone) in the treatment of multiple sclerosis. Report of the Therapeutics and Technology Assessment Subcommittee of the American Academy of Neurology. Neurology. 2010; 74: 1463-1470.

Matsushita T, Yanaba K, Bouaziz JD, Fujimoto M, Tedder TF. Regulatory B cells inhibit EAE initiation in mice while other B cells promote disease progression. J Clin Invest. 2008; 118: 3420-3430.

McRae BL, Vanderlugt CL, Dal Canto MC, Miller SD. Functional evidence for epitope spreading in the relapsing pathology of experimental autoimmune encephalomyelitis. J Exp Med. 1995; 182: 75-85.

Mehvar R. Modulation of the pharmacokinetics and pharmacodynamics of proteins by polyethylene glycol conjugation. J Pharm Pharm Sci. 2000; 3: 125-136.

Meiron, M., Zohar, Y., Anunu, R., Wildbaum, G., and Karin, N. (2008) CXCL12 (SDF-1alpha) suppresses ongoing experimental autoimmune encephalomyelitis by selecting antigen-specific regulatory T cells. J. Exp. Med. 205, 2643-2655.

Mohr DC, Hart SL, Julian L, Cox D, Pelletier D. Association between stressful life events and exacerbation in multiple sclerosis: a meta analysis. British Medical Journal. 2004; 328: 731-736.

Monoclonal antibody-associated progressive multifocal leucoencephalopathy in patients treated with rituximab, natalizumab, and efalizumab: a Review from the Research on Adverse Drug Events and Reports (RADAR) Project. Lancet Oncol. 2009; 10: 816-824.

Muro, S., Gajewski, C., Koval, M. & Muzykantov, V. R. ICAM-1 recycling in endothelial cells: a novel pathway for sustained intracellular delivery and prolonged effects of drugs. Blood105, 650-658, doi:10.1182/blood-2004-05-1714 (2005).

Murray, J. S., Oney, S., Page, J. E., Kratochvil-Stava, A., Hu, Y., Makagiansar, I. T., Brown, J. C., Kobayashi, N., and Siahaan, T. J. (2007) Suppression of type 1 diabetes in NOD mice by bifunctional peptide inhibitor: modulation of the immunological synapse formation. Chem. Biol. Drug Des. 70, 227-236.

Ni, J., Zhu, Y. N., Zhong, X. G., Ding, Y., Hou, L. F., Tong, X. K., Tang, W., Ono, S., Yang, Y. F., and Zuo, J. P. (2009) The chemokine receptor antagonist, TAK-779, decreased experimental autoimmune encephalomyelitis by reducing inflammatory cell migration into the central nervous system, without affecting T cell function. Br. J. Pharmacol. 158, 2046-2056.

Pugashetti R, Koo J. Efalizumab discontinuation: a practical strategy. J Dermatolog Treat. 2009; 20: 132-136.

Ridwan R, Kiptoo P, Kobayashi N, Weir S, Hughes M, Williams T, Soegianto R, Siahaan TJ. Antigen-specific suppression of experimental autoimmune encephalomyelitis by a novel bifunctional peptide inhibitor: structure optimization and pharmacokinetics. J Pharmacol Exp Ther. 2010; 332: 1136-1145.

Salomon, B., and Bluestone, J. A. (1998) LFA-1 interaction with ICAM-1 and ICAM-2 regulates Th2 cytokine production. J. Immunol. 161, 5138-5142.

Schmidt S. Candidate autoantigens in multiple sclerosis. Multiple sclerosis. 1999; 5: 147-160.

Schwartz, R. H. (2003) T cell anergy. Annu. Rev. Immunol. 21, 305-334.

Seidel, M. F., Keck, R. & Vetter, H. ICAM-1/LFA-1 expression in acute osteodestructive joint lesions in collagen-induced arthritis in rats. J Histochem Cytochem, 1247-1253 (1997).

Serafini B, Severa M, Columba-Cabezas S, Rosicarelli B, Veroni C, Chiappetta G, Magliozzi R, Reynolds R, Coccia EM, Aloisi F. Epstein-Barr virus latent infection and BAFF expression in B cells in the multiple sclerosis brain: implications for viral persistence and intrathecal B-cell activation. J Neuropathol Exp Neurol. 2010; 69: 677-693.

Shimaoka, M., Xiao, T., Liu, J. H., Yang, Y., Dong, Y., Jun, C. D., McCormack, A., Zhang, R., Joachimiak, A., Takagi, J., Wang, J. H., and Springer, T. A. (2003) Structures of the alpha L I domain and its complex with ICAM-1 reveal a shape-shifting pathway for integrin regulation. Cell 112, 99-111.

Speicher, K., Kolbas, O., Harper, S., and Speicher, D. (2000) Systematic analysis of peptide recoveries from in-gel digestions for protein identifications in proteome studies. J. Biomol. Tech. 11, 74-86.

Stanley, P. & Hogg, N. The I domain of integrin LFA-1 interacts with ICAM-1 domain 1 at residue Glu-34 but not Gln-73. J Biol Chem273, 3358-3362 (1998).

Tan, C. S., and Koralnik, I. J. (2010) Progressive multifocal leukoencephalopathy and other disorders caused by JC virus: clinical features and pathogenesis. Lancet Neurol. 9, 425-437.

(56) References Cited

OTHER PUBLICATIONS

Wang, C., Gold, B. G., Kaler, L. J., Yu, X., Afentoulis, M. E., Burrows, G. G., Vandenbark, A. A., Bourdette, D. N., and Offner, H. (2006) Antigen-specific therapy promotes repair of myelin and axonal damage in established EAE. J. Neurochem. 98, 1817-1827.
Whitacre CC. Sex differences in autoimmune disease. Nat Immunol. 2001; 2: 777-780.
Wraith, D. C. Therapeutic peptide vaccines for treatment of autoimmune diseases. Immunol Lett122, 134-136, doi:10.1016/j.imlet.2008.11.013 (2009).
Zhao, H., Kiptoo, P., Williams, T. D., Siahaan, T. J., and Topp, E. M. (2010) Immune response to controlled release of immunomodulating peptides in a murine experimental autoimmune encephalomyelitis (EAE) model. J. Control Release 141, 145-152.
Annunziato, F., Cosmi, L. & Romagnani, S. Human and murine Th17. Curr Opin HIV AIDS5, 114-119, doi:10.1097/COH.0b013e32833647c2 (2010).
Arnon R. The development of Cop 1 (Copaxone®), and innovative drug for the treatment of multiple sclerosis personal reflections. Immunol Lett. 1996; 50: 1-15.
Ascherio, A. & Munger, K. L. Environmental risk factors for multiple sclerosis. Part I: the role of infection. Ann Neurol61, 288-299, doi:10.1002/ana.21117 (2007).
Ascherio, A. et al. Epstein-Barr virus antibodies and risk of multiple sclerosis: a prospective study. Jama286, 3083-3088 (2001).
Paslakis, et al.; The Putative Role of Human Peritoneal Adipocytes in the Fight against Bacteria: Synthesis of the Antimicrobial Active Peptide DEFA1-3; Nephron Exp Nephrol 2010;115:e96-e100.

\* cited by examiner

HSLGKWLGHPDKFC = SEQ ID NO: 2

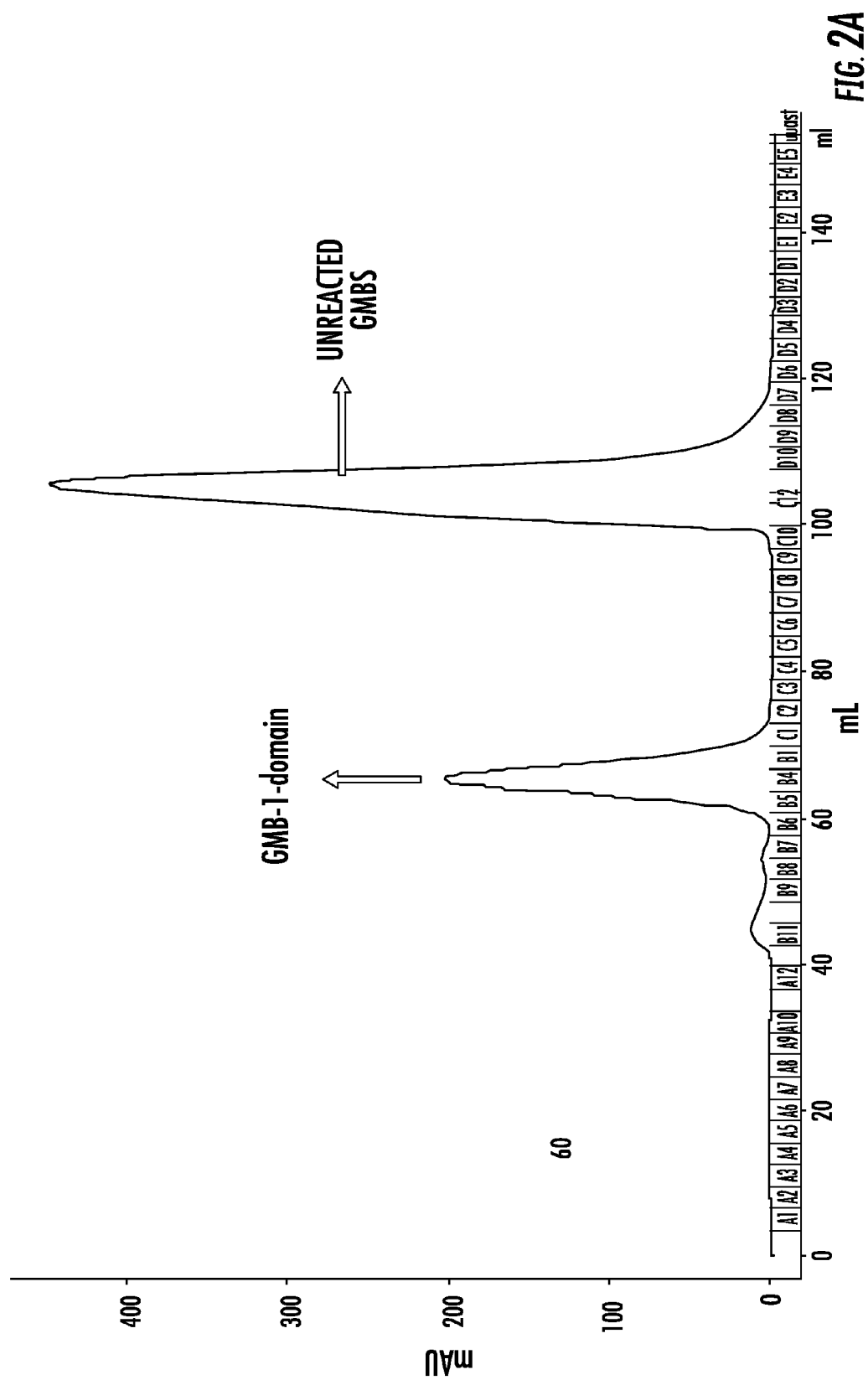

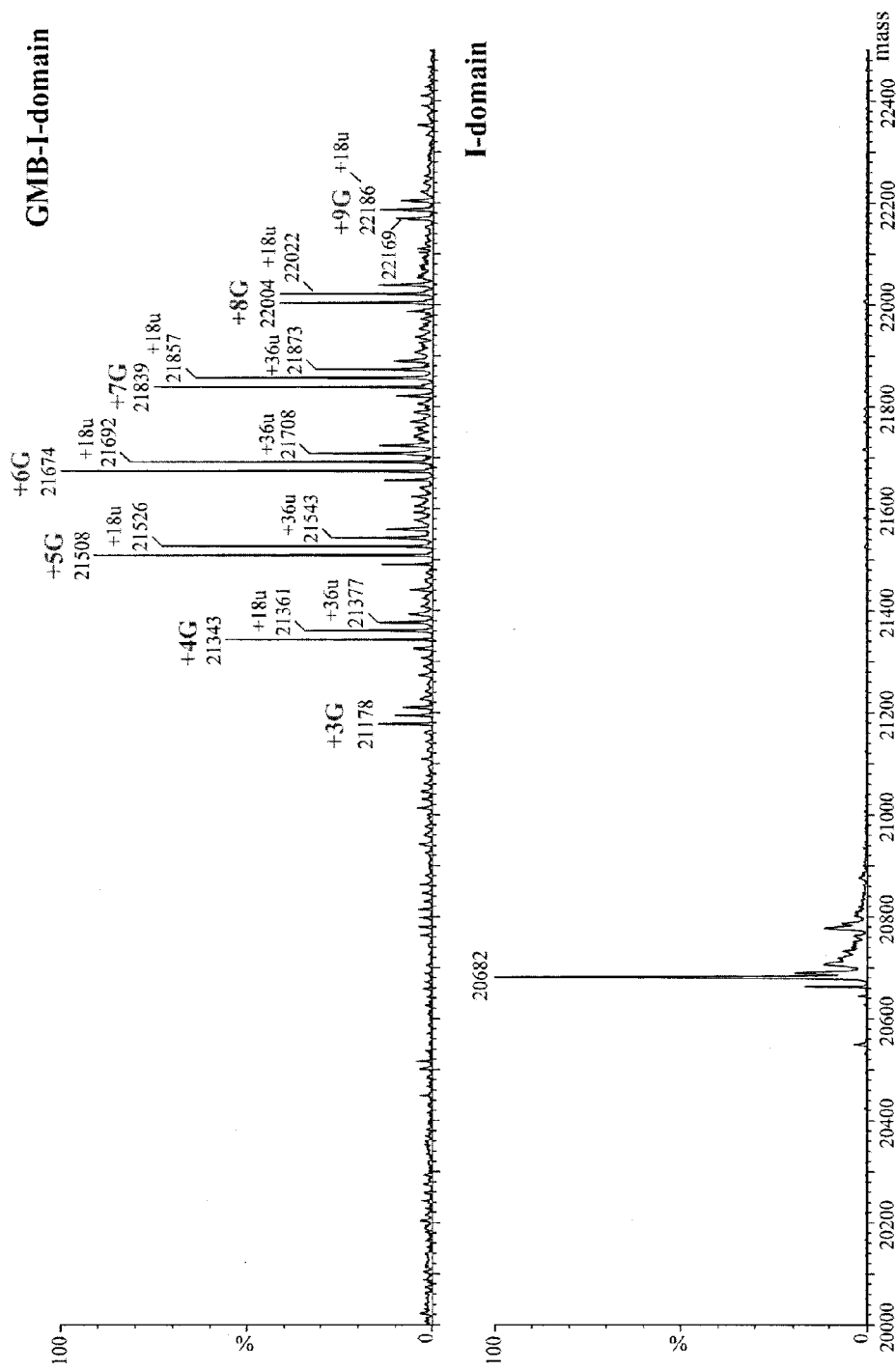

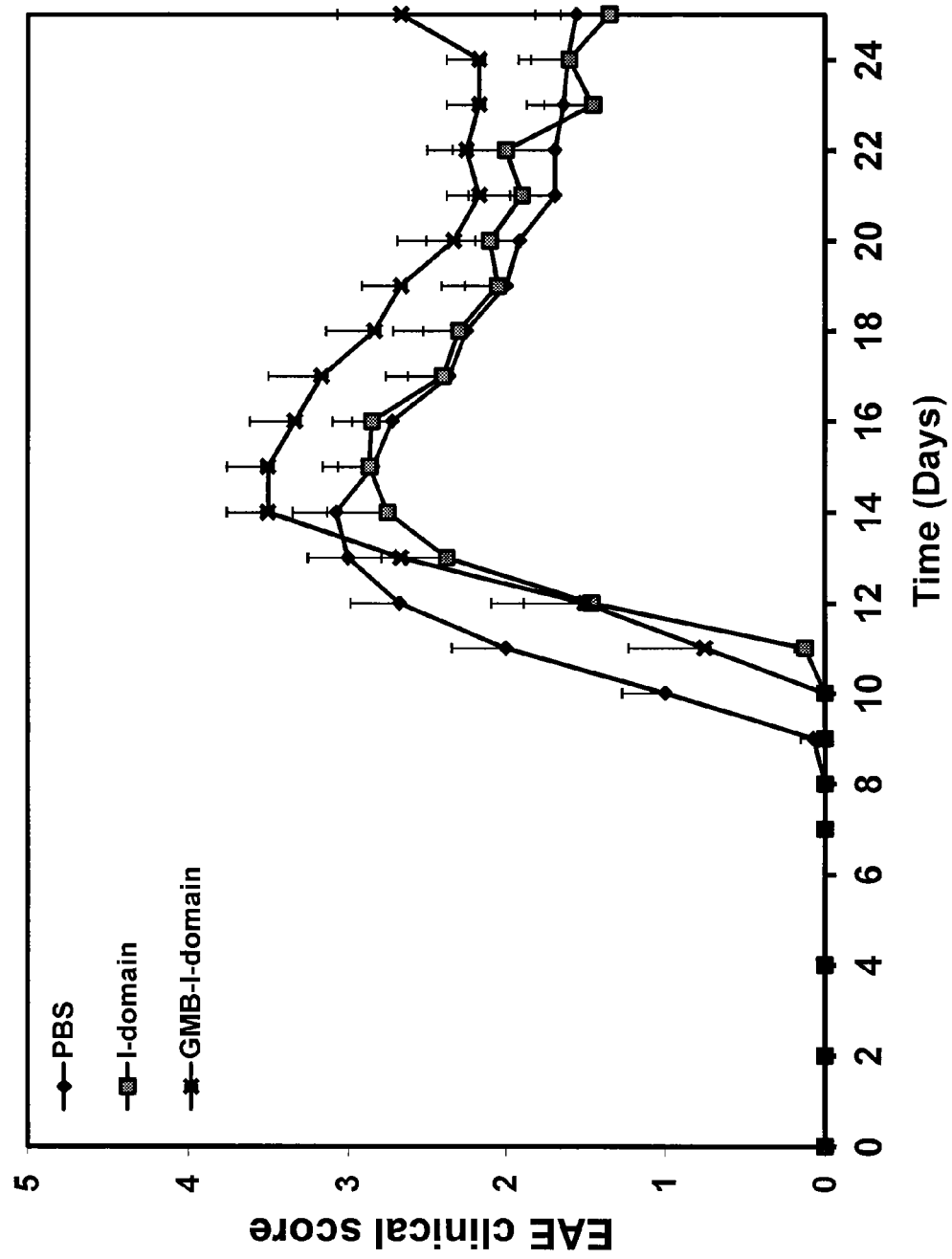

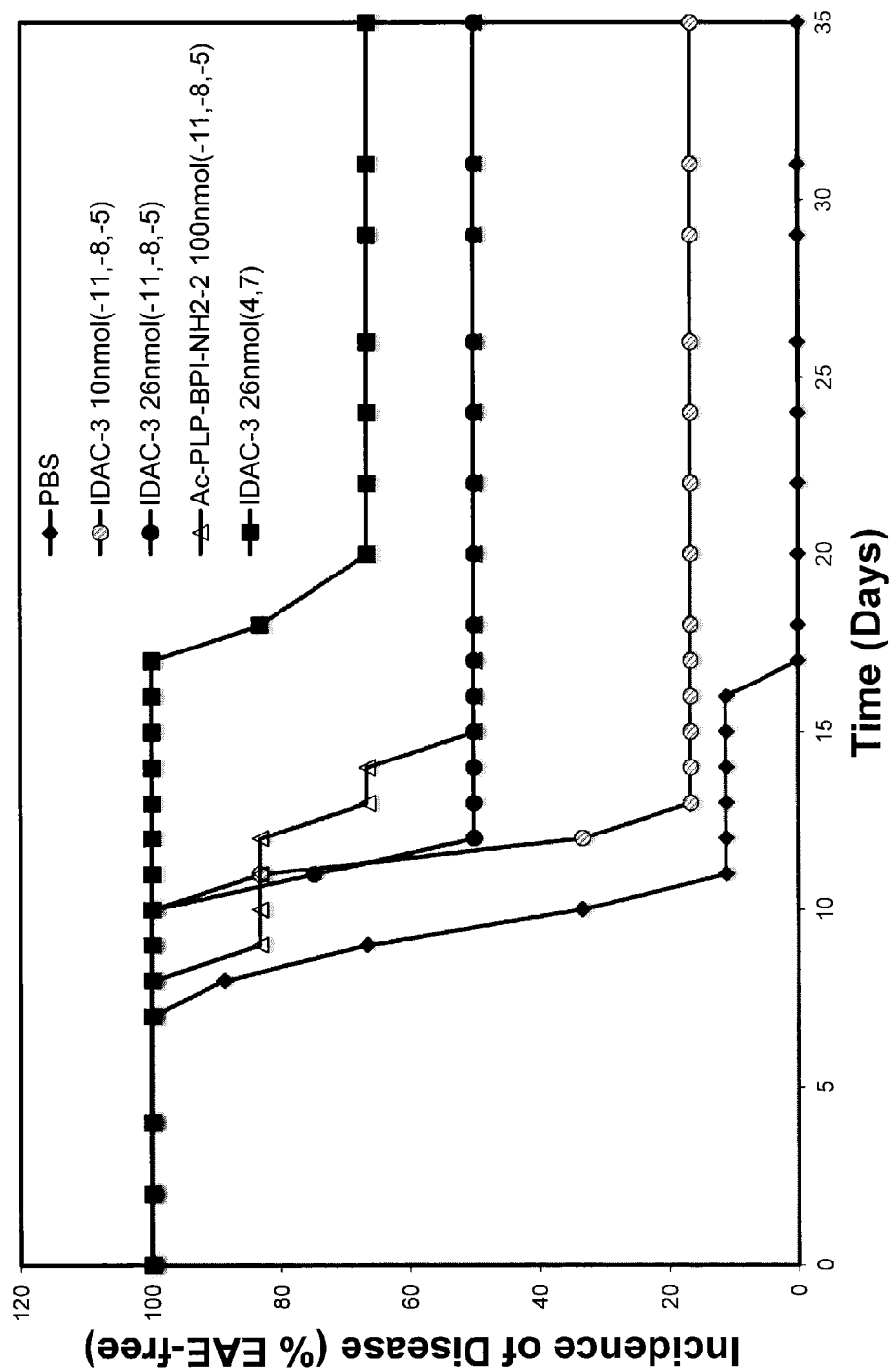

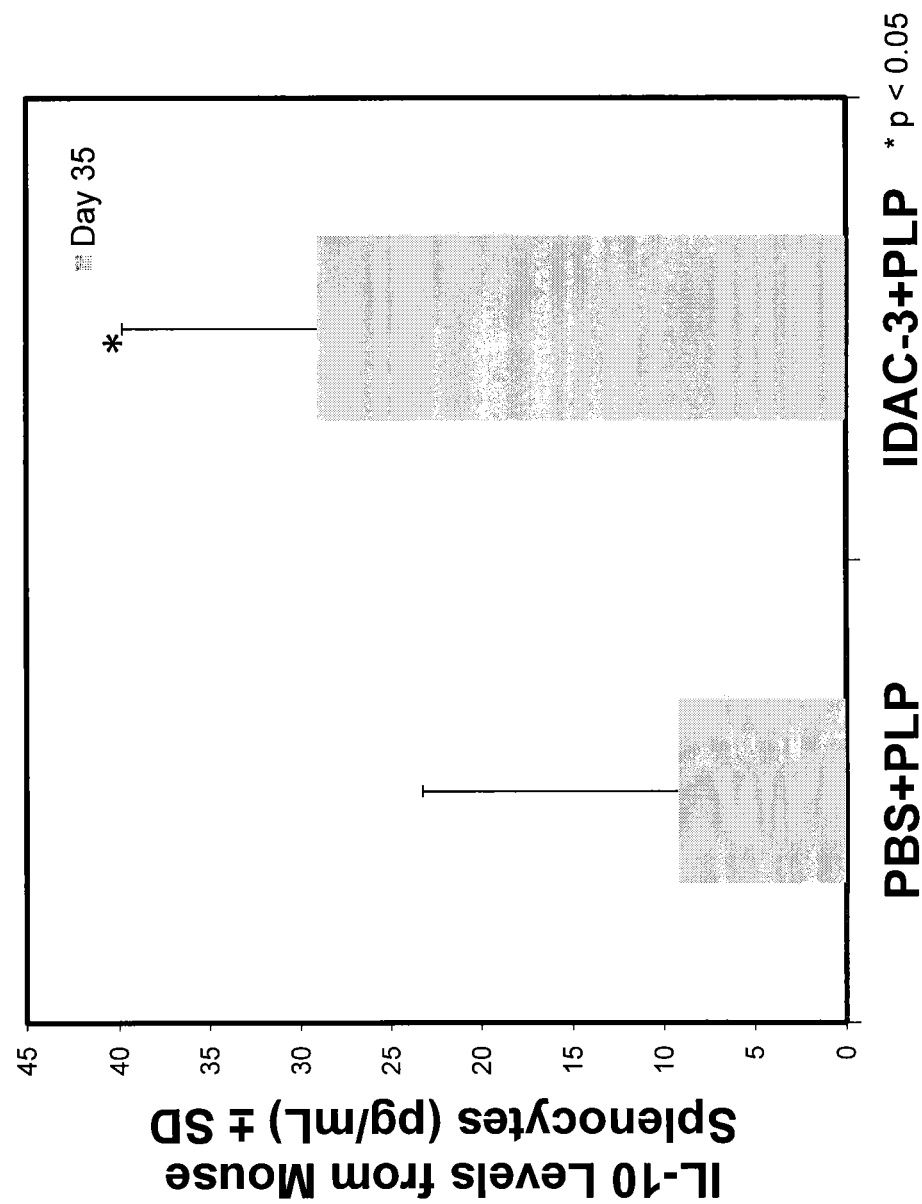

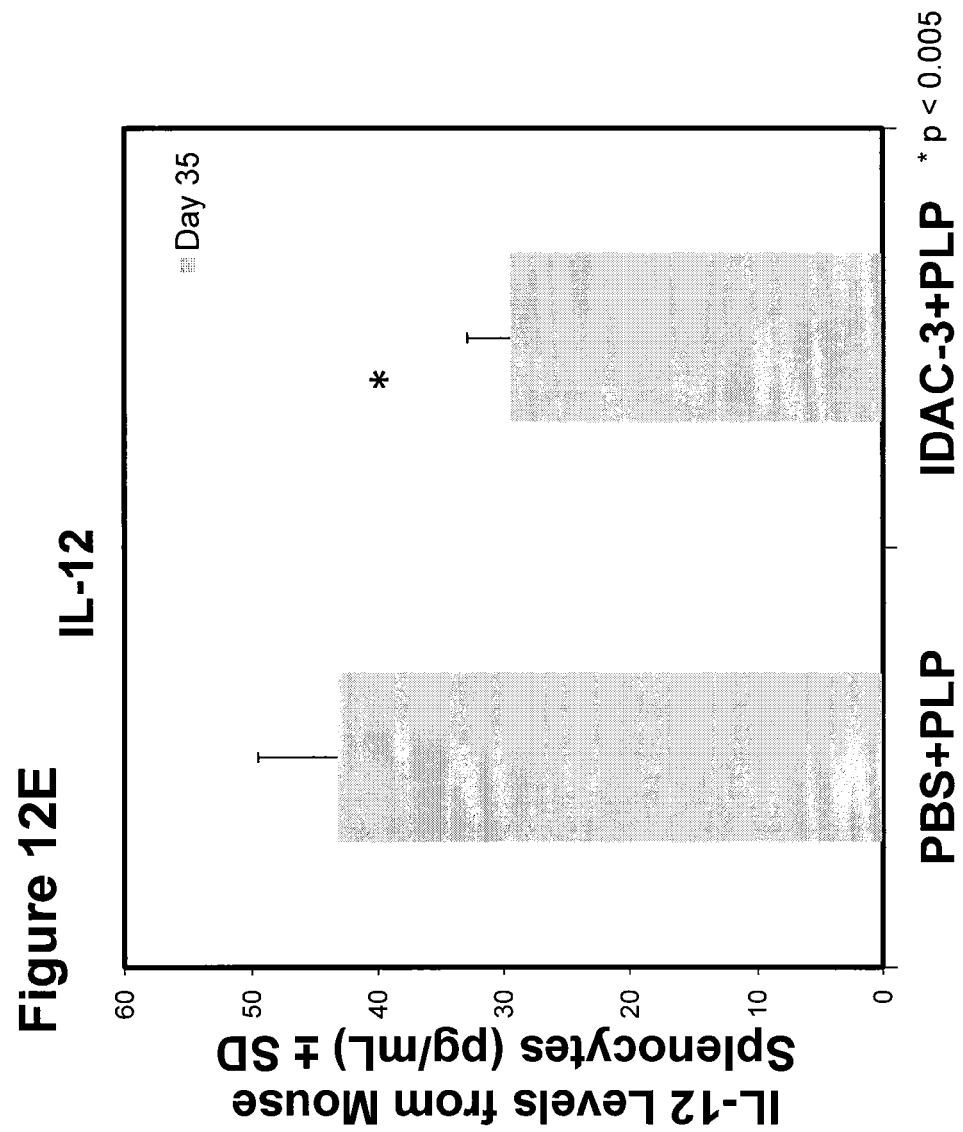

Immunological Synapse

GWYRSPFSRVVHLC = SEQ ID NO: 4

Figure 31A MOG-PEG-IDAC disease score
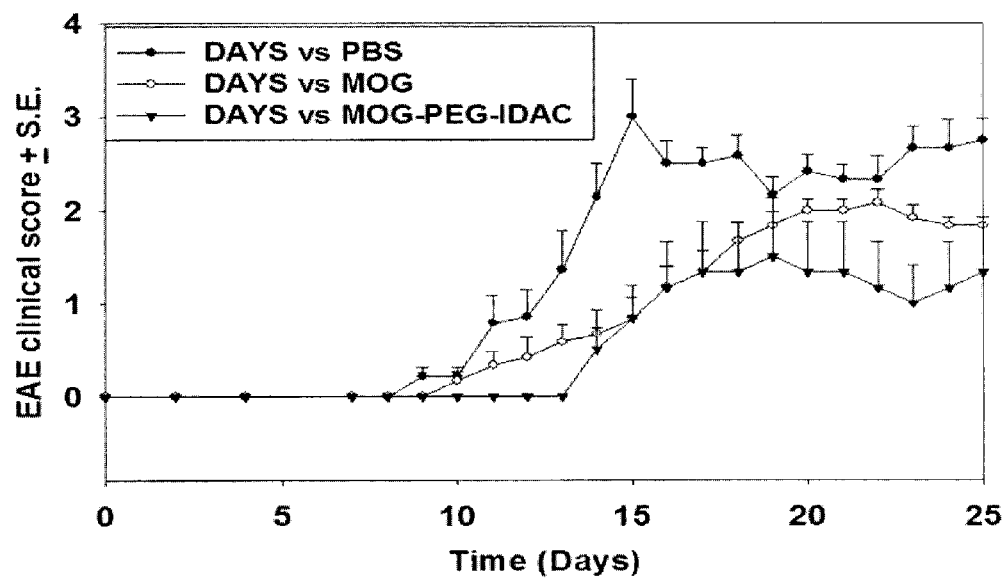
Figure 31B MOG-PEG-IDAC Incidence of Disease
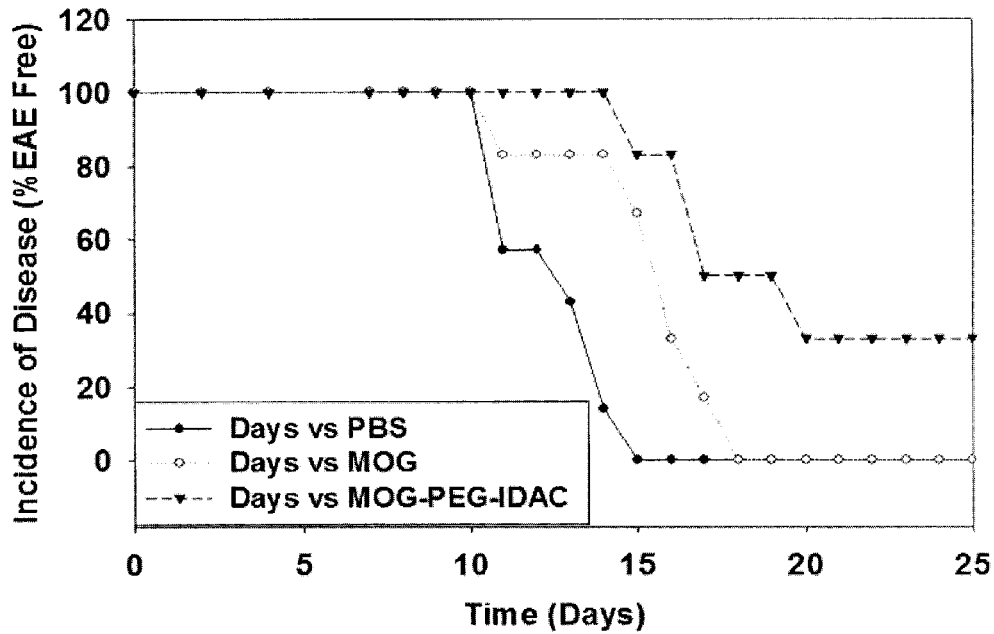

COMPOSITIONS INCLUDING I-DOMAIN ANTIGEN CONJUGATE COMPOUNDS AND METHODS FOR TREATMENT OF AUTOIMMUNE DISORDERS

CROSS-REFERENCE TO RELATED APPLICATION

This application claims priority to U.S. provisional application entitled "COMPOSITIONS INCLUDING I-DOMAIN ANTIGEN CONJUGATE COMPOUNDS AND METHODS FOR TREATMENT OF AUTOIMMUNE DISORDERS," having Ser. No. 61/583,736, filed on Jan. 6, 2012, which is entirely incorporated herein by reference.

STATEMENT REGARDING FEDERALLY SPONSORED RESEARCH OR DEVELOPMENT

This invention was made with government support under NIH Grant Nos. R01 Al-063002 and R56 AI-063002, each awarded by the U.S. National Institutes of Health of the United States government. The government has certain rights in the invention.

BACKGROUND

Autoimmune diseases such as multiple sclerosis (MS), rheumatoid arthritis, lupus, and type 1 diabetes result from the recognition and attack of self-tissues or organs by the host immune system. In the case of MS, the immune system attacks the myelin sheath of the neurons causing disruption of the signal translation in the central nervous system (CNS). Without the protection of the myelin sheath proteins, nerve impulses are either disrupted or slowed down. While the triggers of MS have not been clearly elucidated, several factors such as Epstein-Barr virus (EBV) infection, genetic predisposition, and environmental effects are thought to play roles in its development. Just as in rheumatoid arthritis and type 1 diabetes, MS results from activation of a subpopulation of self-recognizing T cells that demyelinate the nerve fibers in CNS.

One of the potential ways that T-cells recognize the myelin sheath is by activation of a subset of autoreactive T-cells, which recognize the self-myelin sheath. One possible mechanism of activation of a subpopulation T-cell is via formation of the "immunological synapse" at the interface between T-cells and antigen-presenting cells (APC). The immunological synapse is a "bull's eye"-like structure that is composed of a cluster of interactions between T-cell receptors (TCR) and major histocompatibility complex-peptide (MHC-p) at the center (signal 1) and a cluster of interactions between co-stimulatory molecules (i.e., signal 2, B7/CD28, ICAM-1/LFA-1) at the periphery of the bull's eye. The differentiation of naïve T-cells to a specific subset (i.e., Th1, Th2, Th17, T-reg) depends on the type of co-stimulatory signal delivered. Blocking signal 2 during this process could lead to immune unresponsiveness of T cells called anergy. Inhibition of ICAM-1/LFA-1 (signal 2) interaction suppresses Th1-type immune response and could promote a non-inflammatory suppressor and/or regulatory T cells.

While no cure currently exists for MS and many other autoimmune disorders, many of today's therapies, including biologic drugs such as such as interferons (Avonex®, Betaseron®), antibodies (Tysabri®), and antineoplastics (mitoxantrone), focus on slowing down and altering the disease progression. Potential drugs such as monoclonal antibodies (mAb) or small molecules that block signal 2 have been developed for treating autoimmune diseases. Unfortunately, as a potential side effect, these drugs may suppress the general immune response and compromise the ability of the host to respond to pathogenic infections.

SUMMARY

The present disclosure describes compounds including a modified I-domain peptide having two or more modified lysine residues and two or more signal 1 moieties conjugated to the modified lysine residues of the I-domain peptide, where the two or more signal 1 moieties can be the same or different. In embodiments, the lysine residues are modified with a maleibmido group. In some embodiments the compounds include a linker conjugating the signal 1 moieties to the modified lysine residues of the I-domain peptide. Compounds according to the present disclosure include embodiments where the signal 1 moieties are chosen from epitopes of proteins associated with an autoimmune disorder. In embodiments the signal 1 moieties are selected from epitopes of proteins associated with autoimmune disorders including, but not limited to, multiple sclerosis (MS), Type 1 Diabetes, rheumatoid arthritis, and lupus. In embodiments, the signal 1 moieties are chosen from SEQ ID NOs: 2-28.

Embodiments of the compounds of the present disclosure include a modified I-domain peptide having SEQ ID NO: 1, where two or more lysine residues of the sequence are modified with a maleimido group, and two or more signal 1 moieties conjugated to the modified lysine residues of the I-domain peptides, where the signal 1 moieties are chosen from epitopes of PLP, MBP, and MOG.

The present disclosure also includes pharmaceutical compositions. In embodiments, pharmaceutical compositions of the present disclosure include a therapeutically effective amount of one or more compounds of the present disclosure in a pharmaceutically acceptable carrier, where the compounds have a modified I-domain peptides with two or more modified lysine residues and two or more signal 1 moieties conjugated to the modified lysine residues of the I-domain peptide in a pharmaceutically acceptable carrier. The present disclosure also includes vaccines for prophylactic treatment of an autoimmune disorder, where, in embodiments, the vaccine includes the pharmaceutical composition described above, where the at least two signal 1 moieties are chosen from epitopes of proteins associated with the autoimmune disorder.

Additional embodiments of pharmaceutical compositions of the present disclosure include the compounds of the present disclosure in a pharmaceutically acceptable carrier, where the compounds include a modified I-domain peptide having SEQ ID NO: 1, where two or more lysine residues of the sequence are modified with a maleimido group, and two or more signal 1 moieties chosen from epitopes of PLP, MBP, and MOG conjugated to the modified lysine residues of the I-domain peptides, in a pharmaceutically acceptable carrier. The present disclosure includes vaccines for prophylactic treatment of a condition chosen from MS and EAE including a pharmaceutical composition described immediately above.

The present disclosure also includes methods of treating MS or experimental autoimmune encephalomyelitis (EAE) by administering the pharmaceutical composition described above to a subject. Embodiments of methods of the present disclosure for reducing a type 1 immune response in EAE or MS in a subject include administering a compound of the present disclosure to the subject such that a type 1 response is reduced.

The present disclosure also includes methods of making a multi-functional I-domain peptide. In embodiments, methods of making multi-functional I-domain peptides of the present disclosure include modifying the amino groups of at least two lysine residues of an I-domain peptide by reaction with N-[maleimidobutyryloxy]succinimide ester (GMBS) to functionalize at least two lysine residues with maleimido group linkers; providing at least two signal 1 moieties having a terminal cysteine residue; and conjugating the thiol group of the cysteine residue of the signal 1 moieties with the maleimido groups of the modified I-domain peptide.

BRIEF DESCRIPTION OF THE DRAWINGS

Further aspects of the present disclosure will be more readily appreciated upon review of the detailed description of its various embodiments, described below, when taken in conjunction with the accompanying drawings, described in the examples below.

FIGS. 2A-2D illustrate the purification and characterization of GMB-I-domain after the reaction of I-domain with GMBS. FIG. 2A is a SEC chromatogram showing the separation between GMB-I-domain and the remaining free GMBS. FIG. 2B is a CD spectra of the parent I-domain (circle) and GMB-I-domain (square). FIG. 2C illustrates a deconvoluted mass spectra of LC ESI-MS analysis of the GMB-I-domain protein (top) and the unmodified I-domain protein (bottom). G is the number of GMBS molecules conjugated. FIG. 2D is a digital image of an SDS-PAGE analysis of pure GMB-I-domain protein after staining with Coomassie blue: molecular weight marker (lane 1), the I-domain protein (lane 2), the reaction mixture of I-domain protein and GMBS (lane 3), and GMB-I-domain protein (lane 4).

FIG. 3A is an SEC chromatogram of IDAC, which is separated from the PLP-Cys peptide. FIG. 3B is a digital image of an SDS-PAGE analysis of different proteins after staining with Coomassie blue: molecular weight marker (lane 1), the parent I-domain protein (lane 2), the reaction mixture at pH 8.5 to prepare IDAC (lane 3), and the purified IDAC (lane 4). FIG. 3C illustrates a charge deconvoluted mass spectra of the IDAC after LC desalting. PLP is the number of PLP molecules conjugated. FIG. 3D is a CD spectra of the parent I-domain (circle) and IDAC (square).

FIG. 7A illustrate SDS-PAGE analysis of the conjugate following separation using SEC and after staining with Coomassie blue: molecular weight marker (lane 1), fractions of conjugated IDAC-3 in the order of elution from SEC (lanes 3-7). FIG. 7B is CD spectra of the parent I-domain (shaded square), IDAC-1 (open circle) and IDAC-3 (closed circle).

FIGS. 8A-8C illustrate in vivo activity of I-domain, GMB-I-domain, and PBS in mouse EAE model. After immunization with PLP peptide in CFA, the mice received i.v. injections of 26 nmol/injection/day with I-domain or GMB-I-domain on days 4 and 7. Control mice were treated with PBS on days 4, 7, and 10. Disease progression was evaluated using clinical disease scores (8A), change in body weight (8B), and incidence of disease (8C). The results are expressed as the mean±S.E. (n≥6).

FIGS. 10A-10C illustrate a comparison of the in vivo activity of IDAC-3, Ac-PLP-LABL-NH$_2$-2, and PBS in mouse EAE model. After immunization with PLP peptide in CFA, the mice received subcutaneous injections of either 10 nmol/injection/day or 26 nmol/injection/day with IDAC-3 on days −11, −8, and −5. Mice also received s.c. injections of 26 nmol/injection/day with IDAC-3 on days 4 and 7. For the Ac-PLP-LABL-NH$_2$-2 treatment group, the mice received s.c. injections of 100 nmol/injection/day of the peptide on days −11, −8, and −5. The control mice were treated with s.c. injections of PBS on days −11, −8, and −5. Disease progression was evaluated using clinical disease scores (10A), change in body weight (10B), and incidence of disease (10C). The results are expressed as the mean±S.E. (n≥6).

FIGS. 12A-12F are graphs illustrating cytokine levels (Day 13 and 35) from splenocytes of mice treated subcutaneously with PBS and IDAC-3 (26 nmol on days 4 and 7; FIG. 12): (A) IL-17, (B) IL-2, (C) IL-5, (D) IL-10, (E) IL-12, and (F) TNFα.

FIG. 31A-31C illustrates a comparison of the in vivo activity of MOG-PEG-IDAC, MOG, and PBS in C57BL/6 mouse EAE model. After immunization with MOG peptide in CFA, the mice received treatment with s.c. injections of 26 nmol/injection/day with MOG-PEG-IDAC on days 4 and 7 (n=3, p<0.05). For the PBS and MOG treatment group, the mice received s.c. injections of 100 nmol/injection/day on days 4, 7, and 10 (n=6, p<0.0001). Disease progression was evaluated using clinical disease scores (31A), incidence of disease (31B), and change in body weight (31C). The results are expressed as the mean±S.E. (n≥6).

DESCRIPTION

Figure 1:
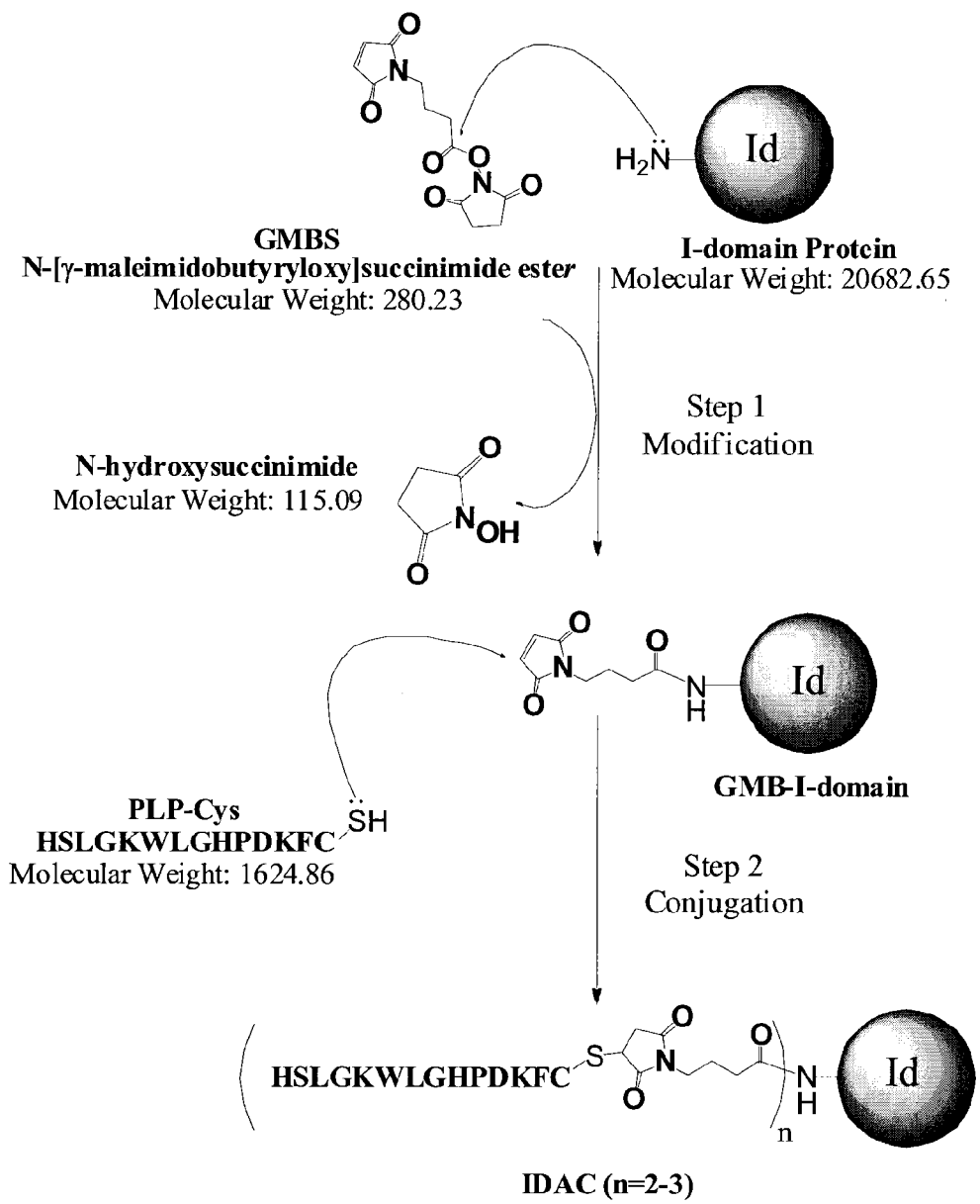
FIG. 1 shows a schematic representation of a two-step conjugation reaction to prepare IDAC.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification that are incorporated by reference are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Unless otherwise indicated, any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained in the literature.

It must be noted that, as used in the specification and the appended embodiments, the singular forms "a," "an," and "the" include plural referents unless the context clearly dictates otherwise. Thus, for example, reference to "a cell" includes a plurality of cells. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law, and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

In describing the disclosed subject matter, the following terminology will be used in accordance with the definitions set forth below.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present disclosure include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, insect viruses (baculovirus), and the like, vectors derived from bacteriophage nucleic acid, and synthetic oligonucleotides like chemically synthesized DNA or RNA. The term "nucleic acid" further includes modified or derivatized nucleotides and nucleosides such as, but not limited to, halogenated nucleotides such as, but not only, 5-bromouracil, and derivatized nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, e.g., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

It is advantageous for some purposes that a nucleotide sequence is in purified form. The term "purified" in reference to nucleic acid represents that the sequence has increased purity relative to the natural environment.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

The term "peptide" or "polypeptide" as used herein refers to proteins and protein fragments. Peptides may have tertiary structure. Peptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: alanine (Ala, A), arginine (Arg, R), asparagine (Asn, N), aspartic acid (Asp, D), cysteine (Cys, C), glutamine (Gln, Q), glutamic acid (Glu, E), glycine (Gly, G), histadine (His, H), I isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

The term "variant" refers to a peptide or polynucleotide that differs from a reference peptide or polynucleotide, but retains essential properties. A typical variant of a peptide differs in amino acid sequence from another, reference peptide. Generally, differences are limited so that the sequences of the reference peptide and the variant are closely similar overall and, in many regions, identical. A variant and reference peptide may differ in amino acid sequence by one or more modifications (e.g., substitutions, additions, and/or deletions). A variant of a peptide includes conservatively modified variants (e.g., conservative variant of about 75, about 80, about 85, about 90, about 95, about 98, about 99% of the original sequence). A substituted or inserted amino acid residue may or may not be one encoded by the genetic code. A variant of a peptide may be naturally occurring, such as an allelic variant, or it may be a variant that is not known to occur naturally.

The present disclosure includes peptides, which are derivable from the naturally occurring sequence of the peptide. A peptide is said to be "derivable from a naturally occurring amino acid sequence" if it can be obtained by fragmenting a naturally occurring sequence, or if it can be synthesized based upon knowledge of the sequence of the naturally occurring amino acid sequence or of the genetic material (DNA or RNA) that encodes this sequence. Included within the scope of the present disclosure are those molecules, which are said to be "derivatives" of a peptide. Such a "derivative" or "variant" shares substantial similarity with the peptide or a similarly sized fragment of the peptide and is capable of functioning with substantially similar biological activity as the peptide (e.g., retains biological activity of the naturally occurring peptide, but allowing for the activity to be reduced or increased with respect to the naturally occurring peptide).

A derivative of a peptide is said to share "substantial similarity" with the peptide if the amino acid sequences of the derivative is at least 80%, at least 90%, at least 95%, or the same as that of either the peptide or a fragment of the peptide having the same number of amino acid residues as the derivative.

The protein or peptide derivatives of the present disclosure include fragments which, in addition to containing a sequence that is substantially similar to that of a naturally occurring peptide may contain one or more additional amino acids at their amino and/or their carboxy termini. Similarly, the disclosure includes peptide fragments which, although containing a sequence that is substantially similar to that of a naturally occurring peptide, may lack one or more additional amino acids at their amino and/or their carboxy termini that are naturally found on the peptide.

The disclosure also encompasses the obvious or trivial variants of the above-described fragments which have inconsequential amino acid substitutions (and thus have amino acid sequences which differ from that of the natural sequence) provided that such variants have an activity which is substantially identical to that of the above-described derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

Modifications and changes can be made in the structure of the peptides of this disclosure and still obtain a molecule having similar characteristics as the peptide (e.g., a conservative amino acid substitution). For example, certain amino acids can be substituted for other amino acids in a sequence without appreciable loss of activity. Because it is the interactive capacity and nature of a peptide that defines that peptide's biological functional activity, certain amino acid sequence substitutions can be made in a peptide sequence and nevertheless obtain a peptide with like properties.

In making such changes, the hydropathic index of amino acids can be considered. The importance of the hydropathic amino acid index in conferring interactive biologic function on a peptide is generally understood in the art. It is known that certain amino acids can be substituted for other amino acids having a similar hydropathic index or score and still result in a peptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant peptide, which in turn defines the interaction of the peptide with other molecules, such as enzymes, substrates, receptors, antibodies, antigens, and the like. It is known in the art that an amino acid can be substituted by another amino acid having a similar hydropathic index and still obtain a functionally equivalent peptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent peptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent peptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu).

As used herein, the term "linker" embraces a molecule that joins two other molecules together. In one aspect, the linker is any amino acid including naturally occurring or chemically synthesized amino acids. In embodiments of the present disclosure, a "linker" is a flexible, non-substrate sequence of amino acid residues resistant to proteolytic degradation. The linker may include molecules such as maleimido groups. In embodiments, a linker of the present disclosure includes a polymer such as, but not limited to PEG. In embodiments, a linker of the present disclosure may include a combination of molecules such as, but not limited to amino acid molecules, maleimido molecules, and polymer molecules.

As used herein, the term "signal 1 moiety" refers to a peptide eptitope, e.g., the peptide portion of an antigen or antigen mimetics to which important T-cell receptors (TCRs) bind. In embodiments of the present disclsoure the signal 1 moieties are epitopes of protein antigens associated with an autioimmune disease. For example, for multiple sclerosis, exemplary protein antigens would include, but are not limited to, epitopes of proteolipid protein (PLP), myelin basic protein (MBP), and myelin oligodendrocyte glycoprotein (MOG). Thus, epitopes of PLP, MBP, and MOG are representative signal 1 moieties of the present disclosure. Exemplary protein antigens for other autoimmune diseases include, but are not limited to, glutamic acid decarboxylase (GAD), insulin zinc transporter (ZNT8), insulinoma antigen (IA-2), and insulin for type 1 diabetes; and human cartilage gp-39, cartilage proteins melanoma inhibitory activity (MIA), type II collagen, and citrullinated proteins (e.g., fibrin) for rheumatoid arthritis.

The terms "treat", "treating", and "treatment" are an approach for obtaining beneficial or desired clinical results. Specifically, beneficial or desired clinical results include, but are not limited to, alleviation of symptoms, diminishment of extent of disease, stabilization (e.g., not worsening) of disease, delaying or slowing of disease progression, substantially preventing spread of disease, amelioration or palliation of the disease state, and remission (partial or total) whether detectable or undetectable. In addition, "treat", "treating", and "treatment" can also mean prolonging survival as compared to expected survival if not receiving treatment and/or can be therapeutic in terms of a partial or complete cure for a disease and/or adverse effect attributable to the disease. As used herein, the terms "prophylactically treat" or "prophylactically treating" refers completely, substantially, or partially preventing a disease/condition or one or more symptoms thereof in a host. Similarly, "delaying the onset of a condition" can also be included in "prophylactically treating", and refers to the act of increasing the time before the actual onset of a condition in a patient that is predisposed to the condition.

The term "host" or "organism" as used herein includes humans, mammals (e.g., cats, dogs, horses, etc.), insects, living cells, and other living organisms. A living organism can be as simple as, for example, a single eukaryotic cell or as complex as a mammal. Typical hosts to which embodiments of the present disclosure relate will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. Hosts that are "predisposed to" condition(s) can be defined as hosts that do not exhibit overt symptoms of one or more of these conditions but that are genetically, physiologically, or otherwise at risk of developing one or more of these conditions.

By "administration" is meant introducing a compound of the present disclosure into a subject; it may also refer to the act of providing a composition of the present disclosure to a subject (e.g., by prescribing). One preferred route of administration of the compound is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

The term "therapeutically effective amount" as used herein refers to that amount of the compound being administered which will relieve or prevent to some extent one or more of the symptoms of the condition to be treated or can stop, halt, delay or reverse the progression of the disease or delay or prevent onset of the disease in a host. In reference to conditions/diseases that can be directly treated with a composition of the disclosure, a therapeutically effective amount refers to that amount which has the effect of preventing the condition/disease from occurring in an animal that may be predisposed to the disease but does not yet experience or exhibit symptoms of the condition/disease (prophylactic treatment), alleviation of symptoms of the condition/disease, diminishment of extent of the condition/disease, stabilization (e.g., not worsening) of the condition/disease, preventing the spread of condition/disease, delaying or slowing of the condition/disease progression, amelioration or palliation of the condition/disease state, and combinations thereof. The term "effective amount" refers to that amount of the compound being administered which will produce a reaction that is distinct from a reaction that would occur in the absence of the compound.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutical composition" refers to the combination of an active agent (e.g., the IDAC compounds of the present disclosure) with a pharmaceutically acceptable carrier. As used herein, a "pharmaceutical composition" refers to a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

A "pharmaceutically acceptable excipient," "pharmaceutically acceptable diluent," "pharmaceutically acceptable carrier," or "pharmaceutically acceptable adjuvant" refers to an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "unit dosage form," as used herein, refers to physically discrete units suitable as unitary dosages for human and/or animal subjects, each unit containing a predetermined quantity of a compound calculated in an amount sufficient (e.g., weight of host, disease, severity of the disease, etc.) to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

Discussion

Embodiments of the present disclosure include methods and compounds for treatment, prophylactic treatment, and vaccine-like treatment of autoimmune disorders. The compounds of the present disclosure include a modified I-domain peptide and two or more signal 1 moieties conjugated to the I-domain peptide, where the two or more signal 1 moieties may be the same or different. Since the compounds of the present disclsoure can conjugate more than one type of signal 1 moiety at one time and present these to the antigen presenting cells (APC) while simultaneously blocking immunilogical synapse formation, the present i-domain antigen conjugate (IDAC) compounds can provide for multi-functional peptide inhibition. The multi-functional capability of the modified I-domain peptide provides a unique feature for de-sensitizing the immune system to multiple antigenic host proteins.

As discussed above and in greater detail below, many autoimmune disorders are characterized by the host's immune system mounting an attack on the host's own proteins. In such disorders, the host's T-cells recognize certain host proteins as antigens and attack, creating an inflammatory response. Different disorders are associated with different proteins. For instance, multiple sclerosis (MS) is associated with attack of host proteins of the nervous system, including proteolipid protein (PLP), myelin basic protein (MBP), myelin oligodendrocyte glycoprotein (MOG), and astrocyte-protein S100β. Exemplary protein antigens for other autoimmune diseases include, but are not limited to, glutamic acid decarboxylase (GAD), insulin zinc transporter (ZNT8), insulinoma antigen (IA-2), and insulin for type 1 diabetes; and human cartilage gp-39, proteins melanoma inhibitory activity (MIA), type II collagen, and citrullinated proteins (e.g., fibrin) for rheumatoid arthritis.

Current drug therapies for many autoimmune disorders result in general suppression of the immune system, which can result in making the host susceptible to other infections. Thus, a newer approach has been to target the antigenic peptides associated with autoimmune disorders and induce tolerance by the host immune system. One approach, described in greater detail in the examples below, as well as in Manikwar et al., "Antigen-specific Blocking of CD4-specific Immunological Synapse Formation using BPI and Current Therapies for Autoimmune Disease", (Manikwar P, Kiptoo P, Badawi A H, Buyuktimkin B, Siahaan T; J. Med Res Rev. 2012; 32: 727-764 (hereby incorporated by reference herein)), involves blocking formation of the immunological synapse (IS) between T-cells and antigen-presenting cells (APC's) by blocking ICAM-1/LFA-1 (signal 2) interactions in conjunction with signal 1 interactions specific to the peptide antigens associated with the auto-immune disease. FIGS. 13-14 illustrate interaction between T-cells and APC's and IS formation. Blocking of IS formation is believed to result in the T-cells adopting a regulatory rather than an inflammatory response in response to the peptide antigens.

In a version of this approach, bifunctional peptide inhibitors (BPIs) were developed that simultaneously block signal 2 while presenting a peptide antigen associated with the autoimmune disorder (signal 1 moiety) to the APC (signal 1). The BPI has one portion (e.g., a cell adhesion peptide) that inhibits ICAM-1/LFA-1 (signal 2) interaction and a second portion that includes antigenic peptides for the specific disease (see FIGS. 15-17 illustrating the BPI approach described in Manikwar et al., J. Med Res Rev. 2012; 32: 727-764). These BPI's have proven successful in mediating immune response against the peptide antigen, thereby slowing or arresting disease progression. However, the BPI's can only conjugate one signal 1 moiety, and thus only present one peptide antigen to the APC. Over time, epitope spreading can occur, where other peptides become antigenic and the disease again progresses. For, instance, in the case of MS, if PLP is antigenic early in disease progression, and a BPI with an epitope of PLP as the signal 1 moiety is used to treat a patient with MS, the treatment can alter the immune response of the host to PLP, converting the inflammatory response to a regulatory response and slowing or arresting the disease. But, over time, other protein antigens associated with MS, such as antigens from myelin basic protein (MBP) and/or myelin oligodendrocyte glycoprotein (MOG) become antigenic as well, and the BPI compound becomes less effective. Unlike the BPIs, the IDAC compounds of the present disclosure can conjugate more than one type of signal 1 moiety at one time and present these to the APC while also blocking IS. Thus, the present I-domain antigen conjugate (IDAC) compounds can provide for multi-functional peptide inhibition.

The compounds of the present disclosure can elicit a similar interaction with the immune system, presenting antigenic peptides to the APC and blocking IS formation to induce tolerance to the antigenic peptides, but, since they are multifunctional, the present compounds can induce a regulatory response to multiple peptide epitopes that are associated with an autoimmune disorder, thereby providing a multi-faceted approach. The present compounds can enhance the immune response to a single peptide by presenting multiple copies of an epitope of the peptide simultaneously. The compounds of the present disclsoure can also provide a broader response by presenting multiple antigens associated with a disorder (e.g., PLP, MBP, and MOG for MS), thereby reducing or suppressing immune response to more than one potentially antigenic protein at a time and reducing or eliminating epitope spreading and prolonging the effectiveness of the treatment.

I-Domain Peptide

The IDAC compounds of the present disclosure include a modified I-domain peptide that is able to conjugate two or more signal 1 moieties. The I-domain peptide portion of the compound inhibits ICAM-1/LFA-1 (signal 2) to block IS formation, and the conjugated signal 1 moieties are presented to the APC to induce tolerance. The I-domain is described in greater detail in the Examples below. In embodiments of the present disclosure, the I-domain peptide is derived from a portion of a protein involved in signal 2 interaction between T-cells and APCs. The portion of the protein forming the I-domain peptide can have tertiary structure to enable proper binding with a receptor. In an embodiment, the I-domain is derived from the binding region of LFA-1 to ICAM-1. In an embodiment, the I-domain is derived from the α-subunit of LFA-1 that interacts with the D1 domain of ICAM-1. In embodiments, the I-domain peptide has SEQ ID NO: 1 from Example 1, Table 1A. In embodiments, the I-domain peptide can have a sequence that is longer or shorter that SEQ ID NO: 1, so long as it retains binding activity to ICAM-1. The I-domain contains several lysine residues that can be modified to enable conjugation (e.g., binding, interaction) with a signal 1 moiety. Table 2 for Example 1, below, illustrates various locations for modification of the I-domain. Since more than one lysine residue can be modified to enable conjugation with a signal 1 moiety, more than one different type of signal 1 moiety can be conjugated to a single I-domain peptide. In embodiments, the I-domain peptide includes 2 to 20 modified lysine residues. In embodiments, the I-domain includes anywhere from 2 to 20 modified lysine residues, including any number in between (e.g., 12, 8, 3, and the like).

In embodiments, the I-domain peptide and the signal 1 moieties are conjugated via linkers. In embodiments the linker comprises a maleimido group. In embodiments, the linker may also include a spacer such as one or more PEG groups or additional maleimido groups, or other appropriate linker spacer combinations. The maleimido group is capable of conjugating a cysteine residue on the signal 1 moiety. Thus, in embodiments, two or more lysine residues of the I-domain peptide are modified with maleimido groups to enable conjugation to cysteine residues on two or more signal 1 moieties. In other embodiments the lysine residues can be modified by mutation to a cysteine residue, which can also be used to conjugate via a maleimido linker on signal 1 moieties.

The reactions used for modification of the lysine residues with maleimido groups are illustrated and described in greater detail in the examples and figures below. Briefly, in embodiments, the amino groups of at least two lysine residues of an I-domain peptide are modified by reaction with N-[maleimidobutyryloxy]succinimide ester (GMBS) to functionalize the at least two lysine residues with maleimido groups. Other methods or modifications and variations of the above-described methods of functionalizing lysine residues to conjugate the I-domain peptide to two or more signal 1 moieties are intended to be included in the scope of this disclosure.

Signal 1 Moiety

The compounds of the present disclosure can also include two or more signal 1 moieties conjugated to the I-domain peptides. The signal 1 moieties of the present disclosure are epitopes of proteins associated with an autoimmune disorder. Thus, in embodiments, the signal 1 moieties can include portions of antigenic proteins implicated in autoimmune disorders. Since the I-domain peptide has two or more modified lysine residues that can conjugate (e.g., via a linker) the signal 1 moieties, more than one different type of signal 1 moiety can be included on the same IDAC compound. For instance, for the treatment of MS, an embodiment of an IDAC compound of the present disclosure may include one or more PLP antigens, one or more MBP antigens, and/or one or more MOG antigens, or a combination of two or more of those as the signal 1 moieties.

In embodiments, the signal 1 moieties are chosen from epitopes of proteins associated with an autoimmune disorder including, but not limited to, multiple sclerosis, type 1 diabetes, and rheumatoid arthritis. In embodiments for IDAC compounds to treat MS, the signal 1 moieties can include epitopes of proteins including, but not limited to, PLP, MBP, MOG, and astrocyte-protein 510013. In embodiments for IDAC compounds to treat type 1 diabetes, the signal 1 moieties can include epitopes of proteins including, but not limited to, GAD, ZNT8, IA-2, and insulin. In embodiments for IDAC compounds to treat rheumatoid arthritis, the signal 1 moieties can include epitopes of proteins including, but not limited to, human cartilage gp-39, cartilage proteins MIA, type II collagen, and citrullinated proteins (e.g., fibrin). In embodiments for IDAC compounds to treat lupus, the signal 1 moieties can include epitopes of proteins including, but not limited to, nucleosomal and chromatin peptides (see, Kaliyaperumal, A., Michaels, M. A., and Datta, S. K. (1999). Antigen-specific therapy of murine lupus nephritis using nucleosomal peptides: tolerance spreading impairs pathogenic function of autoimmune T and B cells. J Immunol 162, 5775-5783. Kaliyaperumal, A., Michaels, M. A., and Datta, S. K. (2002). Naturally processed chromatin peptides reveal a major autoepitope that primes pathogenic T and B cells of lupus. J Immunol 168, 2530-2537).

In embodiments of the IDAC compounds of the present disclosure, the signal 1 moiety can include an epitope of a protein associated with an autoimmune disorder where the epitope has been modified to have a terminal cysteine residue (e.g., a PLP peptide-cys). In an embodiment for compounds for treatment of MS, the IDAC compounds of the present disclsoure can include at least one signal 1 moiety having SEQ ID NO: 2 (amino acids 139-151 of PLP plus cysteine) (see Table 1A in Example 1, below). In other embodiments, the IDAC compounds can include at least one signal 1 moiety chosen from PLP, MBP, and MOG peptides provided in Tables 1A and 1B below, SEQ ID NOs: 2-28. In embodiments of the IDAC compounds of the present disclosure, the IDAC compounds include a combination of signal 1 moieties from SEQ ID NOs: 2-28. In the sequences listed in Tables 1A and 1B some of the sequences have a terminal cysteine while others do not. One of skill in the art will recognize that any of the listed sequences can be modified to include a terminal cysteine residue or to delete it, as appropriate.

In embodiments, the IDAC molecule can include more than one different type of antigen from the same proteins as signal 1 moieties. For instance, in an embodiment, two different signal 1 moieties may include two different epitopes of PLP. The signal 1 moieties can include any combination of various epitopes of any one or more antigenic peptides associated with the autoimmune disorder to be treated. Also, it is contemplated that in some embodiments, all of the signal 1 moieties may be the same, or all of them may be different, or there may be a combination of different signal 1 moieties and multiple identical signal 1 moieties on an IDAC compound of the present disclosure. Since there can be up to about 20 different modified/activated lysine residues on the I-domain peptide, there can be about 2 to 20 signal 1 moieties in a single IDAC compound of the present disclosure.

In embodiments of the present disclosure, the signal 1 moiety has a terminal cysteine for conjugation to the I-domain via a conjugation of the thiol group of the cysteine residue to a maleimido group linker on the modified lysine residues of the I-domain peptide. The signal 1 moiety can include a terminal cysteine on the C-terminal end, the N-terminal end or both. The signal 1 moiety may also be capped with an acetyl group (AC) at one of the terminal ends. If a signal 1 moiety has both a terminal cysteine and an acetyl cap, they will be at opposite ends of the peptide (e.g., Ac at the C-terminal end and terminal cysteine at the N-terminal end or vice versa).

Linker

Embodiments of the compounds of the present disclosure can include a linker conjugating the modified lysine residues of the I-domain peptide to cysteine residues on the two or more signal 1 moieties. In embodiments, the linker includes a maleimido group capable of conjugating modified lysine residues with a thiol group on a cysteine residue of the signal 1 moieties. In embodiments, the modified lysine residues of the I-domain peptide may be modified by reaction with GMBS to functionalize the lysine residue with a maleimido group. In embodiments, the linker may include additional "spacers" to extend the length of the linker. The linker may include one or more maleimido groups, and optionally one or more spacers. In embodiments, spacers are carbon groups that may be tailored to a desired length, e.g., polymers. For instance, the spacer may include, but is not limited to, a polymer such as poly-ethylene glycol (PEG) or an amino acid linker such as poly-Gly. The length of the linker can be adjusted as appropriate by one of skill in the art.

Pharmaceutical Compounds and Vaccines

The present disclosure also includes pharmaceutical compounds including the IDAC compounds of the present disclosure and a pharmaceutically acceptable carrier. The pharmaceutical compositions of the present disclosure can be prepared in various formulations as can be determined by one of skill in the art for treatment of autoimmune disorders such as, but not limited to, MS, type 1 diabetes, lupus, and rheumatoid arthritis. In embodiments pharmaceutical compositions including the IDAC compounds of the present disclosure may be used for prophylactic treatment of a host at risk or in early stages of an autoimmune disorder. Thus, the pharmaceutical compositions of the present disclosure can be used to treat and/or prevent autoimmune disorders, including, but not limited to, arresting or slowing the progression of an autoimmune disorder, delaying onset of an autoimmune disorder or symptoms associated with the disorder, and/or alleviating symptoms of autoimmune disorders.

In embodiments, the IDAC compounds of the present disclosure may be combined with a pharmaceutically acceptable carrier and included in a vaccine formulation for delivery as a vaccine to a host in need of treatment for an autoimmune disorder.

Administration of the active compounds and salts described herein can be via any of the accepted modes of administration for therapeutic agents. These methods include oral, parenteral, transdermal, subcutaneous and other systemic modes.

Depending on the intended mode, the compositions may be in the form of solid, semisolid or liquid dosage forms, such as, for example, tablets, suppositories, pills, capsules, powders, liquids, suspensions, skin patch, or the like, preferably in unit dosage forms suitable for single administration of precise dosages. The compositions can include a conventional pharmaceutical excipient and an active compound of the present disclosure or the pharmaceutically acceptable salts thereof (e.g., prostratin, bryostatin, and their analogs) and, in addition, may include other medicinal agents, pharmaceutical agents, carriers, adjuvants, diluents, etc.

Embodiments of the compounds of the present disclosure are typically administered to a patient in the form of a pharmaceutical composition or formulation. Such pharmaceutical compositions can be administered to the patient by any acceptable route of administration including, but not limited to, oral, rectal, vaginal, nasal, inhaled, topical (including transdermal) and parenteral modes of administration.

Accordingly, an embodiment of the present disclosure is directed to a pharmaceutical composition comprising a pharmaceutically-acceptable carrier or excipient and a therapeutically effective amount of a compound of the present disclosure or a pharmaceutically acceptable salt thereof. Optionally, such pharmaceutical compositions may contain other therapeutic and/or formulating agents if desired. When discussing compositions, the "compound of the present disclosure" may also be referred to herein as the "active agent" or "agent". As used herein, the term "compound of the present disclosure" is intended to include a novel compound described in formulae provided herein and in the claims (e.g., the IDAC compounds of the present disclosure).

The pharmaceutical compositions of the present disclosure typically contain a therapeutically effective amount of a compound of the present disclosure or a pharmaceutically-acceptable salt thereof. Typically, such pharmaceutical compositions can contain about 0.1 to about 95% by weight of the active agent; preferably, about 5 to about 70% by weight; and more preferably about 10 to about 60% by weight of the active agent.

A conventional carrier or excipient can be used in the pharmaceutical compositions of the present disclosure. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this present disclosure are commercially-available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the present disclosure are preferably packaged in a unit dosage form. The term "unit dosage form" refers to a physically discrete unit suitable for dosing a patient, e.g., each unit containing a predetermined quantity of active agent (e.g., IDAC compounds of the present disclosure) calculated to produce the desired therapeutic effect either alone or in combination with one or more additional units. For example, such unit dosage forms can be capsules, tablets, pills, and the like, or unit packages suitable for parenteral administration.

In an embodiment, the pharmaceutical compositions of the present disclosure are suitable for oral administration. Suitable pharmaceutical compositions for oral administration can be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present disclosure as an active ingredient.

When intended for oral administration in a solid dosage form (i.e., as capsules, tablets, pills and the like), the pharmaceutical compositions of the present disclosure can typically include the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the present disclosure. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like.

Pharmaceutical compositions of the present disclosure may also be formulated to provide slow or controlled release of the active agent using, by way of example, hydroxypropyl methyl cellulose in varying proportions; or other polymer matrices, liposomes and/or microspheres. In addition, the pharmaceutical compositions of the present disclosure may optionally contain opacifying agents and can be formulated so that they release the active ingredient only, or preferentially, in a certain portion of the gastrointestinal tract, optionally, in a delayed manner. Examples of embedding compositions which can be used include polymeric substances and waxes. The active agent can also be in microencapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of the present disclosure can also be administered parenterally (e.g., by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations can be rendered sterile by use of a sterile injectable medium, a sterilizing agent, filtration, irradiation, or heat.

Alternatively, the pharmaceutical compositions of the present disclosure are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the present disclosure will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition can be in the form of a capsule or cartridge (made, for example, from gelatin) comprising a compound of the present disclosure and a powder suitable for use in a powder inhaler. Suitable powder bases include, by way of example, lactose or starch.

The compounds of the present disclosure can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, can be used in such transdermal compositions if desired.

If desired, the compounds of this present disclosure can be administered in combination with one or more other therapeutic agents. In this embodiment, a compound of this present disclosure is either physically mixed with the other therapeutic agent to form a composition containing both agents; or each agent is present in separate and distinct compositions which are administered to the patient simultaneously or sequentially.

For example, a compound of the present disclosure can be combined with a second therapeutic agent using conventional procedures and equipment to form a composition comprising a compound of the present disclosure (e.g., the IDAC compounds described above) and a second therapeutic agent. Additionally, the therapeutic agents can be combined with a pharmaceutically acceptable carrier to form a pharmaceutical composition comprising a compound of the present disclosure, a second therapeutic agent and a pharmaceutically acceptable carrier. In this embodiment, the components of the composition are typically mixed or blended to create a physical mixture. The physical mixture is then administered in a therapeutically effective amount using any of the routes described herein. Alternatively, the therapeutic agents may remain separate and distinct before administration to the patient. In this embodiment, the agents are not physically mixed together before administration but are administered simultaneously or at separate times as separate compositions. Such compositions can be packaged separately or can be packaged together as a kit. The two therapeutic agents in the kit can be administered by the same route of administration or by different routes of administration. Any therapeutic agent compatible with the compounds of the present disclosure can be used as the second therapeutic agent.

In an embodiment, multiple doses of the compounds of the present disclosure are administered. The frequency of administration of the agent can vary depending on any of a variety of factors, e.g., severity of the symptoms, and the like. For example, in an embodiment, the agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). In some embodiments, the agent is administered continuously for a period of time.

The duration of administration of the agent, e.g., the period of time over which the agent is administered, can vary, depending on any of a variety of factors, e.g., patient response, etc. For example, the agent can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

The amount of the agent administered can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is within the level of skill in the art.

Methods of Treatment

The present disclosure also includes methods of treatment of a host in need of treatment for an autoimmune disorder with compounds and compositions of the present disclosure. "Treatment" as contemplated in the present disclosure, can include both palliative and preventative care, including alleviation and/or prevention of symptoms, slowing or arresting progression of a disease, and/or preventing or delaying onset of a disease in a host. Methods of treatment include administration of a therapeutically effective amount of a composition including the IDAC compounds of the present disclosure, such as pharmaceutical compounds or vaccines of the present disclosure.

In embodiments, the present disclosure includes methods of treating an autoimmune disorder by administration to a subject in need of treatment for an autoimmune disorder a compound including an I-domain peptide having at least two modified lysine residues and at least two signal 1 moieties conjugated to the I-domain peptides via the modified lysine residues. In embodiments, the I-domain peptide includes an I-domain peptide of the present disclosure as described above, having between 2 and 20 modified lysine residues. In the methods of the present disclosure, the signal 1 moieties are selected from epitopes of peptides associated with autoimmune disorders, such as but not limited to epitopes of PLP, MOG, MBP (for MS or EAS), GAD, ZNT8, IA-2, insulin (for Type I diabetes), human cartilage gp-39, cartilage proteins MIA, type II collagen, and citrullinated proteins (for rheumatoid arthritis), and nucleosomal and Chromatin peptides (for lupus). In embodiments, the signal 1 moieties are conjugated to the modified I-domain peptides via a linker. The linker may include amino acid molecules, polymer molecules, and/or maleimido molecules.

Additional details regarding the compounds, pharmaceutical compositions, methods, and vaccines for treatment and/or prevention of autoimmune disorders of the present disclosure can be found in the Examples below. These and other embodiments of the present disclosure will be described in greater detail below.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and enable them to use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the present disclosure, in general, the following Examples describe some additional embodiments of the present disclosure. While embodiments of present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure Example I Introduction Potential drugs such as monoclonal antibodies (mAb) or small molecules that block signal 2 have been developed for treating autoimmune diseases, but these drugs may also suppress the general immune response and compromise the ability of the host to respond to pathogenic infections. To overcome the general suppression of immune systems, one approach is to modulate the activation of a subpopulation of T-cells that recognizes a specific antigen using a bifunctional peptide inhibitor (BPI). The BPI molecules are composed of an antigenic peptide for the specific disease conjugated to a cell adhesion peptide via a spacer (3-7). GAD-BPI, PLP-BPI, and CII-BPI molecules have been shown to induce immunotolerance in non-obese diabetes (NOD) (5), experimental allergic encephalomyelitis (EAE) (3, 4, 6, 7), and collagen-induced arthritis (CIA), respectively. The antigenic peptide is derived from epitope of the protein antigen responsible for the autoimmune disease, while the adhesion peptide is derived from either the sequence of LFA-1 (LABL) or ICAM-1 (cIBR1). The potential mechanism of action of BPI molecules is via simultaneous binding to MHC-II and ICAM-1 receptors on the surface of APC, respectively. The simultaneous binding to these two-target receptors prevents the translocation signal 1 and signal 2 molecular complexes and inhibits the formation of the immunological synapse. As a result, the BPI molecules suppress the generation of inflammatory T-cells and possibly stimulate the formation of suppressor or regulatory T-cells.

In this example, 1-domain-antigen conjugate (IDAC) molecules were designed as potential therapeutic agents for the treatment of multiple sclerosis (Table 1). An IDAC molecule was prepared by conjugating $PLP_{139-151}$ peptide via maleimide spacers to several lysine residues on the I-domain protein derived from the α-subunit of LFA-1 (FIG. 1). The 1-domain is the binding region of LFA-1 to ICAM-1, and it has been shown to interact with the D1 domain of ICAM-1 (8). Compared to the cell adhesion peptide LABL, the I-domain offers a unique divalent cation coordination site called metal ion-dependent adhesion site or MIDAS that interacts with the ICAM-1 D1 domain. One advantages of 1-domain over the peptide (LABL peptide) is that there are potential multiple conjugation sites on the I-domain. In this study, PLP-Cys-OH was conjugated to GMB-I-domain to give IDAC. The in vivo efficacy of IDAC was compared to negative control (PBS) and positive control (Ac-PLP-BPI-$NH_2$-2). Results show that IDAC can delay the onset of EAE compared to PBS and that IDAC strongly suppresses the progression of EAE.

Objectives of this example included characterizing the identity of I-domain-antigen conjugate (IDAC) and evaluation of the in vivo efficacy of IDAC in suppressing experimental autoimmune encephalomyelitis (EAE) in mouse model. The results below demonstrate that the I-domain delivers $PLP_{139-151}$ peptides to antigen-presenting cells (APC) and alters the immune system by simultaneously binding to ICAM-1 and MHC-II, blocking immunological synapse formation. IDAC was synthesized by derivatizing the lysine residues with maleimide groups followed by conjugation with PLP-Cys-OH peptide. Conjugation with PLP peptide does not alter the secondary structure of the protein as determined by CD. IDAC suppresses the progression of EAE while I-domain and GMB-I-domain could only delay the onset of EAE. As a positive control, Ac-PLP-BPI-$NH_2$-2 can effectively suppress the progress of EAE. The number of conjugation sites and the sites of conjugations in IDAC were determined using tryptic digest followed by LC-MS analysis. As detailed below, conjugation of I-domain with an antigenic peptide (PLP) resulted in an active molecule to suppress EAE in vivo.

Experimental Procedures

Materials

The amino acids used for peptide synthesis were purchased from Peptide International (Louisville, Ky.). GMBS (N-[γ-maleimidobutyryloxy]succinimide ester) was from Pierce (Rockford, Ill.). Sequence-grade modified trypsin was from Promega (Madison, Wis.). All other chemicals or solvents were of analytical grade or better.

Mice

The in vivo studies were carried out using female inbred SJL/J (H-$2^s$) mice purchased from Charles River Laboratories, Inc. (Wilmington, Mass.). The animals were housed under specific pathogen-free conditions at an American Association for Accreditation of Laboratory Animal Care (AAALAC)-approved animal facility at The University of Kansas. The protocol for working mice had been approved by the Institutional Animal Care and Use Committee (IACUC).

Peptide Synthesis

The sequences of peptides used in the present study are listed in Table 1. The standard Fmoc solid-phase peptide chemistry was used to synthesize all peptides on PEG-PS resin (Applied Biosystems, Foster City, Calif.) with the automated peptide synthesis system (Pioneer™ perspective Biosystems, Framingham, Mass.). Peptide synthesis and purification were conducted according to our previously published method (4). All peptides were purified using semi-preparative $C_{18}$ reversed-phase HPLC, and the purity of each fraction from the preparative HPLC was determined by analytical HPLC. The pure fractions were pooled and lyophilized; the molecular weight of each peptide was confirmed by electrospray ionization mass spectrometry (M+H$^+$) (MW PLP-Cys-OH=1624.86; Ac-PLP-BPI-$NH_2$-2=3416.95).

Preparation of I-Domain

The LFA-1 I-domain protein was over-expressed, refolded, and purified as previously described (9). The protein purity, identity, and secondary structure were confirmed by SDS-PAGE, mass spectrometry, and far-UV circular dichroism (CD), respectively.

Synthesis of IDAC

As shown in FIG. 1, two steps are used to prepare the IDAC. The first is to modify the amino groups of the N-terminal and side-chain of lysine residues of I-domain by reacting them with N-[γ-maleimidobutyryloxy]succinimide ester (GMBS). This step introduces maleimide groups on the I-domain to generate the GMB-I-domain. The second step is to conjugate the thiol group on the Cys residue of PLP-Cys-OH peptide to the maleimide groups on the I-domain to give IDAC.

Step 1:

To a total of 20 mg of I-domain solution, a tenfold molar excess of freshly prepared GMBS (2.71 mg) solution in DMSO (0.5 mL) was added dropwise followed by stirring of the mixture for 1 h at 24° C. Then, the reaction mixture was subjected to purification through a Superdex 75 column to isolate the GMB-I-domain. The desired GMB-I-domain and the excess GMBS were eluted with PBS containing 10 mM $MgSO_4$. The fractions containing the GMB-I-domain were collected and concentrated by ultrafiltration. Modification on the I-domain using this method produced 3-10 maleimide groups per I-domain as determined by electrospray ionization mass spectrometry (ESI-MS).

Step 2:

The conjugation reaction of the PLP-Cys-OH peptide to GMB-I-domain was carried out at pH 8.5 to give IDAC. To a solution containing 10 mg of GMB-I-domain, a 15 molar excess of PLP-Cys-OH dissolved in PBS was added dropwise. During addition of the peptide, the pH was constantly monitored and adjusted to 8.5. During the reaction, the final concentration of the protein was 2.0 mg/mL. The reaction was carried out for 1 h at 24° C. with constant stirring. After the reaction was completed, the solution pH was readjusted to pH 7.4. The resulting IDAC reaction mixture purified using a Superdex 75 column. The fractions belonging to the IDAC were collected and concentrated by ultrafiltration. IDAC contained 1 to 5 peptide molecules per I-domain molecule as determined by ESI-MS. The purity of the IDAC was confirmed by SDS-PAGE gel and size-exclusion chromatography. The CD spectrum of the IDAC was compared with that of the parent I-domain protein.

LC-ESI-MS Analysis of Intact Protein

To obtain intact protein masses, pure protein samples obtained after SEC were analyzed by LC ESI-Q-TOF MS. HPLC separations were performed with a Water Acquity solvent delivery system using a binary gradient of solvent A composed of 98.92:1:0.08 $H_2O$/acetonitrile/formic acid (vol/vol/vol) and solvent B containing 98.92:1:0.08 acetonitrile/$H_2O$/formic acid (vol/vol/vol). Approximately 10 pmol of the sample was loaded onto a $C_4$ reversed-phase HPLC column (1×50 mm, 5 μm, 300 Å; Micro-Tech Scientific, Vista, Calif.) with a linear gradient from 20% to 60% B in 10 min with a flow rate of 20 μL/min followed by a wash and re-equilibration step. Furthermore, the HPLC system was coupled online to the electrospray source of a Q-TOF-2 mass spectrometer (Micromass UK Ltd., Manchester, U.K.). Mass spectra were acquired with instrument cone voltage 35 eV, collision energy 20 eV with Ar in the collision cell. The instrument was set up in positive reflector mode with a scan time of 5 s and in the mass range m/z 700-3000. The instrument was calibrated using NaI. The ion chromatograms were processed to obtain the molecular weights of the modified peptides using MaxEnt1 in the MassLynx v 4.1 software (Micromass UK Ltd.).

Gel Electrophoresis

The pure protein solution (i.e., 100 μg of IDAC or I-domain) obtained after SEC separation was mixed with a 4×Tris-glycine SDS sample buffer containing no reducing agent and loaded into 1.5-mm-thick 10-well NuPAGE® Novex 4-12% Bis-Tris gradient gels. After running gel electrophoresis at 150 V for 70 min, the gels were stained with 0.25% Coomassie blue R250 solution (10% acetic acid/50% ethanol/40% water) for 30 min followed by destaining (10% acetic acid/25% ethanol/65% water) until the bands were visible and the background was clear.

In-Gel Trypsin Digestion

A standard in-gel protein digestion protocol was followed as described elsewhere (10). Briefly, protein bands were excised from the gel and were digested with trypsin at an enzyme-to-substrate ratio of 1:25 (w/w) at 37° C. overnight. To stop the digestion, 2 μL of glacial acetic acid was added to each sample.

LC-MS/MS Analysis of Tryptic-Digest Products

The products of tryptic digest from 1-domain and IDAC were introduced onto a capillary reversed-phase HPLC and CID spectra from peptides were obtained with a hybrid tandem hybrid ion trap/ion cyclotron resonance mass spectrometer (LTQFT ThermoFinnigan, Bremen, Germany) under conditions described previously (11). The experimental raw data were processed using Bioworks software (Thermo, version 2.0) to create an MS/MS peak list in a DTA format. Protein sequence mapping was performed using Sequest, Mascot (Matrix Science, version 2.2), and XITandem (www.thegpm.org) algorithms with a fragment ion mass tolerance of 0.20 Da and a parent ion tolerance of 1.2 Da. Amino groups of lysine residues and protein N-terminus were considered to be modified with maleimide linker moiety+dipeptide (Phe-Cys). The chemical composition of the modification for IDAC is $C_{20}H_{23}N_3O_6S$, delta monoisotopic mass 433.1308 and its maleimide hydrolysis product is $C_{20}H_{25}N_3O_7S$, delta monoisotopic mass 451.1413. Protein modification sites identified by tryptic digestion of the final construct are based on the assumption that trypsin cleaves at the carboxyl side of the lysine residue ($^{12}K$) of the peptide PLP-Cys-OH leaving a construct peptide of FC . . . linker . . . I domain tryptic peptide (see FIG. 1 step 2). Scaffold software (Proteome Software Inc., version 2.06) was used to combine and validate MS/MS-based peptide identifications. Peptide identifications with greater than 50% probability as specified by the Peptide Prophet algorithm (12) were accepted for reporting protein coverage.

Induction and Suppression of EAE

Disease Stimulation:

Female inbred SJL/J mice, 5-7 weeks old, were randomly divided into different groups. All mice were immunized with $PLP_{139-151}$ in Freund's complete adjuvant (CFA) to induce EAE, as reported previously (3, 4). The PLP/CFA emulsion (50 μL per site) was administered to four separate regions above the shoulder and on the flanks. In addition, 200 ng of pertussis toxin (List Biological Laboratories Inc., Campbell, Calif.) was injected intraperitoneally on day 0 and 2.

In Vivo Study:

After disease stimulation, one group of mice received intravenous (i.v.) injections of 26 nmol/injection/day of the conjugate IDAC on days 4 and 7. The second and third groups of mice received i.v. injections of 100 nmol/injection/day of Ac-PLP-BPI-$NH_2$-2 and 100 microliter of PBS, respectively, on days 4, 7, and 10. The animals were weighed and observed daily. Disease progression was evaluated observed using a blinded method as reported previously (3, 4). The clinical scores were rated using the following scale: 0—no clinical signs of disease; 1—tail weakness or limp tail; 2—paraparesis (weakness or incomplete paralysis of one or two hind limbs); 3—paraplegia (complete paralysis of two hind limbs); 4—paraplegia with forelimb weakness or paralysis; and 5—moribund or dead. Mice were euthanized once they were found to be moribund.

Statistical Analysis

Statistical differences among the groups in clinical disease scores were determined by calculating the average score for each mouse from the day of disease onset to day 20 by One-way Analysis of Variance followed by Fisher's least significant difference using StatView (SAS Institute, Cary, N.C.). Statistical differences among the groups in body weight were also analyzed in the same way. The presence of significant difference is denoted with p-values of <0.05 or <0.001.

Results

Synthesis and Characterization of IDAC

Figure 2B:
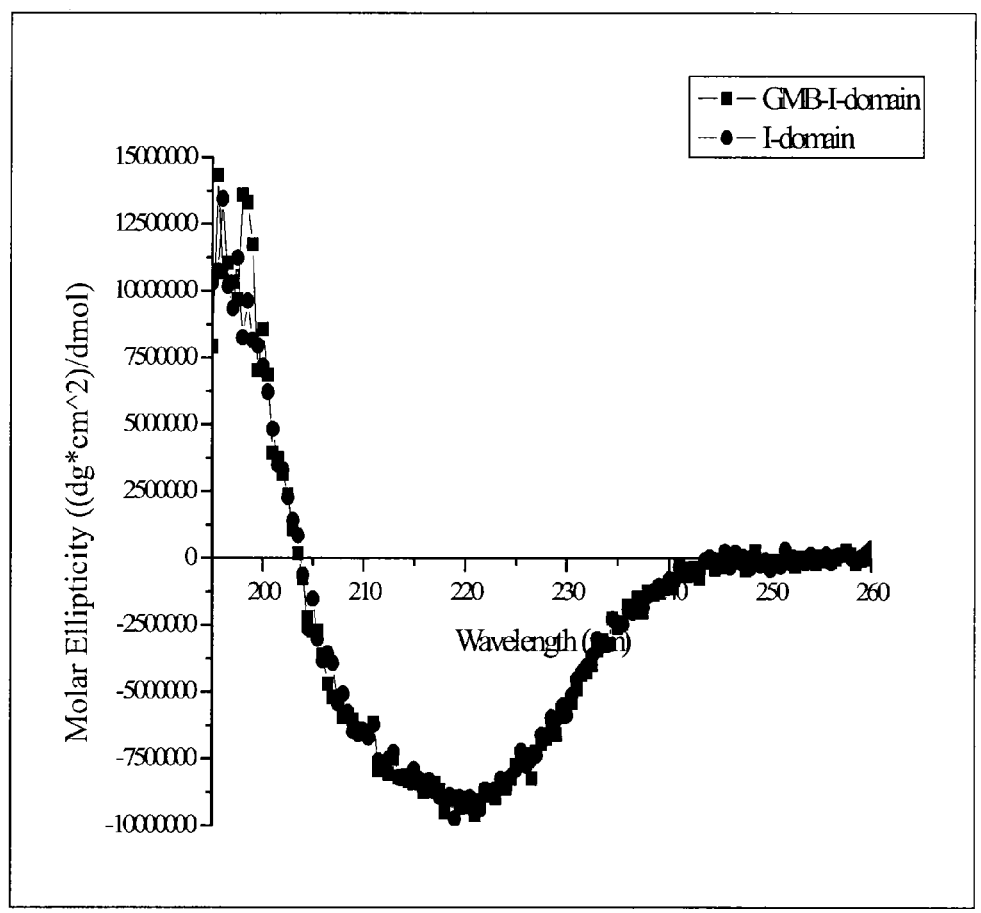

IDAC was prepared by conjugating the PLP-Cys-OH peptide to the N-terminus and side chain amino groups of the lysine residues in the I-domain (FIG. 1). Thus, the amino groups in the I-domain were reacted with the active N-hydroxysuccinimide (NHS) ester of GMBS to produce GMB-I-domain protein via a stable amide bond (Step 1, FIG. 1). The GMB-I-domain from the reaction mixture was purified from the excess GMBS using SEC (FIG. 2A). Comparison of CD spectra of GMB-I-domain and I-domain shows that they have similar spectra (FIG. 2B), indicating that adding of GMB groups does not alter the secondary structure of the GMB-I-domain.

The composition of pure GMB-I-domain was analyzed by liquid chromatography coupled online with ESI-MS. The charge deconvoluted MS spectrum shows three to nine γ-maleimidobutyryloxy (GMB) groups attached to the I-domain with following masses: 21,178 Da, 21,343 Da, 21,508 Da, 21,674 Da, 21,839 Da, 22,004 Da, and 22,169 Da (top panel, FIG. 2C). The differences in mass are 165 Da, which is consistent for a sequential addition of GMB group. The first peak at 21,178 Da corresponds to the I-domain molecular weight conjugated to three GMB groups; therefore, the remaining peaks correspond to the I-domain with four to nine covalently linked GMB groups, respectively. The parent I-domain has a MW of 20,682 (bottom panel, FIG. 2C) and it was not found in the MS spectrum of GMB-I-domain (top panel, FIG. 2C).

Figure 2D:
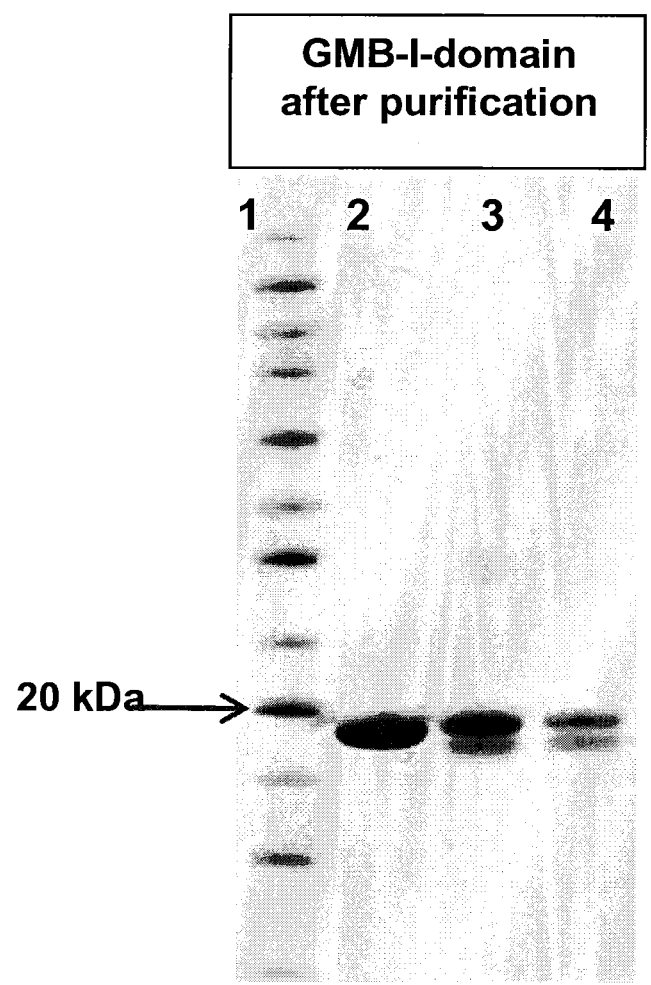

Along with the desired GMB-I-domain peak, there are corresponding peaks with a mass increase of 18 and 36 Da found in the MS spectra (top panel, FIG. 2C). These peaks correspond to the hydrolysis of maleimide groups or maleic acid derivatives, which are attached to the I-domain (13). The MS data correlate with the SDS-PAGE image of the isolated product of GMB-I-domain from SEC, which shows two bands on lane 4 in FIG. 2D. These two bands are from the desired maleimide and maleic acid derivatives of I-domain with different electrophoretic mobility. Before purification, the reaction mixture (lane 3, FIG. 2D) shows three bands while the control I-domain (lane 2, FIG. 2D) produces only one band. The formation of maleimide hydrolysis products is increased upon storage; thus, it is important that the GMB-I-domain be used within 48 h after SEC purification.

Conjugation of PLP-Cys-OH Peptide to GMB-I-Domain

Figure 3A:
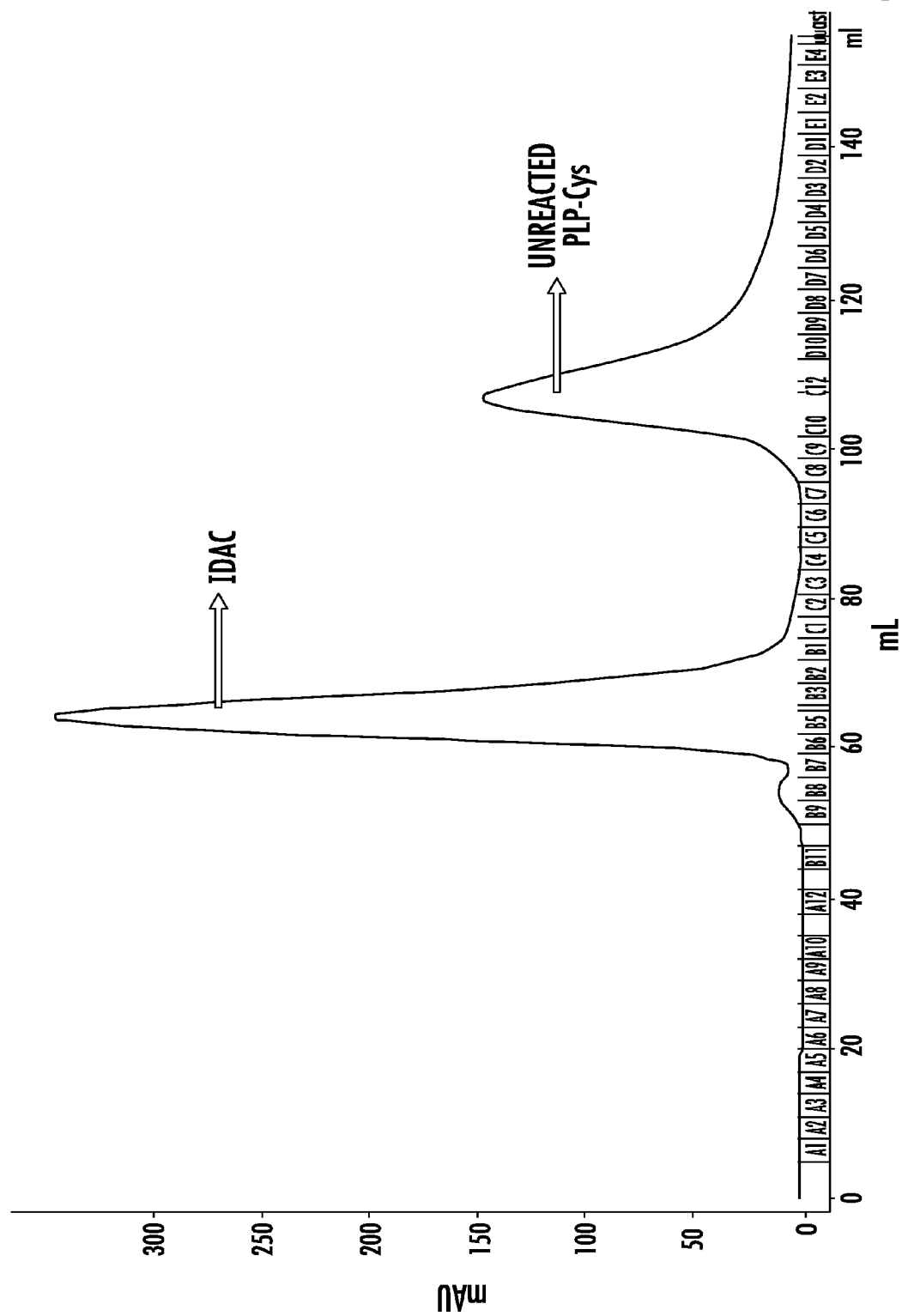
FIGS. 3A-3D illustrate purification and characterization of IDAC by SEC, SDS-PAGE, MS, and CD.
Figure 3B:
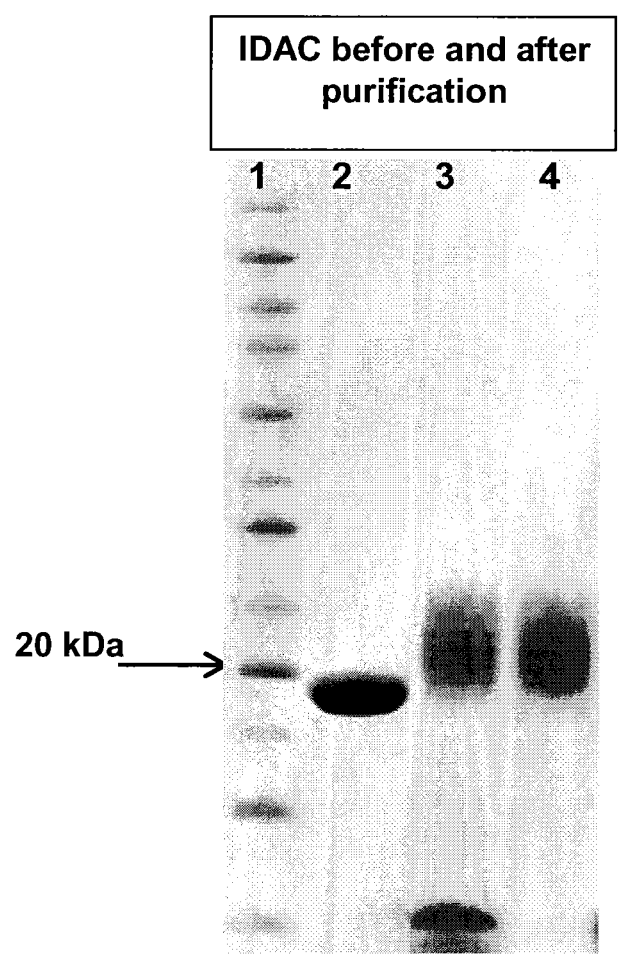

PLP-Cys-OH is a peptide that contains $PLP_{139-151}$ sequence with an additional cysteine amino acid at the C-terminus with an open carboxylic acid (Cys-OH). PLP-Cys-OH was reacted with GMB-I-domain at pH 8.5 to prepare IDAC. In this case, the peptide conjugation is via nucleophilic attack of the maleimide groups on the GMB-I-domain by the thiol group of the Cys residue on the peptide (Step 2, FIG. 1). Crude products were purified with SEC; the desired IDAC could be easily separated from PLP-Cys-OH (FIG. 3A). The pure fractions of IDAC were pooled and concentrated. The crude and purified product was analyzed by SDS-PAGE gel against the parent I-domain (FIG. 3B). As expected, the parent I-domain shows one single band with lower molecular weight than the conjugates (lane 2, FIG. 3B). The gel of the crude product illustrates the presence of IDAC along with lower MW bands corresponding to PLP-Cys-OH (lanes 3, FIG. 3B). The gel of purified IDAC shows multiple bands, which have higher molecular weight than the parent I-domain and without the starting PLP-Cys-OH (lanes 4, FIG. 3B). The multiple bands on IDAC were due to various levels of peptide conjugates.

Figure 3C:
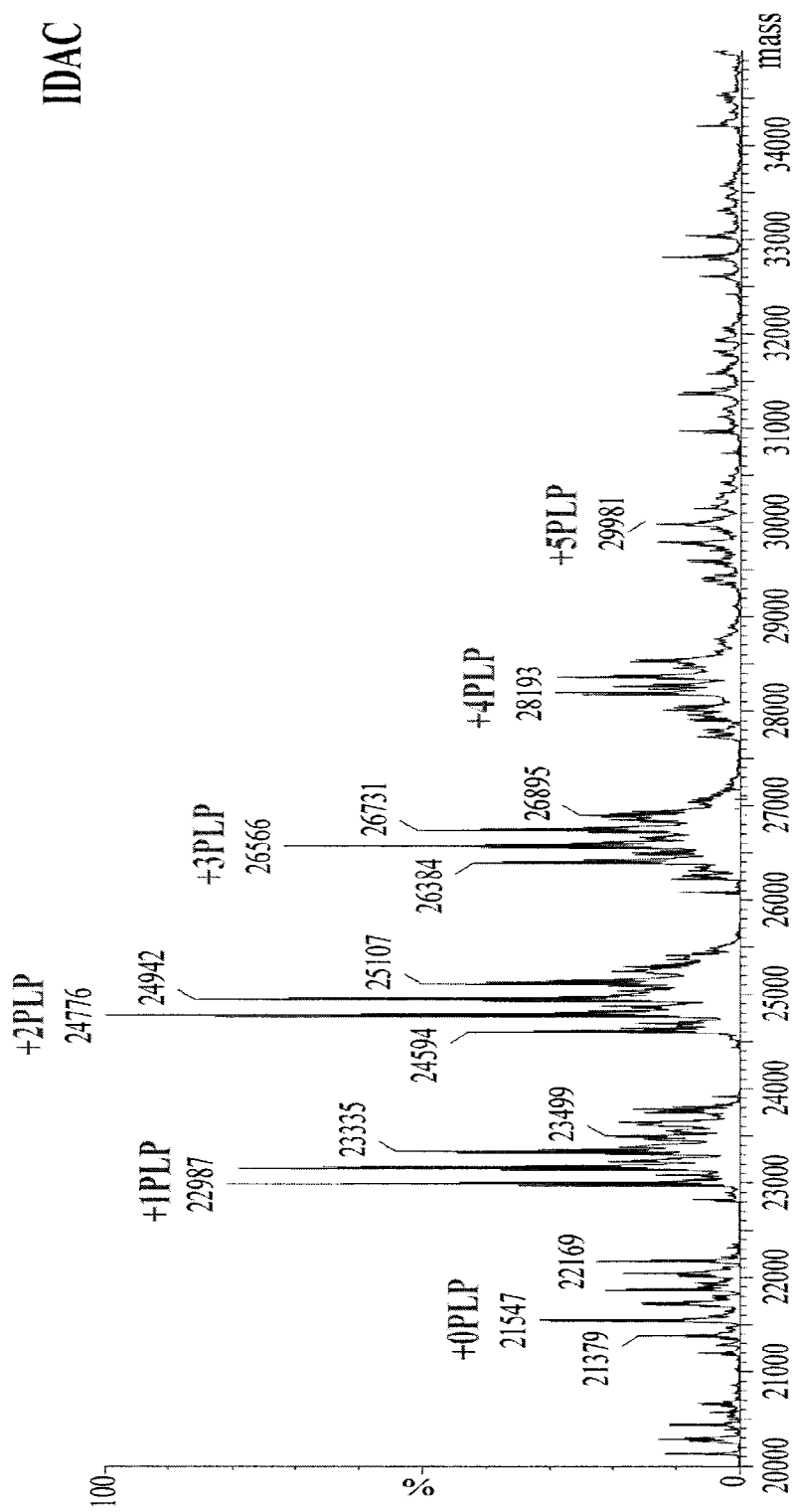
Figure 3D:
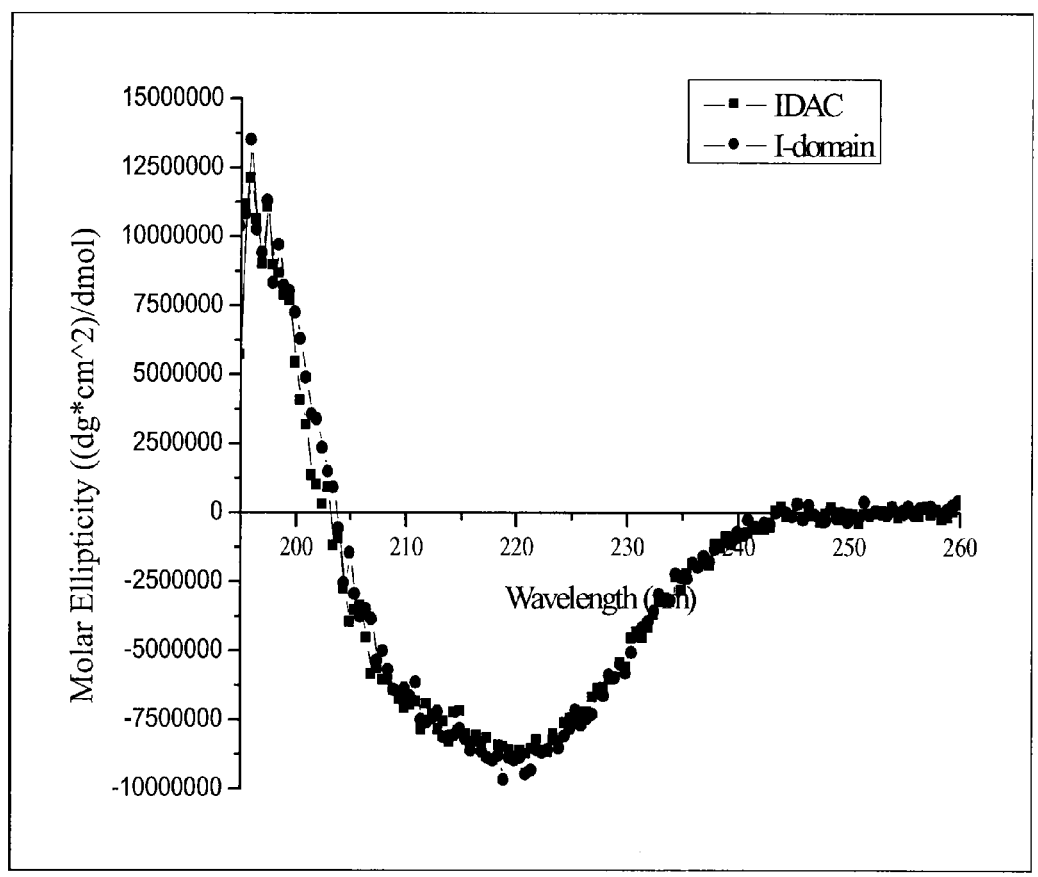
Figure 4:
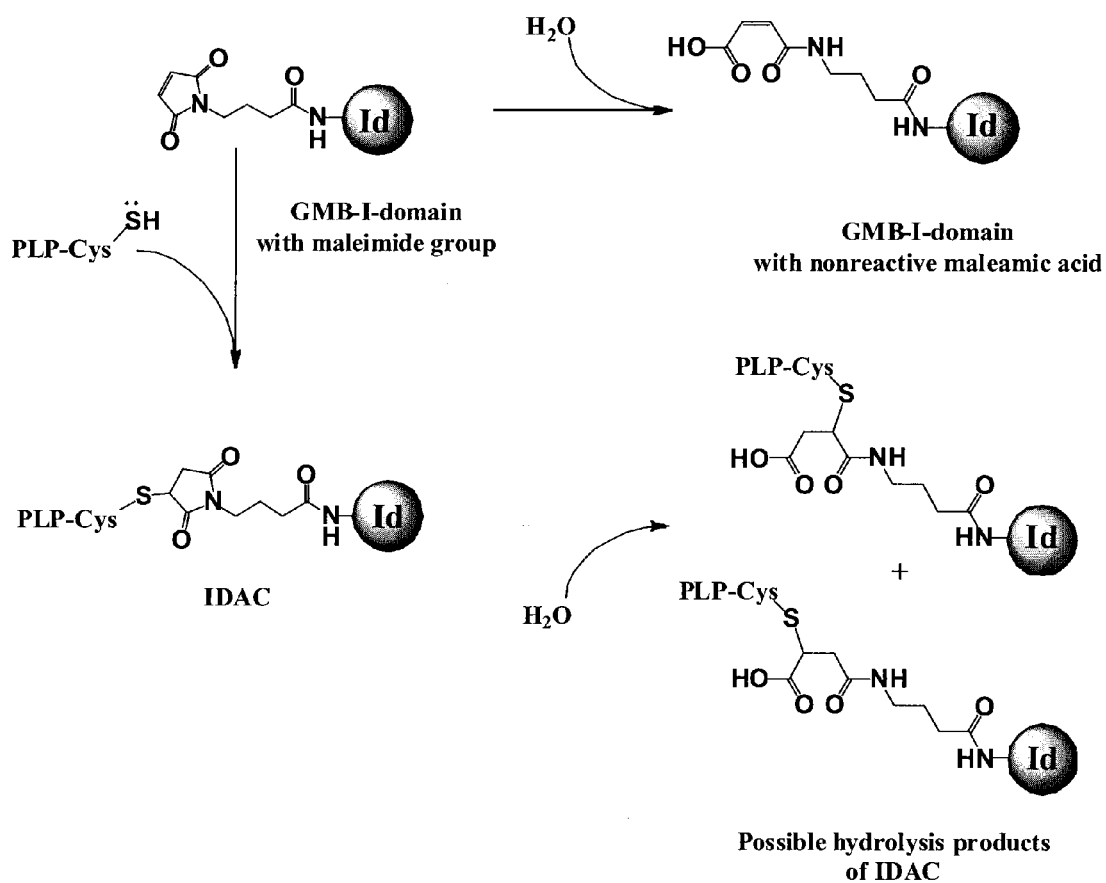
FIG. 4 illustrates a schematic representation of possible hydrolysis products of GMB-I-domain and IDAC.

The charge deconvoluted LC-MS data indicated that 0-5 PLP peptides were attached to the IDAC with an average of 2.5 PLP peptides per I-domain (FIG. 3C). Each subpopulation of peaks in the spectra of IDAC has various MW peaks due to the presence of different numbers of GMB groups, but the same number of PLP-Cys peptide attached to the I-domain. The complexity in each of the subpopulations arises from the hydrolysis products of maleimide FIG. 4 (13). The CD spectrum of each conjugate was similar to that of the parent I-domain protein (FIG. 3D), indicating that conjugation of PLP-Cys peptide to the I-domain preserves the native secondary structure of the protein.

Structural Analysis of IDAC

To investigate the structure of IDAC, peptide mapping using tryptic digestion and mass spectrometry was used to determine the location of PLP peptides on the I-domain protein. The assumptions are that the modified lysine residues on the I-domain cannot be cleaved by trypsin, and the cleavage product of the lysine residue that is attached to the PLP peptide can be used to identify the modified lysine residue on the I-domain. The modified peptide fragments were identified using LC-MS/MS. The PLP peptide contains a Lys residue (Lys12), which also could be hydrolyzed by trypsin to produce a dipeptide, Phe-Cys-OH, which is attached to maleimidobutyryloxy. The attached dipeptide has a molecular weight of 433.1307 Da for Phe-Cys-OH. In addition, we observed Phe-Cys-OH conjugated to the peptide fragment via the hydrolysis product of maleimide, which has 18.0106 Da molecular weight added. The comparison of LC-MS/MS data from tryptic-digest fragments of the conjugates is summarized in Table 2. The LC-MS/MS sequence coverage for IDAC was 99%, and a total of 15 modified tryptic peptides were identified from IDAC. All of the conjugation sites were partially modified, and the number of unmodified peptides dominated the search profile. These modified peptides were unique and were found in the mapping profiles of the conjugates but not in the parent I-domain profile. The experimental and the calculated mass values of the modified peptides were very close, with the average deviation being less than 0.1 Da.

Suppression of EAE by IDAC

Figure 6A:
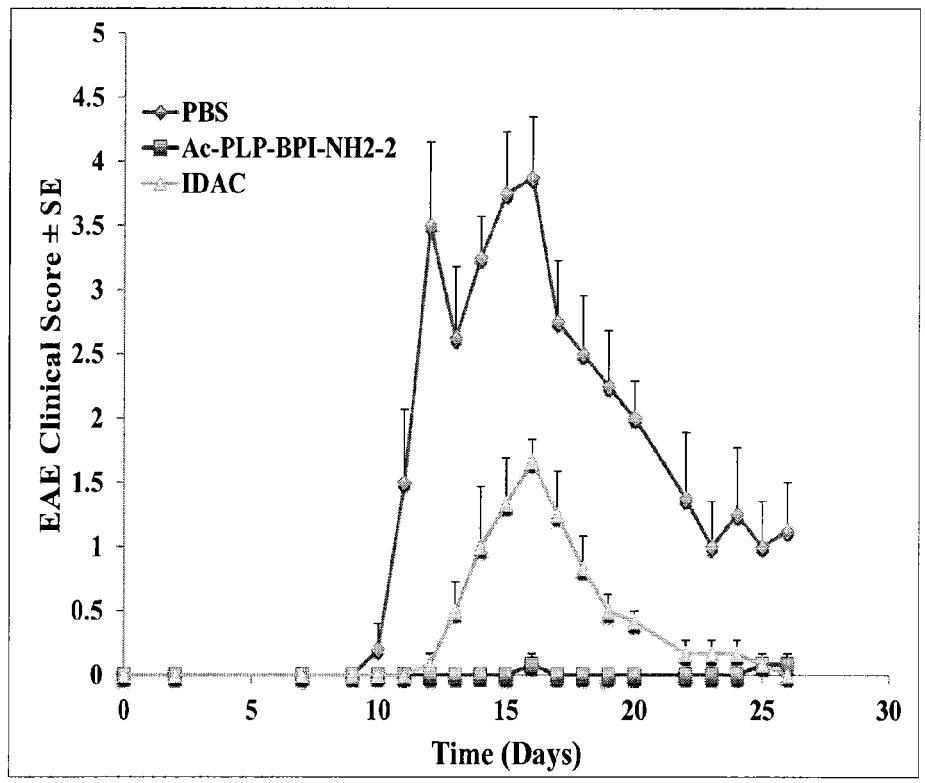
FIGS. 6A-6C are graphs illustrating the In vivo activity of IDAC, Ac-PLP-BPI-NH$_2$-2, and PBS in mouse EAE model. After immunization with PLP peptide in CFA, the mice received i.v. injections of 26 nmol/injection/day of the conjugate IDAC on days 4 and 7. For the Ac-PLP-BPI-NH$_2$-2 treatment group, the mice received i.v. injections of 100 nmol/injection/day of the peptide on days 4, 7, and 10. The control group was treated with PBS on days 4, 7, and 10. Disease progression was evaluated and graphed using clinical disease scores (6A), change in body weight (6B), and incidence of disease (6C). The results are expressed as the mean±S.E. (n≥6).
Figure 6B:
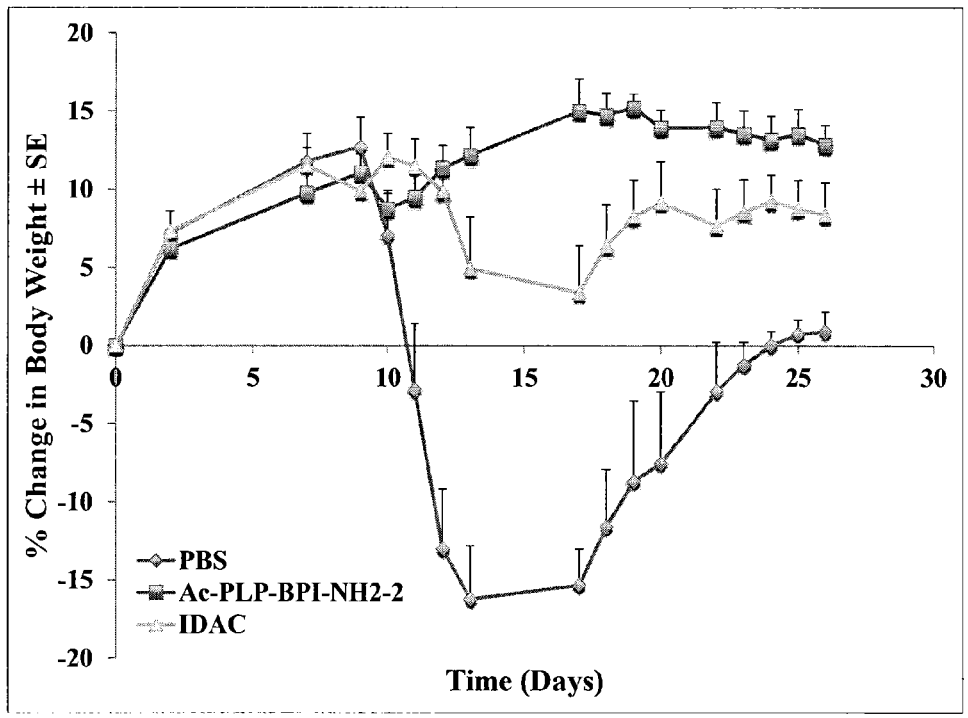
Figure 6C:
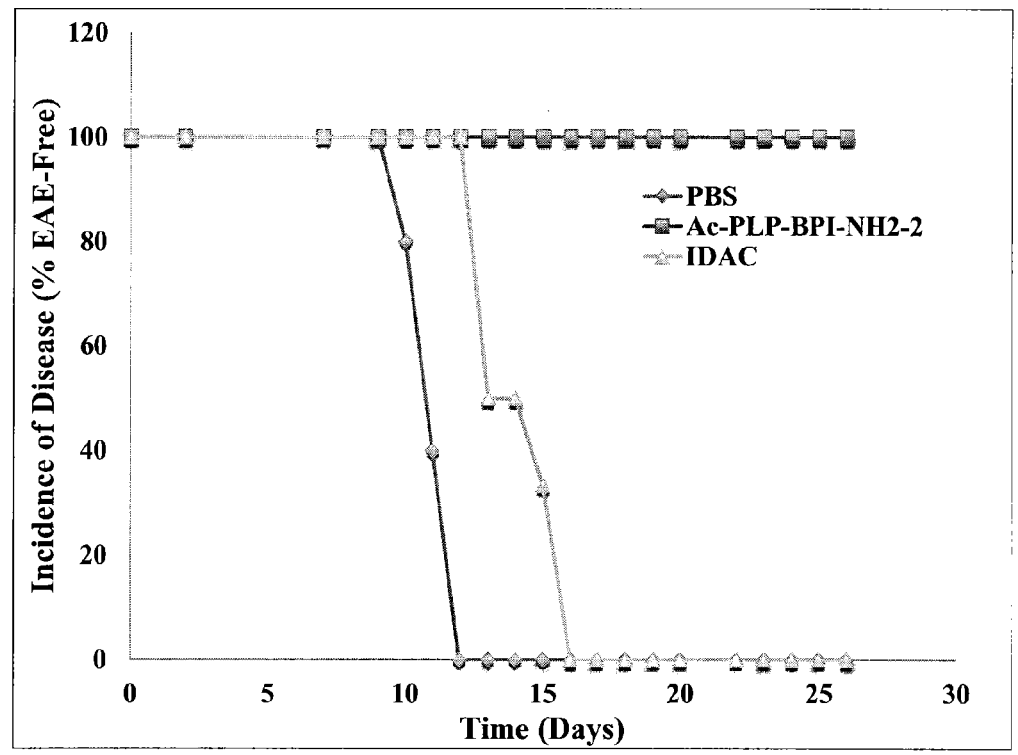

The clinical scores indicate that two injections of IDAC have significant efficacy to suppress the progress of EAE compared to those treated with PBS (p<0.0001, through days 12-17); however, three injections of Ac-PLP-BPI-NH$_2$-2 provide complete suppression of the disease (p<0.0001, through days 12-17) (FIG. 6A). The efficacy of IDAC is also reflected in the ability to prevent the changes of bodyweights of the mice significantly compared to PBS-treated mice (FIG. 6B). The disease incidence was delayed in the IDAC-treated mice compared to PBS-treated mice (p<0.0001, through days 12-24) and completely eliminated in Ac-PLP-BPI-NH$_2$-2-treated mice (p<0.0001, through days 12-24) (FIG. 6C).

Discussion

Patients with autoimmune diseases such as multiple sclerosis, rheumatoid arthritis, and psoriasis are currently being treated with protein-derived drugs such as monoclonal antibodies and peptide polymers, which modulate the immune system. Current treatments of multiple sclerosis patients include Copaxone® and Tysabri® as well as anti-inflammatory agents (e.g., corticosteroids, beta-interferon-1a, mitoxantrone). Some of the drugs for multiple sclerosis have been shown to have different side effects in patients, including the suppression of the general immune response, which can lead to undesirable pathogenic infections. Tysabri® is a monoclonal antibody that binds to the $α_4$-subunit of $α_4β_1$ and $α_4β_7$ integrins to block leukocyte adhesion and infiltration into CNS. Although this drug is effective, patients treated with Tysabri® were found to develop progressive multifocal leuko-encephalopathy (PML), a life-threatening complication in patients (14). PML was also observed in patients treated with Raptiva® (Efalizumab, CD11a mAb) for psoriasis; thus, this drug was withdrawn from the market (15, 16). Because Tysabri® and Raptiva® bind to integrins, these antibodies presumably also suppress signal 2 for T-cell activation in addition to blocking the cell adhesion. Blocking signal 2 of the immunological synapse formation suppresses the general activation of T-cells that can respond to pathogens such as JC virus that causes PML. Therefore, there is a need to discover a new way to suppress T-cell activation in an antigenic-specific manner without suppressing the general immune responses.

To address the issue of antigen specific disease suppression while preserving the immune system's ability to fight to foreign pathogens, the investigators of the present disclosure developed BPI molecules (GAD-BPI, PLP-BPI, and CII-BPI), (3-7) that were derived from antigenic peptides discovered by others (17-22). In parallel to BPI molecules, the investigators also developed IDAC molecule by conjugating several antigenic peptides to a single molecule of I-domain. Thus, at least one advantage of making IDAC is that the I-domain can be used to carry multiple copies of the antigenic peptides to improve the potency of the conjugate. In addition, the I-domain can also be utilized to carry multiple and different antigenic peptides to modulate different subpopulations of antigen-specific T-cells. Similar to BPI, IDAC conjugates are hypothesized to inhibit the immunological synapse formation during the process of T-cell activation by simultaneous binding of the PLP peptide and I-domain to MHC-II and ICAM-1, respectively, on APC. This simultaneous binding forms a bridge between the two receptors and eventually prevents the translocation and reorganization of signal 1 and signal 2.

In the present study, it was found that just two i.v. injections (26 nmol/injection) of IDAC inhibited the onset and progress of EAE more efficiently than PBS. Although the efficacy of IDAC appeared less than that of the BPI molecule, increasing the dose to 50 nmol/injection or more by keeping the frequency of injections the same may further suppress the disease. It is also possible to increase the frequency of administration (3-4 i.v. injections) by keeping the dose constant. One potential problem that arises while increasing the frequency of injections is a possibility of inducing anaphylactic shock.

The structural analyses of IDAC in the present example indicated the molecule contains an average of 2.5 peptide molecules per I-domain molecule. To determine the conjugation sites, both the conjugate and the parent I-domain were subjected to tryptic digestion followed by LC-MS/MS analysis. IDAC has a total of 15 lysine residues that are modified by PLP-Cys-OH peptide (Table 2). Previous studies by the present group showed that amidation and acetylation of the respective C- and N-termini of PLP peptide on BPI molecules enhanced the in vivo activity of BPI molecules. It has not yet been determined whether the amidation and acetylation of the C- and N-termini the PLP peptide have an effect on the conjugation sites and the in vivo efficacy of IDAC derivatives.

Figure 5A:
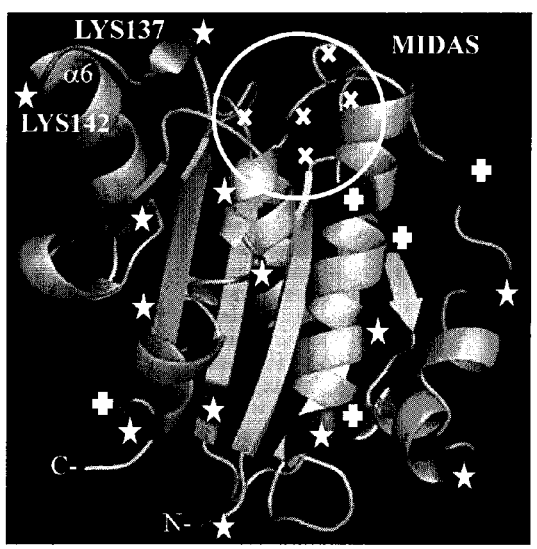
FIGS. 5A-5B illustrate a side view (5A) and top view (5B) showing the X-ray structure of I-domain (PDB code: 1ZON). The residues indicated with white stars show the location modified lysine sites, and the residues indicated with crosses show the location unmodified lysine sites in IDAC. The residues indicated with x's within the circle are those located at the MIDAS region (indicated by the circle). The N- and C-termini are labeled as N- and C-, respectively. The protein images were created using the PyMOL molecular graphics system version 1.4.1.
Figure 5B:
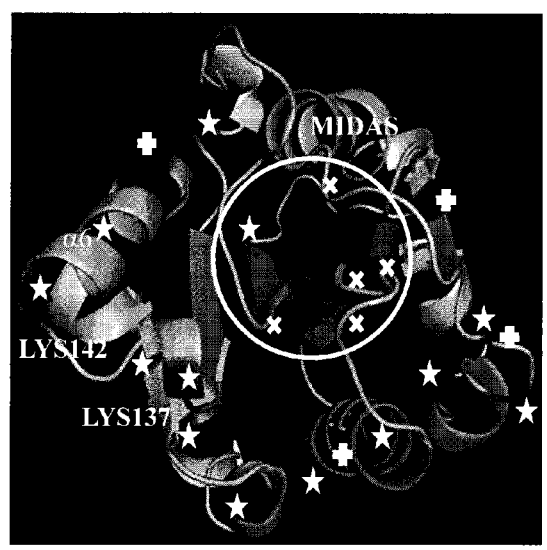

The locations of the modified and unmodified lysine residues are indicated in the structure of I-domain (FIG. 5). If the activity of IDAC is due to its simultaneous binding to ICAM-1 and MHC-II on the surface of APC, the most active conjugate should accommodate binding to these two receptors. It is known that the I-domain binds to ICAM-1 via its MIDAS region (circled area, FIG. 5). From the model derived from the X-ray structure, it was predicted that conjugation of PLP peptide at K137 and K142 would be the most probable sites to accommodate simultaneous binding of IDAC to MHC-II and ICAM-1. Good site(s) for peptide conjugation will also be determined using a single mutation of each Lys residue (i.e., K137 and K142) to a Cys residue followed by conjugation of PLP peptide. In this case, the peptide will be derivatized with a maleimide group. To illustrate, Lys142 can be mutated with Cys142 to give Cys142-I-domain. Then, Cys142-I-domain will be conjugated with PLP peptide to give PLP-Cys142-I-domain, and the in vivo activity of this new conjugate will be determined in the EAE mouse model. Using this method, we can pinpoint the conjugation site(s) that are important for the activity of the IDAC molecule. Since multiple sites of peptide conjugation are possible with IDAC; in such a case, multiple Cys mutations can be carried out on a single I-domain protein.

The present example demonstrates that IDAC has efficacy in inhibiting the progress of EAE in the mouse model. The presence of antigen spreading in autoimmune diseases such as multiple sclerosis may be addressed with multiple sites of conjugation with different peptides on I-domain protein. For example, antigenic peptides PLP, myelin basic protein (MBP), and myelin oligodendrocyte glycoprotein (MOG) can be simultaneously conjugated to I-domain to cover different subpopulations of T-cells. In such conditions, conjugation of each I-domain molecule with all the three-immunodominant epitopes may offer a unique approach for the treatment of multiple sclerosis.

TABLE 1A

List of embodiments of peptides and proteins used in the present disclosure

| Peptide/Protein | Sequence |
| --- | --- |
| I-domain | MGNVDLVFLFDGSMSLQPDEFQKILDFMKDVMKKLSNTSYQFAA VQFSTSYKTEFDFSDYVKRKDPDALLKHVKHMLLLTNTFGAINYV ATEVFREELGARPDATKVLIIITDGEATDSGNIDAAKDIIRYIIGIGKH FQTKESQETLHKFASKPASEFVKILDTFEKLKDLFTELQKKIY (SEQ ID NO: 1) |
| Ac-PLP-BPI-NH$_2$-2 | Ac-HSLGKWLGHPDKF-(AcpGAcpGAcp)$_2$-ITDGEATDSG-NH2 Ac-[(SEQ ID NO: 13)-(SEQ ID NO: 29)-(SEQ ID NO: 30)-NH$_2$] |
| PLP$_{139-151}$-Cys | HSLGKWLGHPDKFC (SEQ ID NO: 2) |
| IDAC | (HSLGKWLGHPDKFC)$_n$-linker-I-domain [Ac-(SEQ ID NO: 2)-linker-(SEQ ID NO: 1)] |
| Ac-PLP-Cys-NH$_2$ | Ac-HSLGKWLGHPDKFC-NH$_2$ [Ac-(SEQ ID NO: 2)-NH$_2$] |
| Ac-MOG$_{38-50}$Cys-NH$_2$ | Ac-GWYRSPFSRVVHLC-NH$_2$ [Ac-(SEQ ID NO: 4)-NH$_2$] |
| PLP40-60 and Cys modified | Ac-LTGTEKLIETYFSKNYQDYEY-NH$_2$ (SEQ ID NO: 5) and Ac-LTGTEKLIETYFSKNYQDYEYC-NH$_2$ (SEQ ID NO: 6) |
| MBP1-9 | ASQKRPSQR (SEQ ID NO: 7) |
| MBP30-40 | PRHRDTGILDSIGRF (SEQ ID NO: 8) |
| MBP83-99 | ENPVVHFFKNIVTPRTP (SEQ ID NO: 9) |
| MBP131-145 | ASDYKSAHKGFKGVD (SEQ ID NO: 10) |
| MBP140-154 | GFKGVDAQGTLSKIF (SEQ ID NO: 11) |
| GMB-I-domain | [N-(γ-maleimido)-1-oxybutyl]$_n$-I-domain [[N-(γ-maleimido)-1-oxybutyl]$_n$-SEQ ID NO: 1] |

Ac = Acetyl and Acp = Aminocaproic acid

TABLE 1B

List of other PLP and MOG peptides that can be signal-1 moieties

| SEQ ID NO | PLP/MOG Moiety Sequence | Organism | Sequence |
| --- | --- | --- | --- |
| 12 | PLP 139-151 | Homo sapiens | HCLGKWLGHPDKF |
| 13 | PLP 139-151 | Homo sapiens | HSLGKWLGHPDKF Note: C>S mutation |
| 14 | PLP 139-151 | Homo sapiens | HSLGKQLGHPDKF Note: C>S, W>Q mutation |
| 15 | PLP 139-151 | Homo sapiens | HSLGKLLGRPDKF Note: C>S, W>L, H>R mutation |
| 16 | PLP 139-151 | Homo sapiens | HSLGKWDGHPDKF Note: C>S, L>D mutation |
| 17 | PLP 89-106 | Homo sapiens | EGYTTGAVRQIFGDYKT |
| 18 | PLP 25-26 | Homo sapiens | CFFGVALFCGCGHEALTGTEKLIETYFSKNYQ |
| 19 | PLP 217-248 | Homo sapiens | GKVCGSNLLSICKTAEFQMTFHLFIAAFVGAA |
| 20 | PLP 257-276 | Homo sapiens | FMIAATYNFAVLKLMGRGTK |

TABLE 1B-continued

List of other PLP and MOG peptides that can be signal-1 moieties

| SEQ ID NO | PLP/MOG Moiety Sequence | Organism | Sequence |
|---|---|---|---|
| 21 | PLP 91-110 | Homo sapiens | FYTTGAVRQIFGDYKTTICG |
| 22 | PLP 43-64 | Homo sapiens | TEKLIETYFSKNYQDYEYLINV |
| 23 | PLP 104-117 | Homo sapiens | KTTICGKGLSATVT |
| 24 | PLP 56-70 | Homo sapiens | DYEYLINVIHAFQYV |
| 25 | PLP 178-191 | Homo sapiens | NTWTTCQSIAFPSK |
| 26 | MOG 8-21 | Homo sapiens | PGYPIRALVGDEAE |
| 27 | MOG 35-55 | Rat, mouse | MEVGWYRSPFSRVVHLYRNGK |
| 28 | MOG 97-108 | Homo sapiens | TCFFRDHSYQEE |

TABLE 2

Modification sites in IDAC (SEQ ID NO: 1) as determined by trypsin digestion and LC-MS/MS (all sequences are portions of SEQ ID NO: 1, with flanking aa's indicated in superscript)

| Modified peptide | Sequence | Modified sites |
|---|---|---|
| T1 | $^{1}$MGNVDLVFLFDGSMSLQPDEFQ$^{23}$K | M1 |
| T2-3 | $^{24}$ILDFMKDVM$^{33}$K | K29 |
| T4-5 | $^{34}$KLSNTSYQFAAVQFSTSY$^{52}$K | K34 |
| T6-7 | $^{53}$TEFDFSDYVK$^{63}$R | K62 |
| T8-9 | $^{64}$KDPDALL$^{71}$K | K64 |
| T9-10 | $^{65}$DPDALLKHV$^{74}$K | K71 |
| T12-13 | $^{96}$EELGARPDATKVLIIITDGEATDSGNIDAA$^{126}$K | K106 |
| T13-14 | $^{107}$VLIIITDGEATDSGNIDAAKDII$^{130}$R | K126 |
| T15-16 | $^{131}$YIIGIGKHFQT$^{142}$K | K137 |
| T16-17 | $^{138}$HFQTKESQETLH$^{150}$K | K142 |
| T18 | $^{151}$FASKPASEFV$^{161}$K | K154 |
| T18-19 | $^{151}$FASKPASEFVKILDTFE$^{168}$K | K161 |
| T19-20 | $^{162}$ILDTFEKL$^{170}$K | K168 |
| T20-21 | $^{169}$LKDLFTELQ$^{178}$K | K170 |
| T21-22 | $^{171}$DLFTELQK$^{179}$K | K178 |

Example 1 References (1) Schwartz, R. H. (2003) T cell anergy. *Annu. Rev. Immunol.* 21, 305-334.

(2) Salomon, B., and Bluestone, J. A. (1998) LFA-1 interaction with ICAM-1 and ICAM-2 regulates Th2 cytokine production. *J. Immunol.* 161, 5138-5142.

(3) Kobayashi, N., Kiptoo, P., Kobayashi, H., Ridwan, R., Brocke, S., and Siahaan, T. J. (2008) Prophylactic and therapeutic suppression of experimental autoimmune encephalomyelitis by a novel bifunctional peptide inhibitor. *Clin. Immunol.* 129, 69-79.

(4) Kobayashi, N., Kobayashi, H., Gu, L., Malefyt, T., and Siahaan, T. J. (2007) Antigen-specific suppression of experimental autoimmune encephalomyelitis by a novel bifunctional peptide inhibitor. *J. Pharmacol. Exp. Ther.* 322, 879-886.

(5) Murray, J. S., Oney, S., Page, J. E., Kratochvil-Stava, A., Hu, Y., Makagiansar, I. T., Brown, J. C., Kobayashi, N., and Siahaan, T. J. (2007) Suppression of type 1 diabetes in NOD mice by bifunctional peptide inhibitor: modulation of the immunological synapse formation. *Chem. Biol. Drug Des.* 70, 227-236.

(6) Ridwan, R., Kiptoo, P., Kobayashi, N., Weir, S., Hughes, M., Williams, T., Soegianto, R., and Siahaan, T. J. (2010) Antigen-specific suppression of experimental autoimmune encephalomyelitis by a novel bifunctional peptide inhibitor: structure optimization and pharmacokinetics. *J. Pharmacol. Exp. Ther.* 332, 1136-1145.

(7) Zhao, H., Kiptoo, P., Williams, T. D., Siahaan, T. J., and Topp, E. M. (2010) Immune response to controlled release of immunomodulating peptides in a murine experimental autoimmune encephalomyelitis (EAE) model. *J. Control Release* 141, 145-152.

(8) Shimaoka, M., Xiao, T., Liu, J. H., Yang, Y., Dong, Y., Jun, C. D., McCormack, A., Zhang, R., Joachimiak, A., Takagi, J., Wang, J. H., and Springer, T. A. (2003) Structures of the alpha L I domain and its complex with ICAM-1 reveal a shape-shifting pathway for integrin regulation. *Cell* 112, 99-111.

(9) Zimmerman, T., Oyarzabal, J., Sebastian, E. S., Majumdar, S., Tejo, B. A., Siahaan, T. J., and Blanco, F. J. (2007)

ICAM-1 peptide inhibitors of T-cell adhesion bind to the allosteric site of LFA-1. An NMR characterization. *Chem. Biol. Drug Des.* 70, 347-353.
(10) Speicher, K., Kolbas, O., Harper, S., and Speicher, D. (2000) Systematic analysis of peptide recoveries from in-gel digestions for protein identifications in proteome studies. *J. Biomol. Tech.* 11, 74-86.
(11) Ikehata, K., Duzhak, T. G., Galeva, N. A., Ji, T., Koen, Y. M., and Hanzlik, R. P. (2008) Protein targets of reactive metabolites of thiobenzamide in rat liver in vivo. *Chem. Res. Toxicol.* 21, 1432-1442.
(12) Keller, A., Nesvizhskii, A. I., Kolker, E., and Aebersold, R. (2002) Empirical statistical model to estimate the accuracy of peptide identifications made by MS/MS and database search. *Anal. Chem.* 74, 5383-5392.
(13) Partis, M. D., Griffiths, D. G., Roberts, G. C., and Beechey, R. B. (1983) Cross-linking of protein by omega-maleimido alkanoyl N-hydroxysuccinimido esters. *J. Protein Chem.* 2 263-277.
(14) Tan, C. S., and Koralnik, I. J. (2010) Progressive multifocal leukoencephalopathy and other disorders caused by JC virus: clinical features and pathogenesis. *Lancet Neurol.* 9, 425-437.
(15) Carson, K. R., Focosi, D., Major, E. O., Petrini, M., Richey, E. A., West, D. P., and Bennett, C. L. (2009) Monoclonal antibody-associated progressive multifocal leucoencephalopathy in patients treated with rituximab, natalizumab, and efalizumab: a Review from the Research on Adverse Drug Events and Reports (RADAR) Project. *Lancet Oncol.* 10, 816-824.
(16) Pugashetti, R., and Koo, J. (2009) Efalizumab discontinuation: a practical strategy. *J. Dermatolog. Treat.* 20, 132-136.
(17) Blanchfield, J. L., and Mannie, M. D. (2010) A GMCSF-neuroantigen fusion protein is a potent tolerogen in experimental autoimmune encephalomyelitis (EAE) that is associated with efficient targeting of neuroantigen to APC. *J. Leukoc. Biol.* 87, 509-521.
(18) Ni, J., Zhu, Y. N., Zhong, X. G., Ding, Y., Hou, L. F., Tong, X. K., Tang, W., Ono, S., Yang, Y. F., and Zuo, J. P. (2009) The chemokine receptor antagonist, TAK-779, decreased experimental autoimmune encephalomyelitis by reducing inflammatory cell migration into the central nervous system, without affecting T cell function. *Br. J. Pharmacol.* 158, 2046-2056.
(19) Wang, C., Gold, B. G., Kaler, L. J., Yu, X., Afentoulis, M. E., Burrows, G. G., Vandenbark, A. A., Bourdette, D. N., and Offner, H. (2006) Antigen-specific therapy promotes repair of myelin and axonal damage in established EAE. *J. Neurochem.* 98, 1817-1827.
(20) Falk, K., Rotzschke, O., Santambrogio, L., Dorf, M. E., Brosnan, C., and Strominger, J. L. (2000) Induction and suppression of an autoimmune disease by oligomerized T cell epitopes: enhanced in vivo potency of encephalitogenic peptides. *J. Exp. Med.* 191, 717-730.
(21) Luca, M. E., Kel, J. M., van Rijs, W., Wouter Drijfhout, J., Koning, F., and Nagelkerken, L. (2005) Mannosylated PLP(139-151) induces peptide-specific tolerance to experimental autoimmune encephalomyelitis. *J. Neuroimmunol.* 160, 178-187.
(22) Meiron, M., Zohar, Y., Anunu, R., Wildbaum, G., and Karin, N. (2008) CXCL12 (SDF-1 alpha) suppresses ongoing experimental autoimmune encephalomyelitis by selecting antigen-specific regulatory T cells. *J. Exp. Med.* 205, 2643-2655.

Example 2

A criticism of current therapies for multiple sclerosis (MS) is that they do not target the cause of MS but rather suppress the general immune system, leading to potential serious side effects. Therefore, there is a need to investigate a new and more specific way to control the immune response generated in an autoimmune disease such as MS without suppressing the general immune response.

The present example describes a novel way to deliver antigenic peptides to antigen presenting cells (APC) to control the activation of a subpopulation of T cells specific to a particular autoimmune disease. Previously, a cell adhesion peptide was conjugated to an antigenic peptide to make bifunctional peptide inhibitors (BPI) with the hypothesis that the BPI molecules target the APC to shift the activation of T cells from an inflammatory to a regulatory phenotype[7-9]. Previously, BPI molecules such as PLP-BPI, GAD-BPI, CII-BPI have been shown to successfully suppress the progression of autoimmune diseases such as MS, type 1 diabetes, and rheumatoid arthritis, respectively, in animal models[7-10]. It was proposed that BPI molecules bind simultaneously to the major histocompatibility complex class II (MHC-II) and ICAM-1 on APC to block the completion of immunological synapse formation at the interface of T cell-APC and alter T cell differentiation from inflammatory to regulatory[7-10]. In the case of PLP-BPI, it is a conjugate between an antigenic peptide ($PLP_{139-151}$) and a cell adhesion peptide (LABL), derived from the I-domain of lymphocyte function-associated antigen 1 (LFA-1) and tethered together by a linker molecule. Unfortunately, BPI molecules can deliver only one antigenic peptide at a time and cannot deliver multiple antigens when antigenic spreading has occurred. It would also be useful to simultaneously deliver multiple antigens to APC to overcome the problem of antigenic spreading in a particular autoimmune disease.

The present example describes development of I-domain antigen conjugate (IDAC) molecules derived from the I-domain protein and conjugated with multiple proteolipid protein (PLP) peptides to treat experimental autoimmune encephalomyelitis (EAE) in an animal model using prophylactic and vaccine-like delivery methods. The I-domain is derived from a binding region of LFA-1, which interacts with the first domain (D1) of ICAM-1[11]. Because the I-domain has multiple lysine residues, several PLP peptides can be conjugated to one molecule of the I-domain. In this study, IDAC-1 and IDAC-3 molecules were synthesized by conjugating PLP-Cys-OH and Ac-PLP-Cys-$NH_2$ peptides, respectively, to several lysine groups of the I-domain. The purified IDAC molecules were characterized with mass spectrometry and circular dichroism (CD) spectroscopy, and their efficacies were evaluated in the EAE mouse model and compared to positive controls (i.e., PLP-BPI and PLP-clBR) and negative controls (i.e., PBS, I-domain, GMB-I-domain). In both prophylactic and vaccine-like delivery methods, IDAC molecules effectively suppressed EAE compared to PBS. The cytokine production data suggest that IDAC molecules stimulate the proliferation of regulatory and suppressor cells.

Materials & Methods

Animals

SJL/J female mice were purchased from Charles River Laboratories, Inc. (Wilmington, Mass.) and subsequently housed under specific pathogen-free conditions at the animal facility at The University of Kansas approved by the Association for Assessment and Accreditation of Laboratory Animal Care (AAALAC). All experimental procedures using live mice were approved by the Institutional Animal Care and Use Committee (IACUC) at The University of Kansas.

Peptide Synthesis

All peptides used in this study (Table 1, below) were synthesized using a 9-fluorenylmethyloxycarbonyl-protected solid-phase peptide chemistry on an automated peptide synthesizer (Pioneer; Perceptive Biosystems, Framingham, Mass.). The peptides along with the protecting group were removed from the resin using trifluoroacetic acid (TFA) in the presence of appropriate scavengers. The crude peptides were purified using semi-preparative reversed-phase high-performance liquid chromatography (RP-HPLC) with a C18 column. A gradient method was used for purification with solvent A (94.9% water, 5% acetonitrile, and 0.1% trifluoroacetic acid) and solvent B (100% acetonitrile). HPLC with an analytical C18 column was used to determine the peptide purity (>96%). The identity of the peptides was confirmed using matrix-assisted laser desorption/ionization time-of-flight (MALDI-TOF) mass spectrometry.

I-Domain Preparation

The I-domain protein was over-expressed, refolded, and purified as previously described[12]. The identity, purity, and secondary structure of the protein were confirmed by mass spectrometry, SDS-PAGE, and CD, respectively.

Synthesis of IDAC-1 and -3

N-[γ-maleimidobutyryloxy]succinimide ester (GMBS) was first reacted at a tenfold molar excess with the free lysine residues of the 1-domain (2 mg/ml) for 1 h in PBS to generate GMB-I-domain. Subsequent purification of the reaction mixture was done using size-exclusion chromatography (SEC). Then, the thiol group on the Cys residue of PLP-Cys-OH and Ac-PLP-Cys-$NH_2$ peptides was reacted at a 15-molar excess with the newly formed maleimide groups on the GMB-I-domain (2 mg/ml) at pH 8.5 to give IDAC-1 and -3, respectively. After a 1-hour reaction, the pH of the solution was adjusted to 7.4, and the resulting mixture was purified using SEC. The purity, identity, and conformation of IDAC-1 and -3 were determined using SDS-PAGE, mass spectrometry, and CD, respectively.

Induction of EAE and Efficacy Studies

Six-to-eight week old SJL/J female mice were immunized subcutaneously with 200 µg $PLP_{139-151}$ peptide in a 0.2 ml emulsion consisting of equal volumes of PBS and complete Freund's adjuvant (CFA) containing killed *mycobacterium tuberculosis* strain H37RA at a final concentration of 4 mg/ml (Difco, Detroit, Mich.). The PLP/CFA emulsion was administered to regions above the shoulder and the flanks (total of 4 sites, 50 µl at each injection site). In addition, 200 ng of pertussis toxin was injected intraperitoneally on the day of immunization (day 0) and 2 days post-immunization.

The mice then received either intravenous or subcutaneous injections of IDAC (10 or 26 nmol/injection) or peptides (100 nmol/injection for Ac-PLP-BPI-$NH_2$-2 or 50 nmol/injection/mouse for Ac-PLP-cIBR1-$NH_2$). The prophylactic disease suppression was carried out with subcutaneous or intravenous injections of IDAC molecules on days 4 and 7, or BPI molecules on days 4, 7, and 10. Mice receiving vaccine-like treatment were given subcutaneous injections of IDAC and BPI molecules at 11, 8, and 5 days prior to the induction of disease. As negative controls, mice were treated with PBS, 1-domain, and GMB-I-domain. Disease progression was evaluated by monitoring the change in weight of the mice and clinical scoring based on the severity of nerve damage ranging from 0 to 5: 0—no clinical symptoms of disease; 1—tail weakness or limp tail; 2—paraparesis (weakness or partial paralysis of one or two hind limbs); 3—paraplegia (complete paralysis of two hind limbs); 4—paraplegia with forelimb weakness or paralysis; 5—moribund (at this point, the affected mice were euthanized).

Determination of Cytokine Levels In Vitro

Representative spleens for each group (IDAC-3 or PBS) from Study 2 were harvested from female SJL/J (H-$2^s$) mice on days 13 and 35. Splenocytes were dispersed by gently smashing the spleen using the coarse portion of a 1 ml syringe in a petri dish containing RPMI 1640 medium (10% FBS, 0.05M BME). The cells were then filtered through a 40 micrometer strainer. After centrifugation, the red blood cells were lysed using "ACK lysis buffer," and the remaining white blood cells were washed three times with medium. Splenocytes ($5 \times 10^6$ cells/ml) were cultured in parallel in the presence of 20 µM PLP and blank RPMI medium. Supernatants were collected at a 72 h time-point for the measurement of cytokine levels. The samples were then analyzed using a fully quantitative ELISA-based Q-Plex™ Mouse Cytokine-Screen (Quansys Biosciences, Logan, Utah).

Statistical Analysis

Statistical differences among the groups in clinical disease scores were determined by calculating the average score for each mouse from day 12 to day 17 by one-way analysis of variance followed by Fisher's least significant difference. Statistical differences in body weight among groups were also analyzed in the same fashion, but from day 12 to day 24. Comparison of cytokine concentrations was also performed by one-way analysis of variance. All analyses were performed using StatView (SAS Institute, Cary, N.C.).

Results

Synthesis and Characterization of IDAC-1 and -3

Figure 7A:
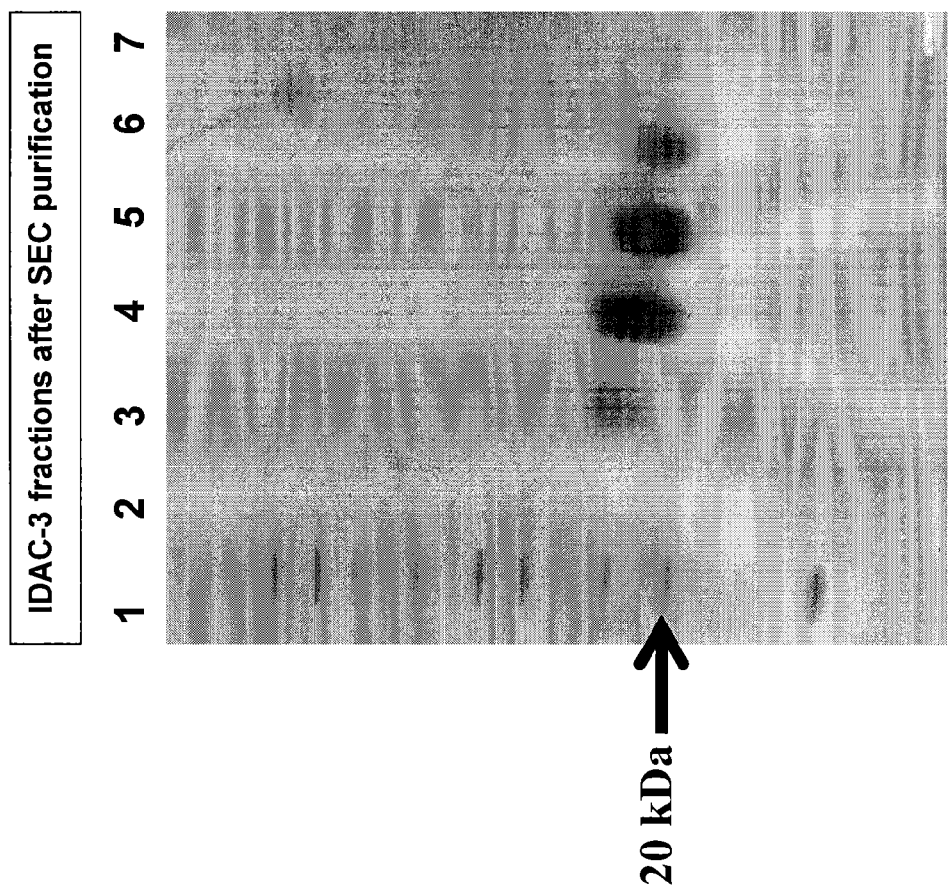
FIGS. 7A-7B illustrate the characterization of IDAC-1 and -3 by SDS-PAGE gel and CD.
Figure 7B:
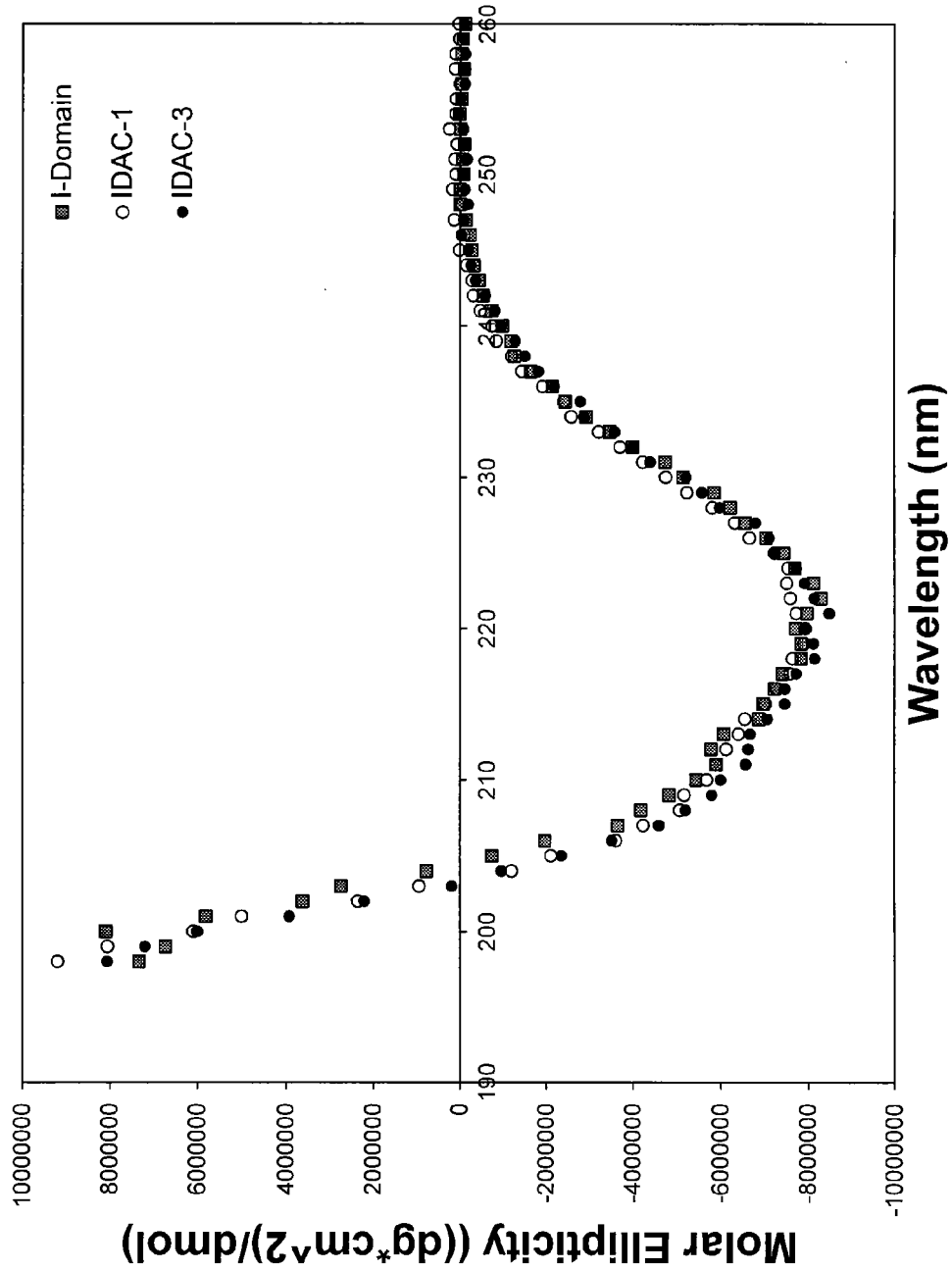

IDAC-1 and -3 were prepared by randomly conjugating the free amine groups of the I-domain with the N-hydroxysuccinimide group of GMBS, yielding GMB-I-domain. The resulting GMB-I-domain was then reacted with the thiol group of the Cys residue on PLP-Cys-OH or Ac-PLP-Cys-$NH_2$, yielding IDAC-1 and -3, respectively. Then, the resulting mixture was purified using size-exclusion column chromatography, and the eluted fractions were subsequently analyzed using SDS-PAGE (FIG. 7A). Multiple bands can be seen on SDS-PAGE due to the varying number of conjugated peptides on the I-domain. The earlier lanes on the gel have bands at a higher molecular weight compared to the later lanes, which corresponds to the order of elution of IDAC from the SEC. Analysis with circular dichroism shows that both IDAC-1 and -3 have spectra similar to that of the I-domain, indicating that multiple conjugations do not alter the secondary structure (FIG. 7B). The deconvoluted LC-MS data show that both IDAC molecules had 0-5PLP-Cys peptides conjugated per I-domain, with an average of 2.5 PLP-Cys peptides per I-domain molecule (data not shown).

Suppression of EAE by IDAC-1 and -3

Figure 8B:
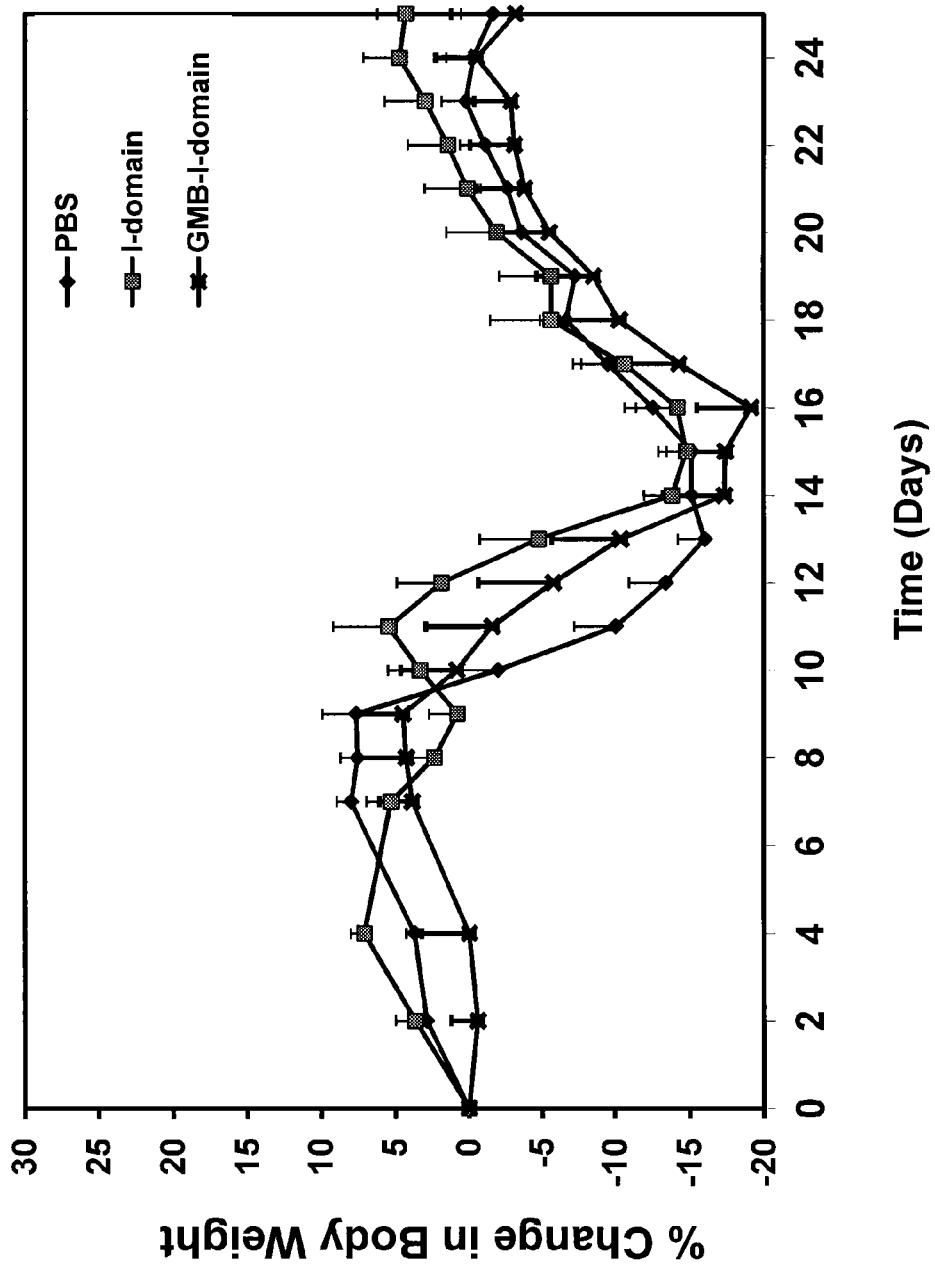
Figure 8C:
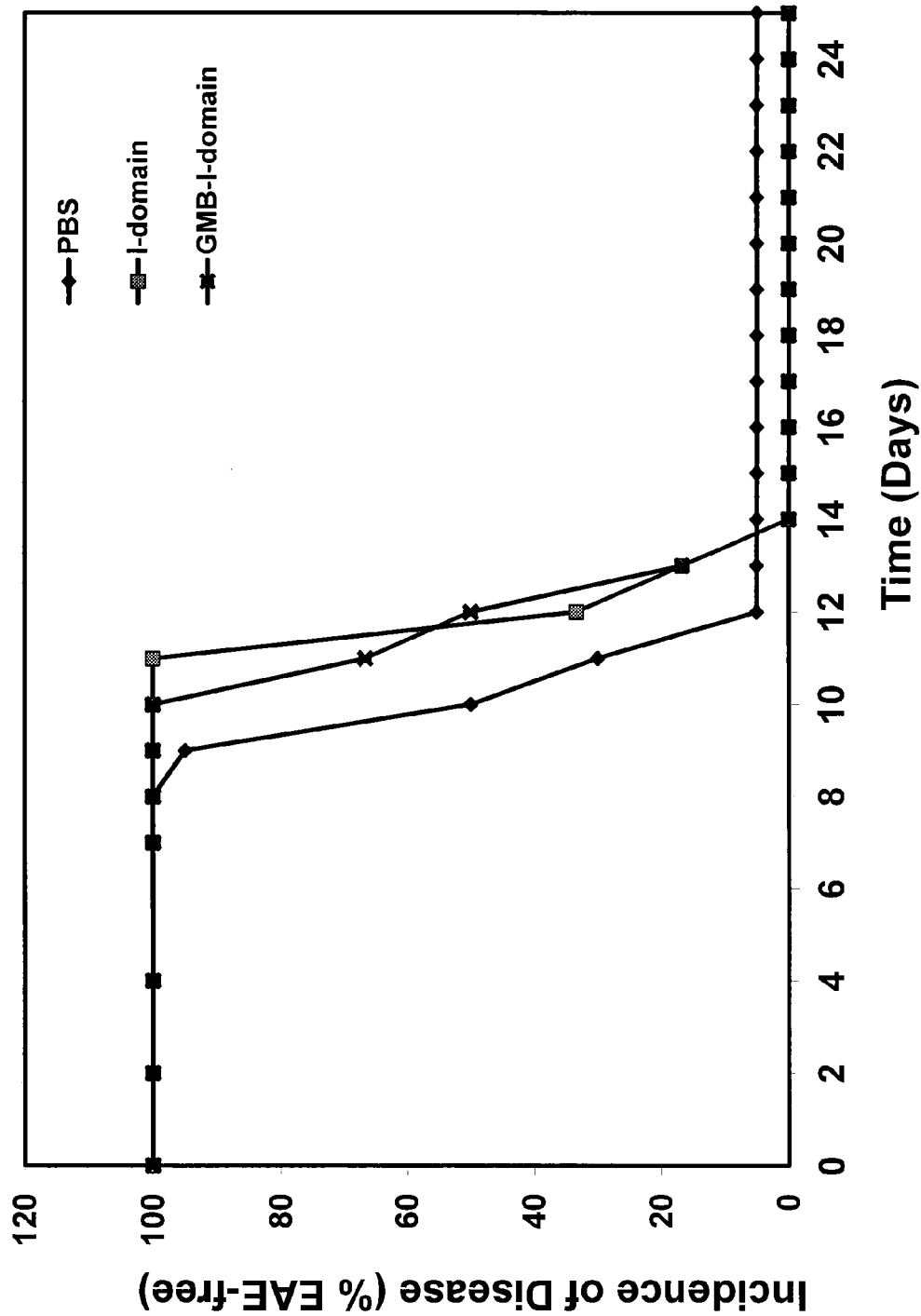

To test whether the I-domain and GMB-I-domain have in vivo efficacy, three groups of mice were treated with two intravenous injections of the I-domain or GMB-I-domain (26 nmol/injection) as well as PBS on days 4 and 7. Although there was a slight delay in the onset of the disease, neither the I-domain nor GMB-I-domain significantly suppressed the progress of EAE compared to the PBS-treated mice, as determined by the clinical score (FIG. 8A), change in body weight (FIG. 8B), and the incidence of disease (FIG. 8C).

In the second study, the efficacies of IDAC-1 and IDAC-3 with uncapped and capped PLP peptides, respectively, were compared upon intravenous injections of 26 nmol/injection on days 4 and 7; the control group was injected with PBS.

Figure 9A:
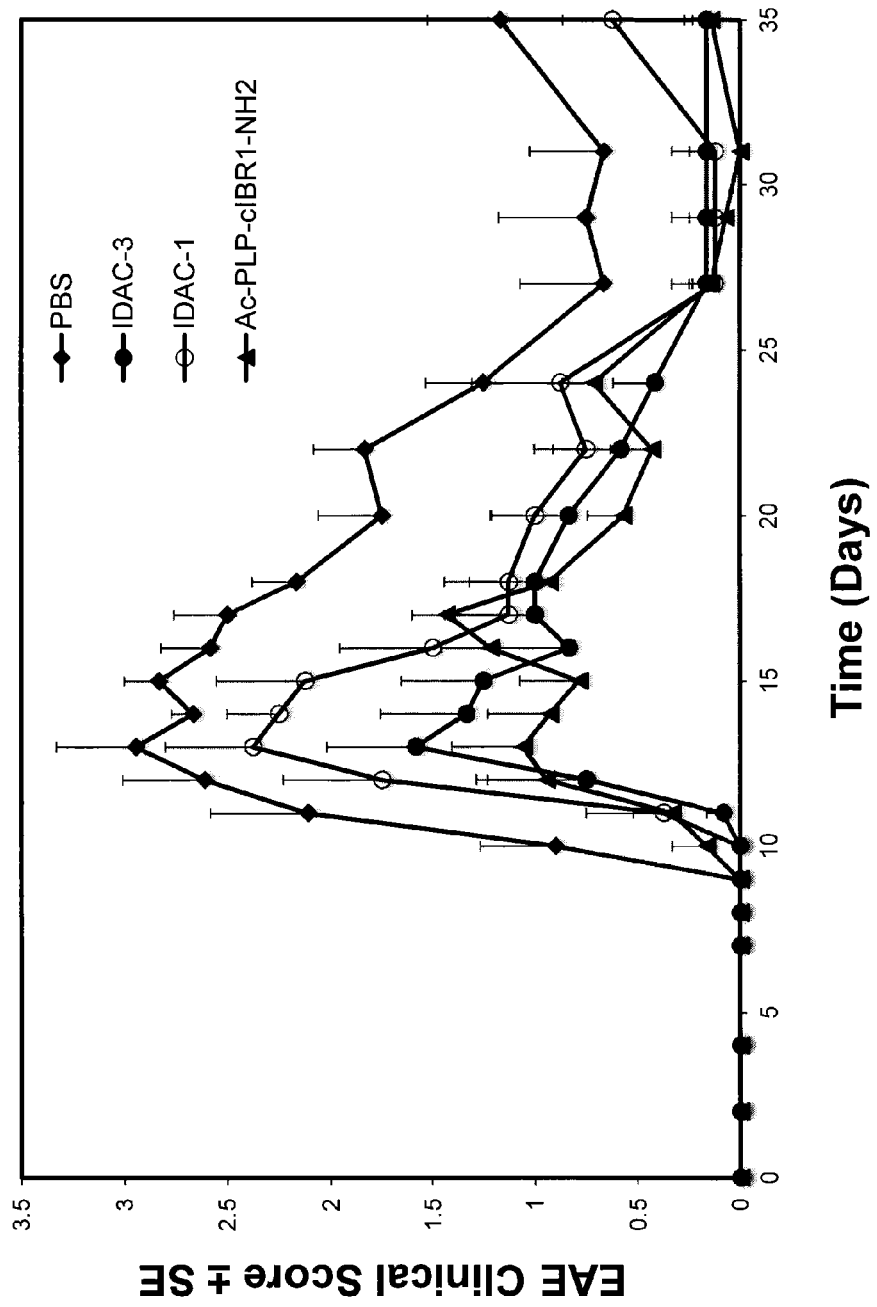
FIGS. 9A-9C illustrate a comparison of the in vivo activity of IDAC-1, IDAC-3, Ac-PLP-clBR1-NH$_2$, and PBS in mouse EAE model. After immunization with PLP peptide in CFA, the mice received i.v. injections of 26 nmol/injection/day with IDAC-1 or IDAC-3 on days 4 and 7. For the Ac-PLP-clBR1-NH$_2$ treatment group, the mice received i.v. injections of 50 nmol/injection/day of the peptide on days 4, 7, and 10. For the control mice, they were treated with PBS on days 4, 7, and 10. Disease progression was evaluated using clinical disease scores (9A), change in body weight (9B), and incidence of disease (9C). The results are expressed as the mean±S.E. (n≥6).
Figure 9B:
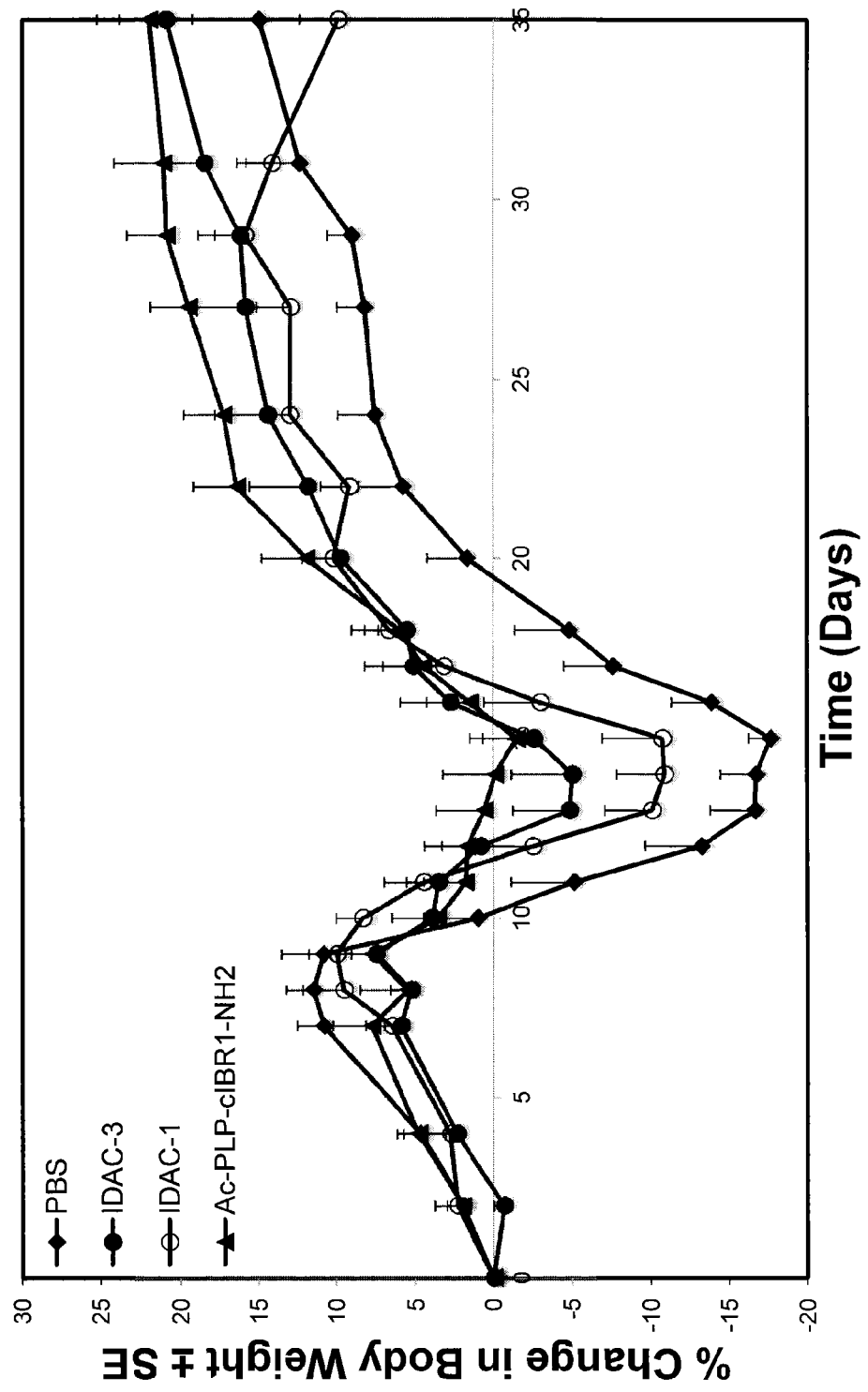
Figure 9C:
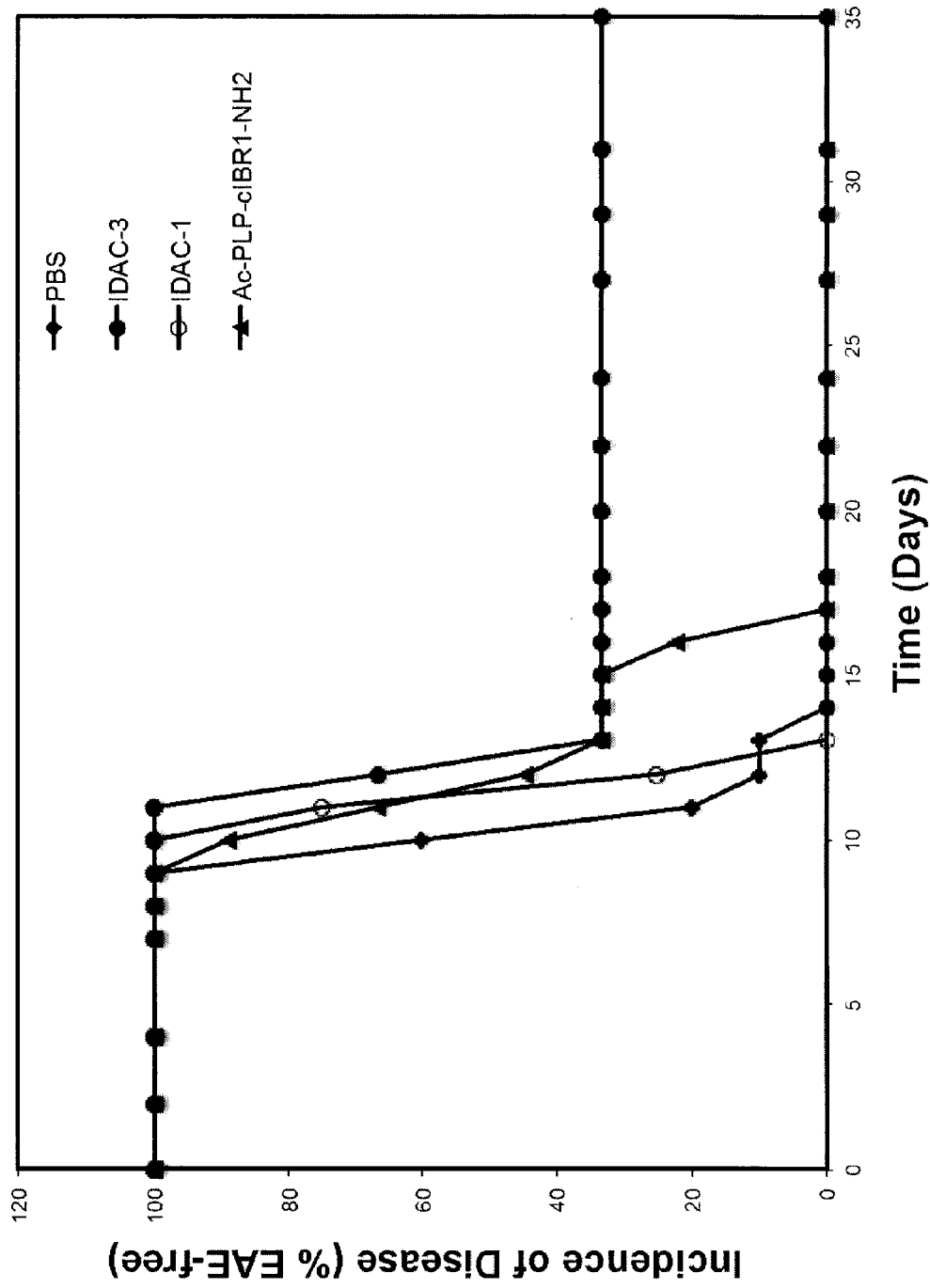

Using the clinical scores (FIG. 9A), both proteins delayed the onset of disease and were significantly better at suppressing EAE than PBS ($p<0.0005$, through days 12-17). Furthermore, IDAC-3 was better than IDAC-1 in suppressing EAE ($p<0.005$, through days 12-17), suggesting that capping the antigenic PLP peptide at both ends yields a more efficacious product. The body weight change for IDAC-1- and IDAC-3-treated animals supported the clinical score data; two injections of IDAC-1 and -3 were significantly more effective than PBS in suppressing disease results (FIG. 9B, $p<0.05$ through days 12-24). There were delays in disease incidence in IDAC-1- and IDAC-3-treated animals (FIG. 9C).

Figure 10A:
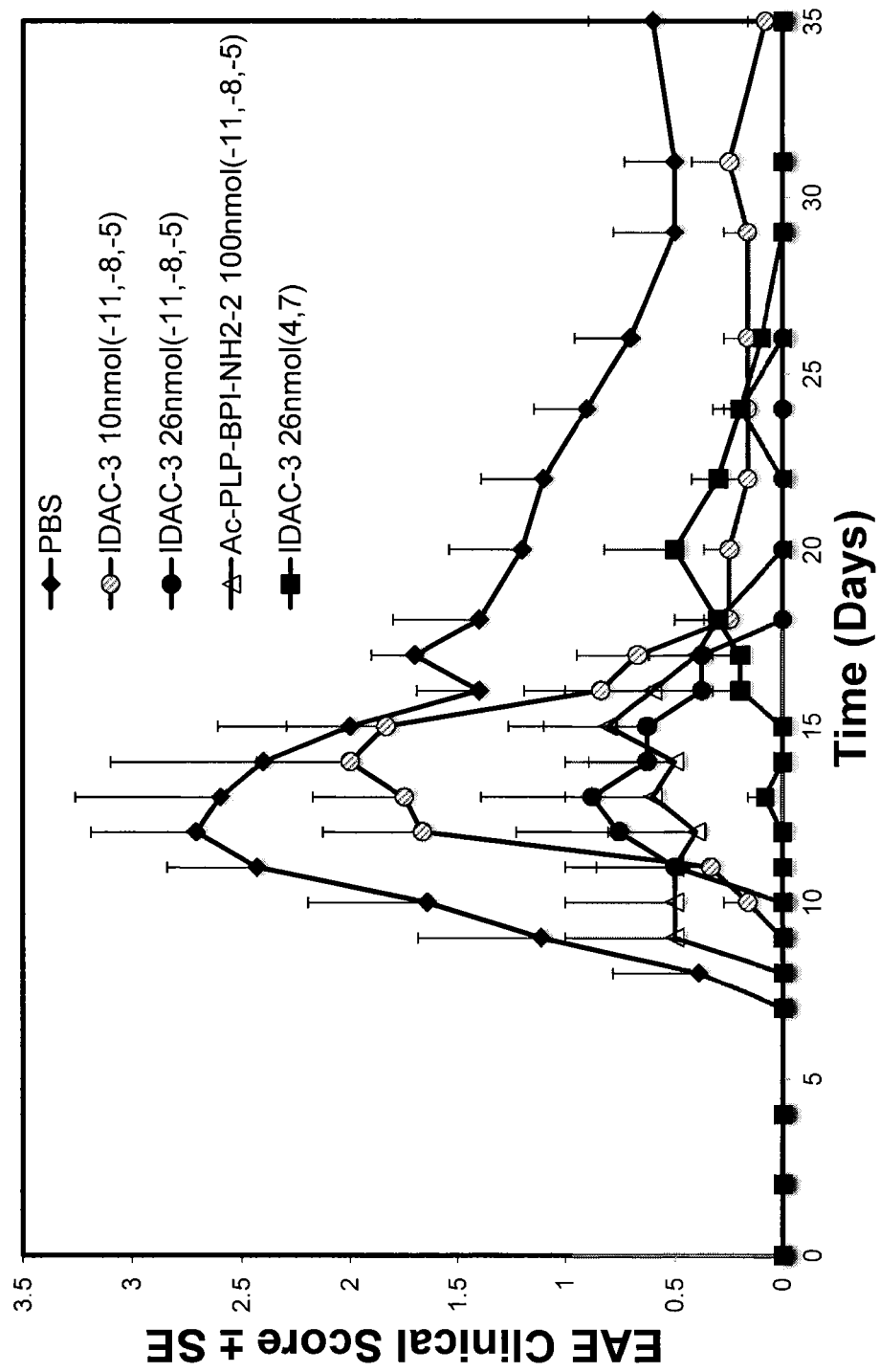
Figure 10B:
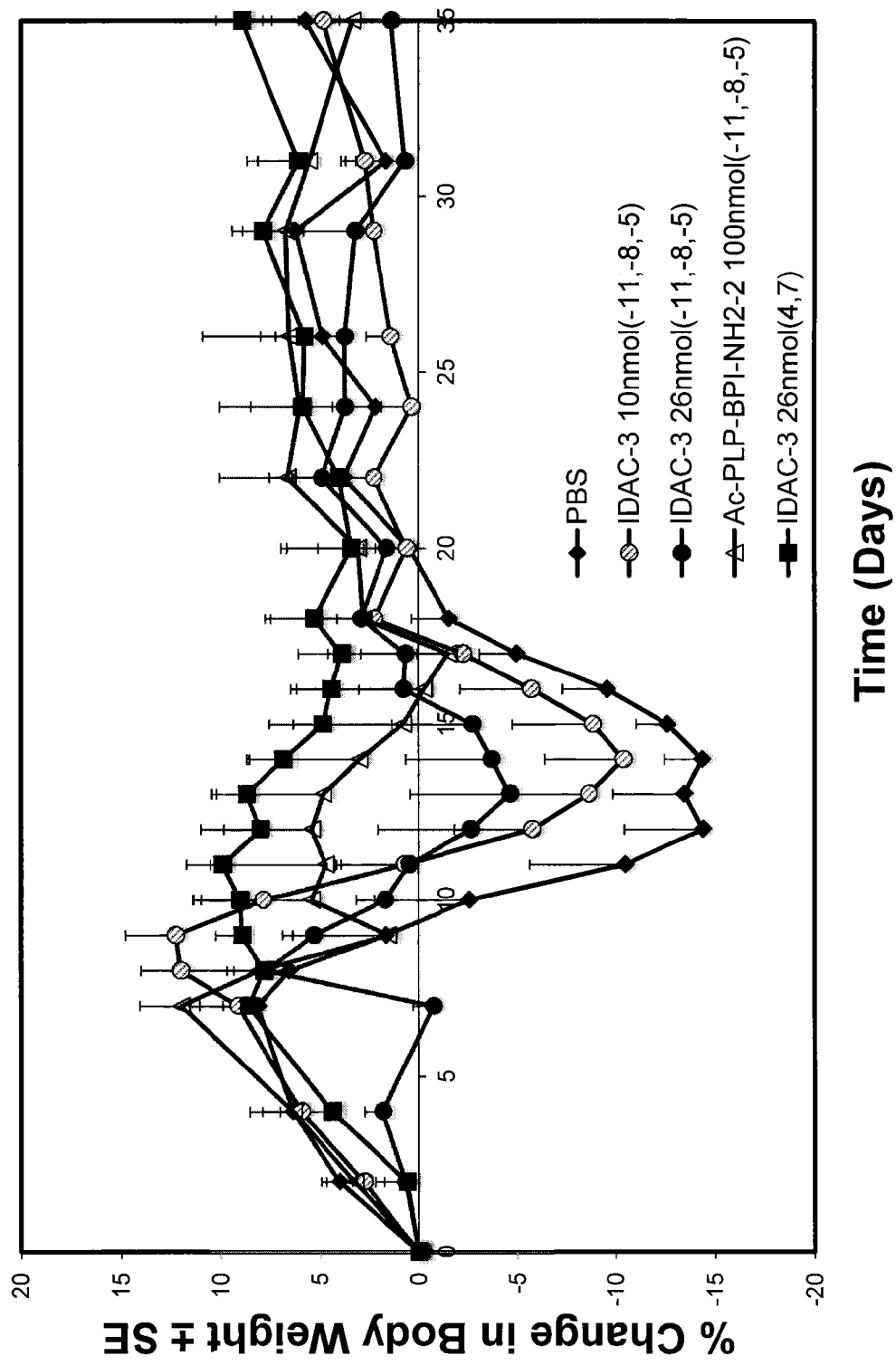

After establishing that IDAC-3 was a better candidate to suppress EAE, the third study was aimed at evaluating an alternative route of injection (i.e., subcutaneous or s.c.), dose response to determine therapeutic index, and optimal timing of IDAC-3 injections (FIG. 10). First, IDAC-3 injected s.c. (26 nmol/injection) on days 4 and 7 was significantly more efficacious than PBS in suppressing EAE as shown by clinical scores ($p<0.005$, through days 12-17; FIG. 10A), change in body weight of the mice ($p<0.005$, through days 12-24; FIG. 10B), and disease incidence (FIG. 10C). It is difficult to conclude whether s.c. administration is better than i.v. administration in the absence of direct comparison. Our previous studies indicated that s.c. administration of BPI molecules was more effective than i.v. administration. Second, the efficacy of IDAC-3 upon vaccine-like administrations was evaluated in different doses to determine the therapeutic index of the molecule. In this case, the mice received s.c. injections of two different doses of IDAC-3 (26 nmol/injection and 10 nmol/injection), Ac-PLP-BPI-NH$_2$-2 (100 nmol/injection), and PBS at 11, 8, and 5 days prior to the induction of the disease at day 0. Ac-PLP-BPI-NH$_2$-2, as positive control, significantly suppressed EAE compared to PBS as reflected in the clinical scores (FIG. 10A; $p<0.005$, days 12-17) and change in body weight (FIG. 10B; $p<0.005$, days 12-24). Although it was less potent than Ac-PLP-BPI-NH$_2$-2, mice treated with a low dose of IDAC-3 (10 nmol/injection) had significantly better clinical scores (FIG. 10A, $p<0.005$, days 12-17) and body weight changes (FIG. 10B; $p<0.005$ through days 12-24). At a high dose (26 nmol/injection), the third injection of IDAC-3 unfortunately caused a toxic effect in two of six mice; thus, the efficacy data were representative of four animals (FIG. 10). Although the statistical analysis was not carried out due to the lower number of animals, a high dose (26 nmol/injection) of IDAC-3 seemed to be better than the lower dose (10 nmol/injection) group and similar to the Ac-PLP-BPI-NH$_2$-2-treated group. Although IDAC-3 can effectively suppress the disease when given in a vaccine-like schedule, this study provided us with an estimated therapeutic window of IDAC-3 with a maximum toxic concentration of 3 injections of IDAC-3 at 26 nmol and a minimum effective concentration of 3 injections of 10 nmol. Finally, good efficacy of IDAC-3 was found upon two s.c. injections of IDAC-3 on days 4 and 7.

Figure 11A:
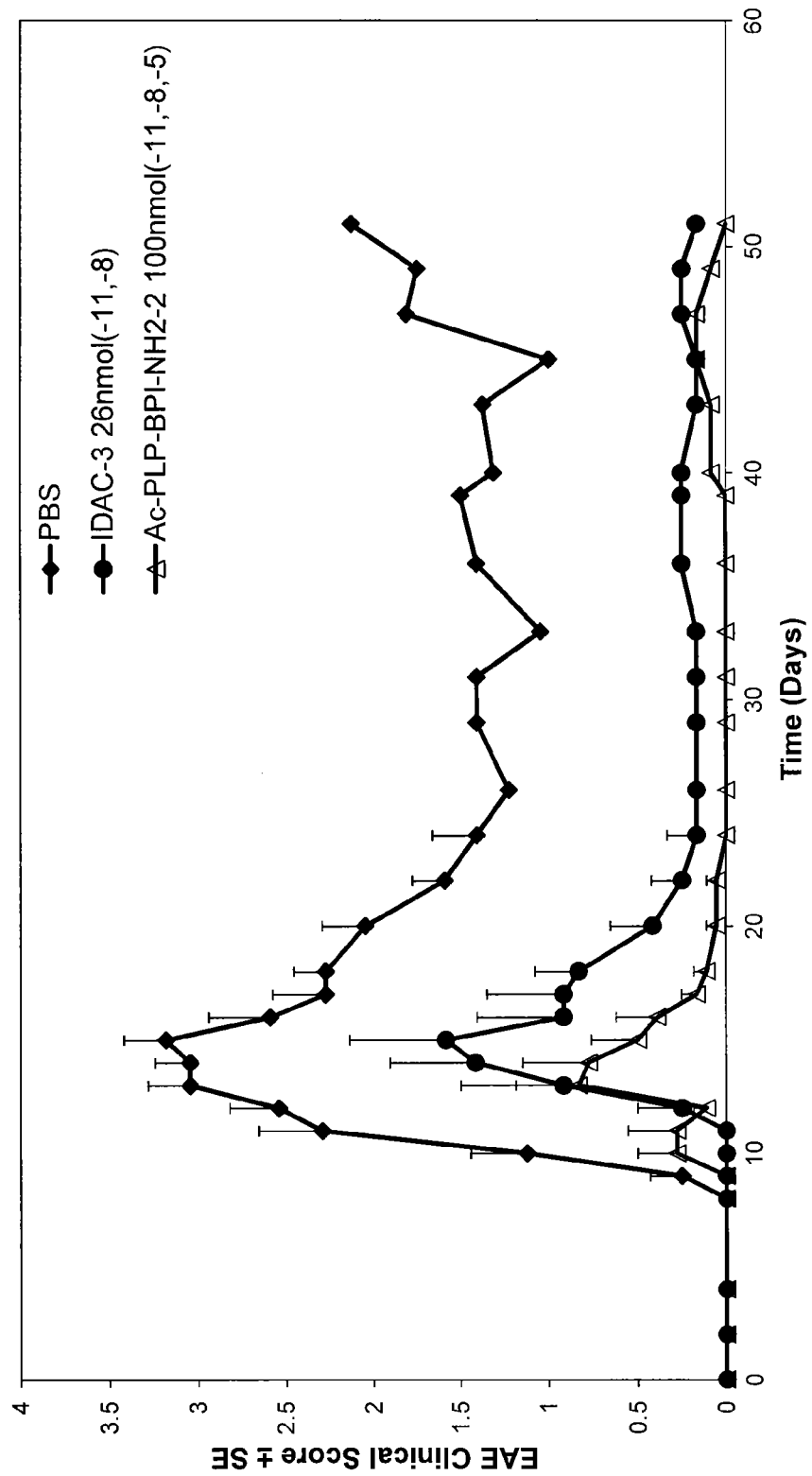
FIGS. 11A-11C illustrate a comparison of the in vivo activity of IDAC-3, Ac-PLP-BPI-NH$_2$-2, and PBS in mouse EAE model. After immunization with PLP peptide in CFA, the mice received vaccine-like s.c. injections of 26 nmol/injection/day with IDAC-3 on days −11 and −8. For the Ac-PLP-BPI-NH$_2$-2 treatment group, the mice received s.c. injections of 100 nmol/injection/day of the peptide on days −11, −8, and −5. For the control mice, they were treated with PBS on days −11, −8, and −5. Disease progression was evaluated using clinical disease scores (11A), change in body weight (11B), and incidence of disease (11C). The results are expressed as the mean±S.E. (n≥6).
Figure 11B:
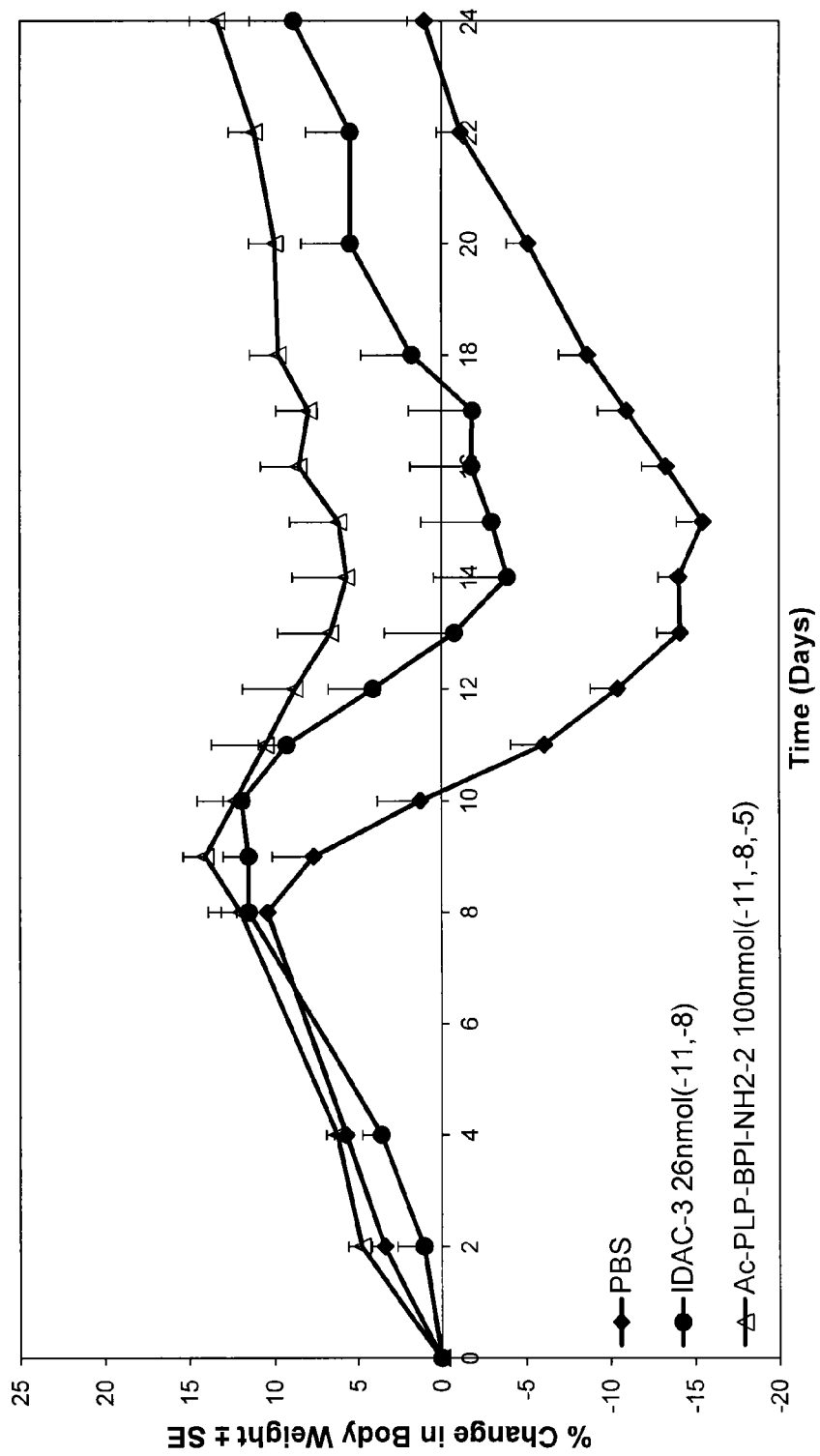
Figure 11C:
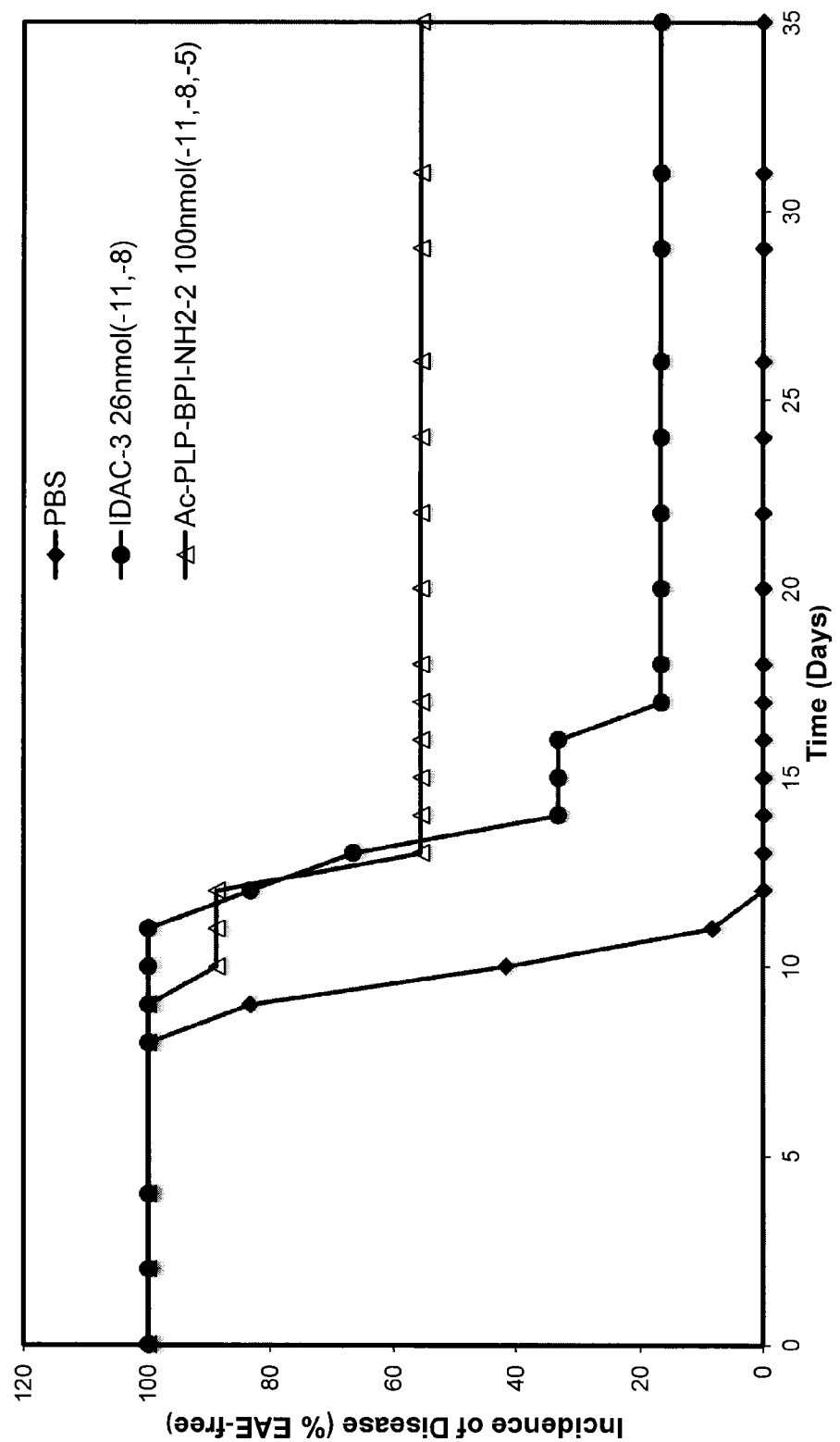

To test the optimal concentration for vaccine-like delivery and its long-term effect in suppressing relapse, IDAC-3 was injected twice via the s.c. route (26 nmol/injection on days −11 and −8) and was compared to three s.c. injections of Ac-PLP-BPI-NH$_2$-2 (100 nmol/injection; days −11, −8, and −5), and PBS (days −11, −8, −5). It is clear that two injections of IDAC-3 (26 nmol) suppressed EAE significantly better than PBS and had a long-term effect in suppressing relapse of the disease as indicated in the clinical scores (FIG. 11A, $p<0.0001$, days 12-17, and days 45-55) and change of body weight (FIG. 11B, $p<0.0001$, days 12-24). Similarly, Ac-PLP-BPI-NH$_2$-2 has along-term effect to prevent relapse. Delay in the onset of disease was observed in both treatment groups (FIG. 11C).

Cytokine Levels in SJL/J Mice In Vitro

Figure 12A:
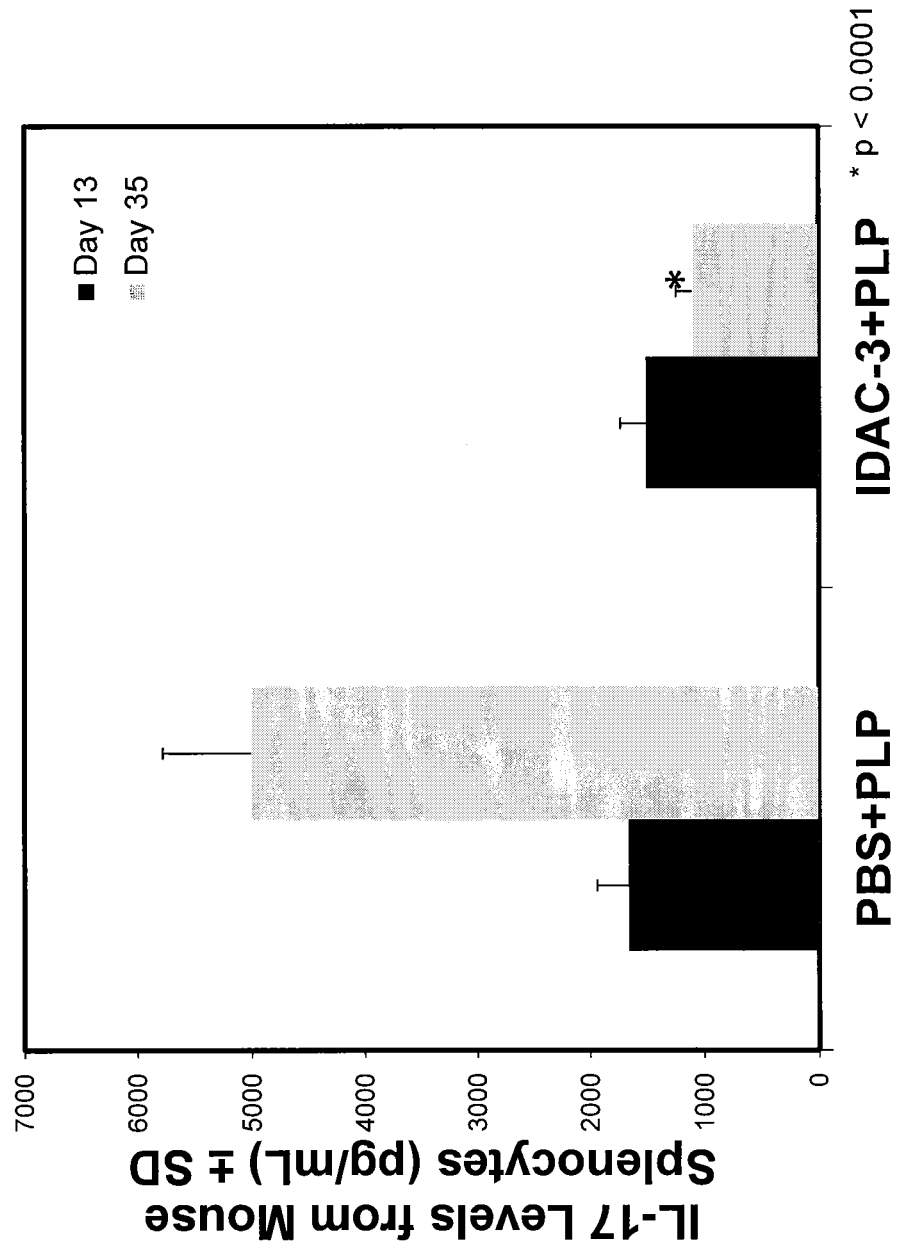

The potential mechanism of action of IDAC-3 was elucidated by comparing the cytokine levels (i.e., IL-2, IL-5, IL-10, IL-12, and IL-17) in splenocytes after two s.c. injections of IDAC-3 (26 nmol/injection) and PBS on days 4 and 7. The levels of cytokines were determined during the peak of disease on day 13 and after EAE went into remission and plateaued on day 35 (FIG. 12). Due to the low detection limit or the lack of statistical significance between IDAC-3 and PBS treatment, the levels of IL-4, IL-6, and IFNγ were not presented. One of the most exciting findings was that the IDAC-3-treated animals had fourfold lower IL-17 during the disease remission on day 35 compared to the PBS-treated group (FIG. 12A, $p<0.0001$).

Figure 12B:
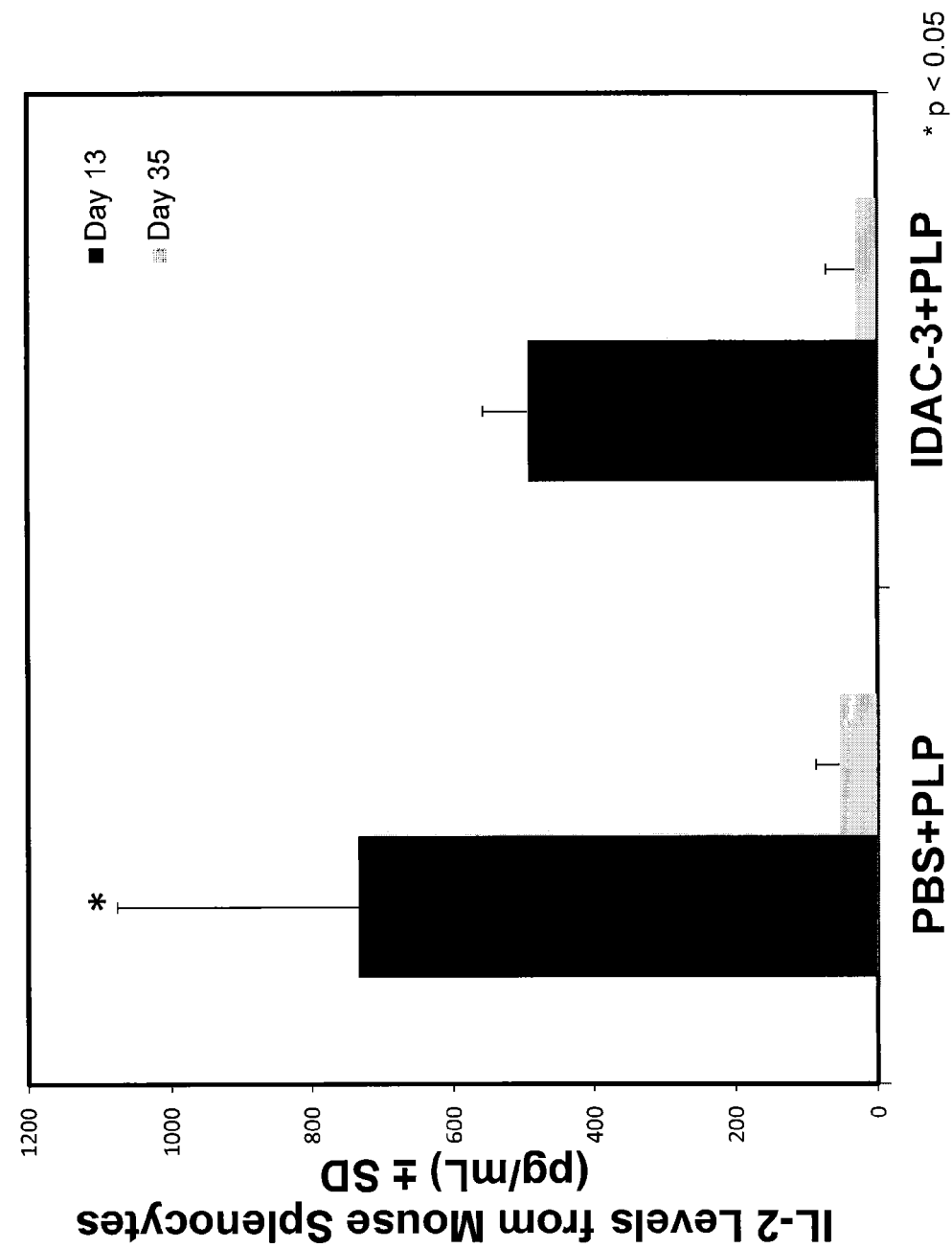
Figure 12C:
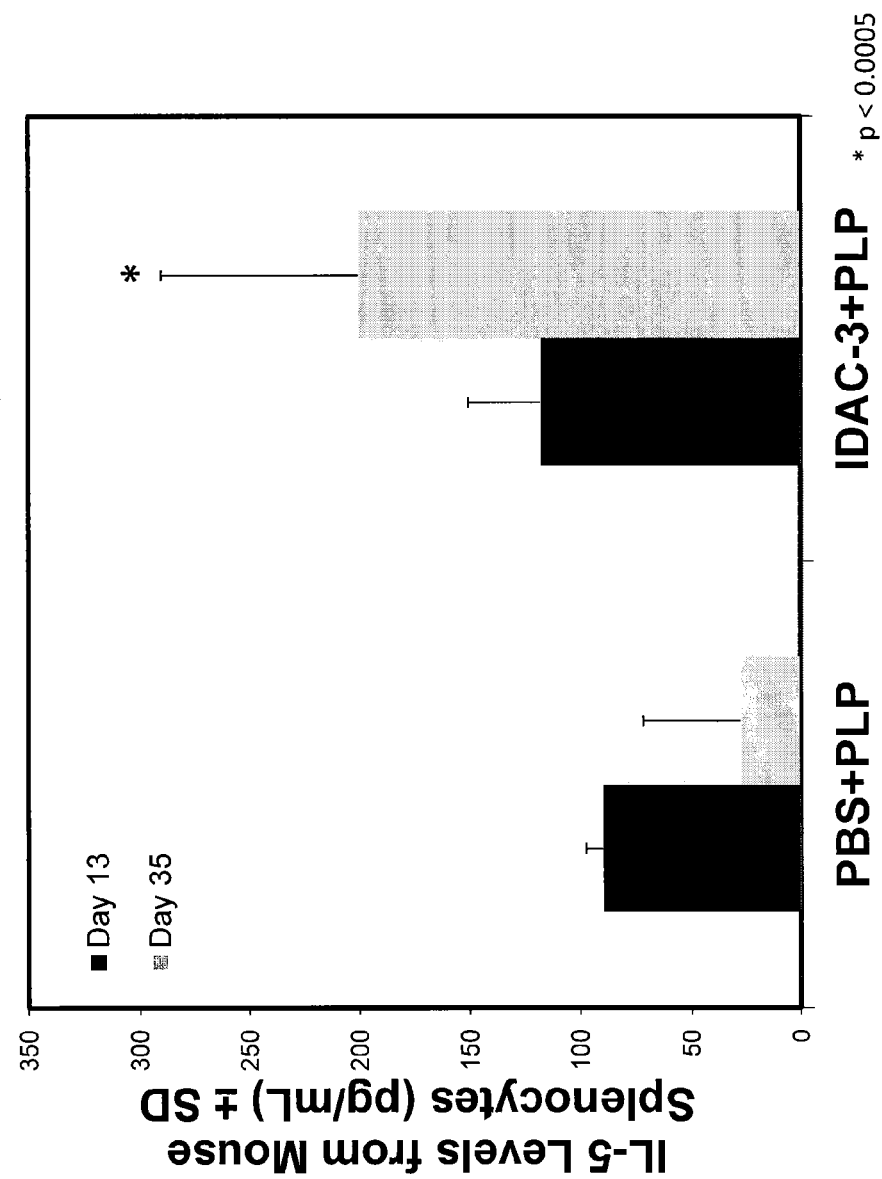
Figure 12F:
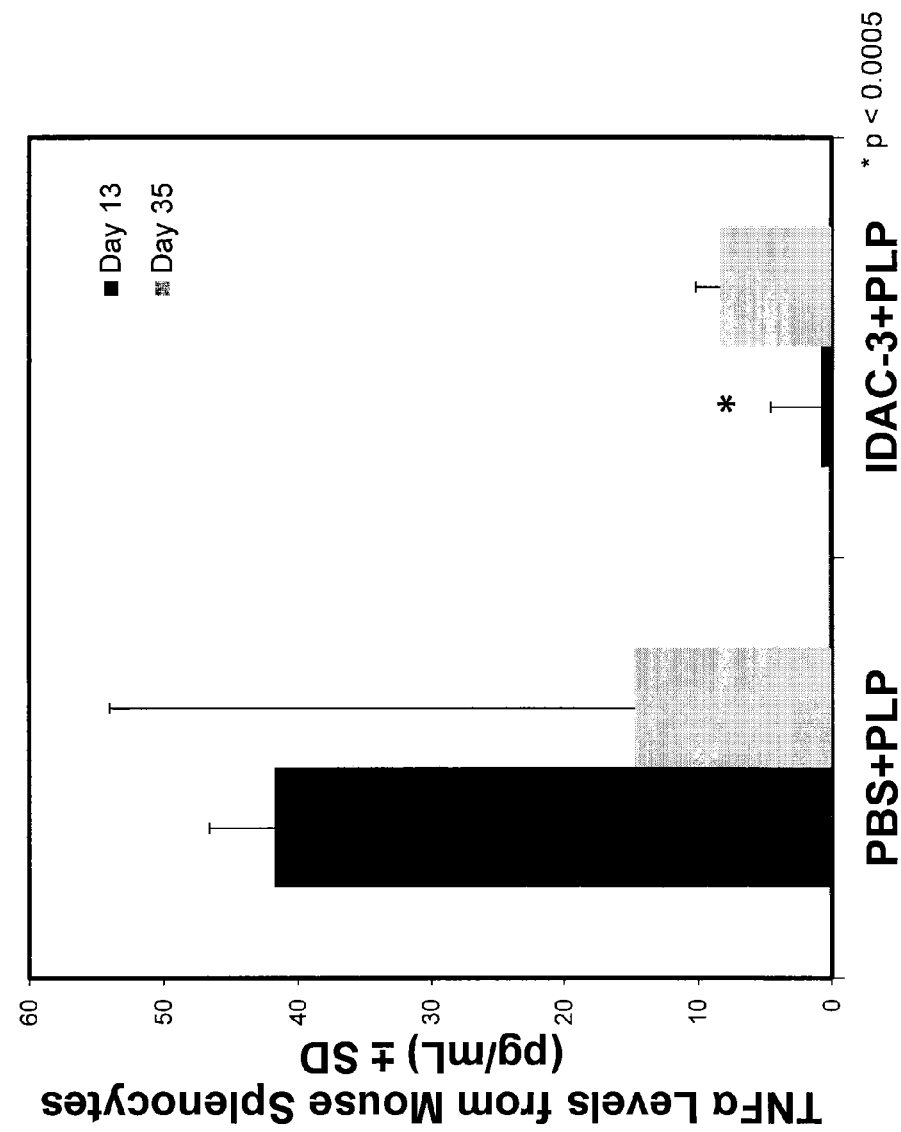
Figure 13A:
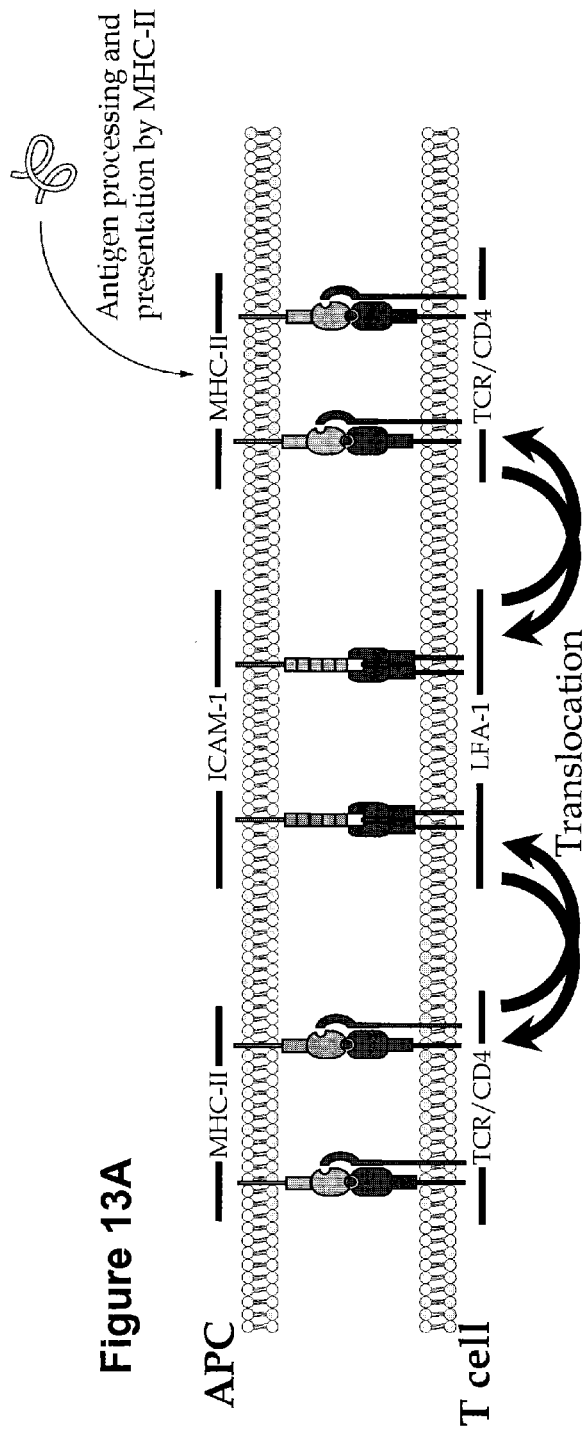
FIGS. 13A and 13B illustrate processing of antigens by and presentation by MHC-II of an antigen presenting cell to a T cell (13A) and formation of the immunological synapse (IS) (13B).
Figure 13B:
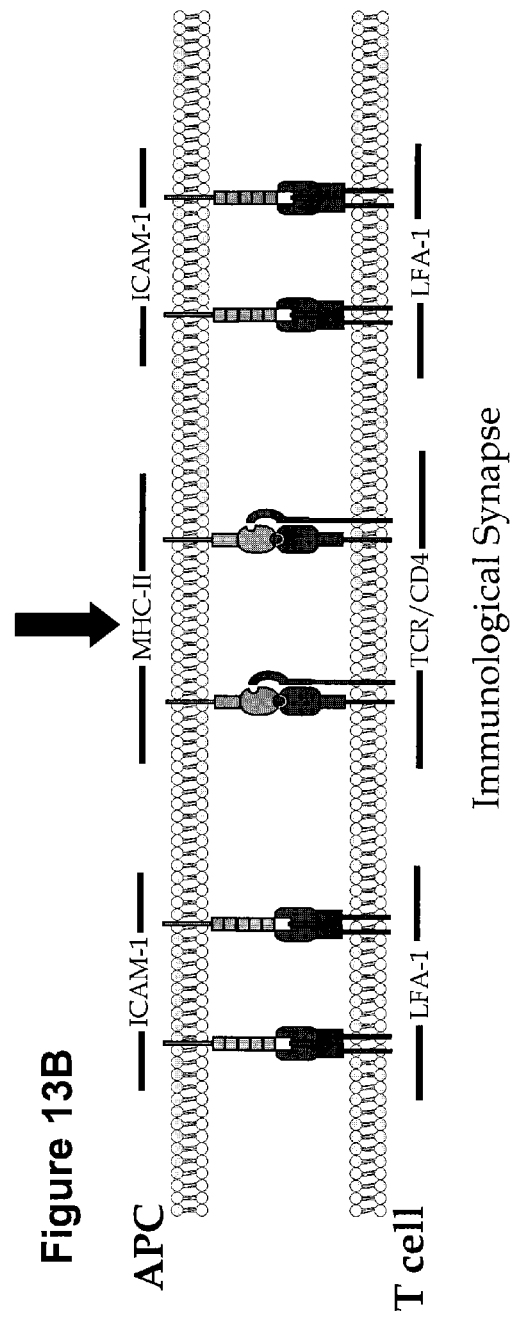
Figure 14:
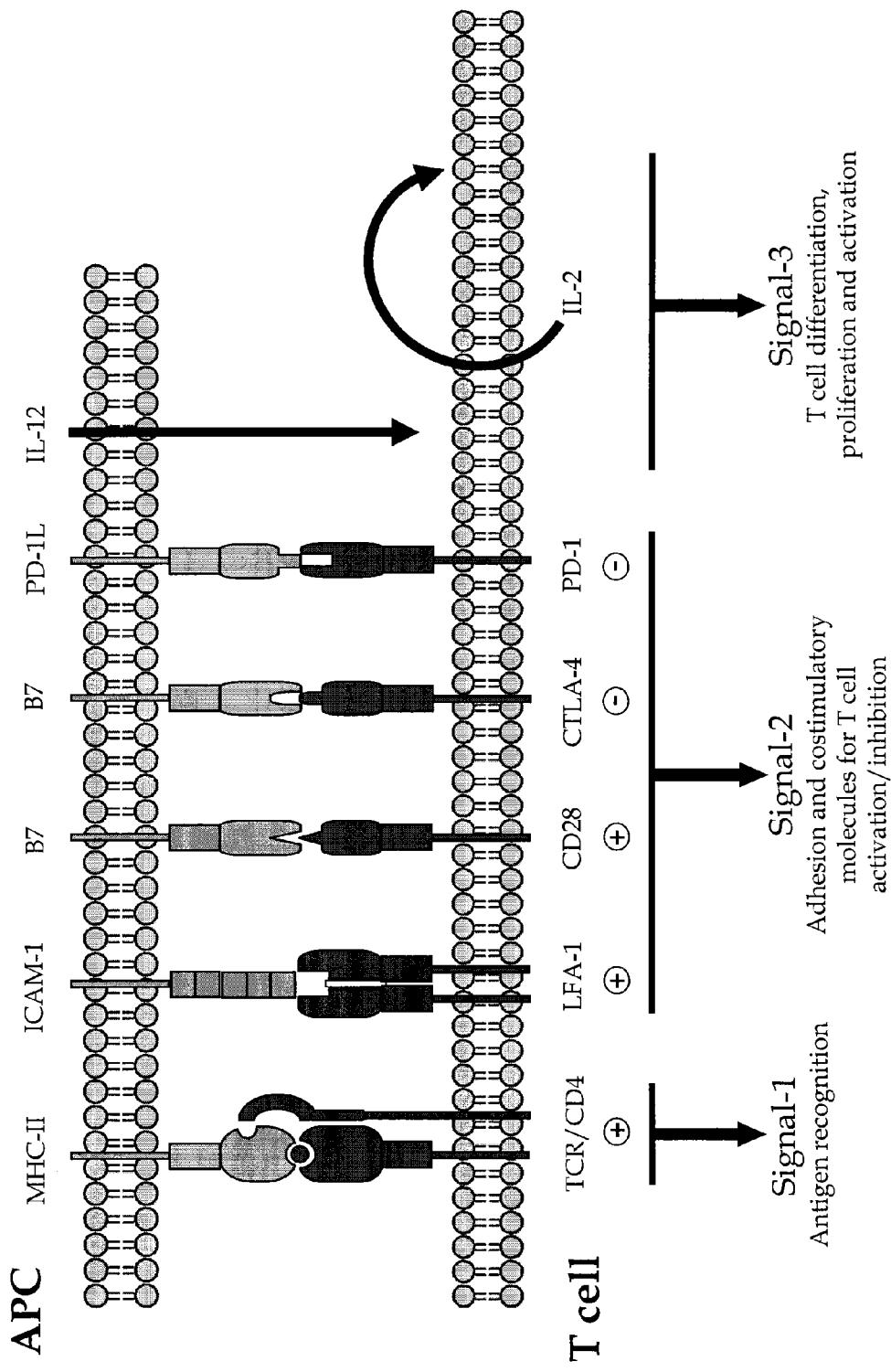
FIG. 14 illustrates signal 1, signal 2, and signal 3 interaction between antigen presenting cells (APC) and T cell of a host immune system.
Figure 15:
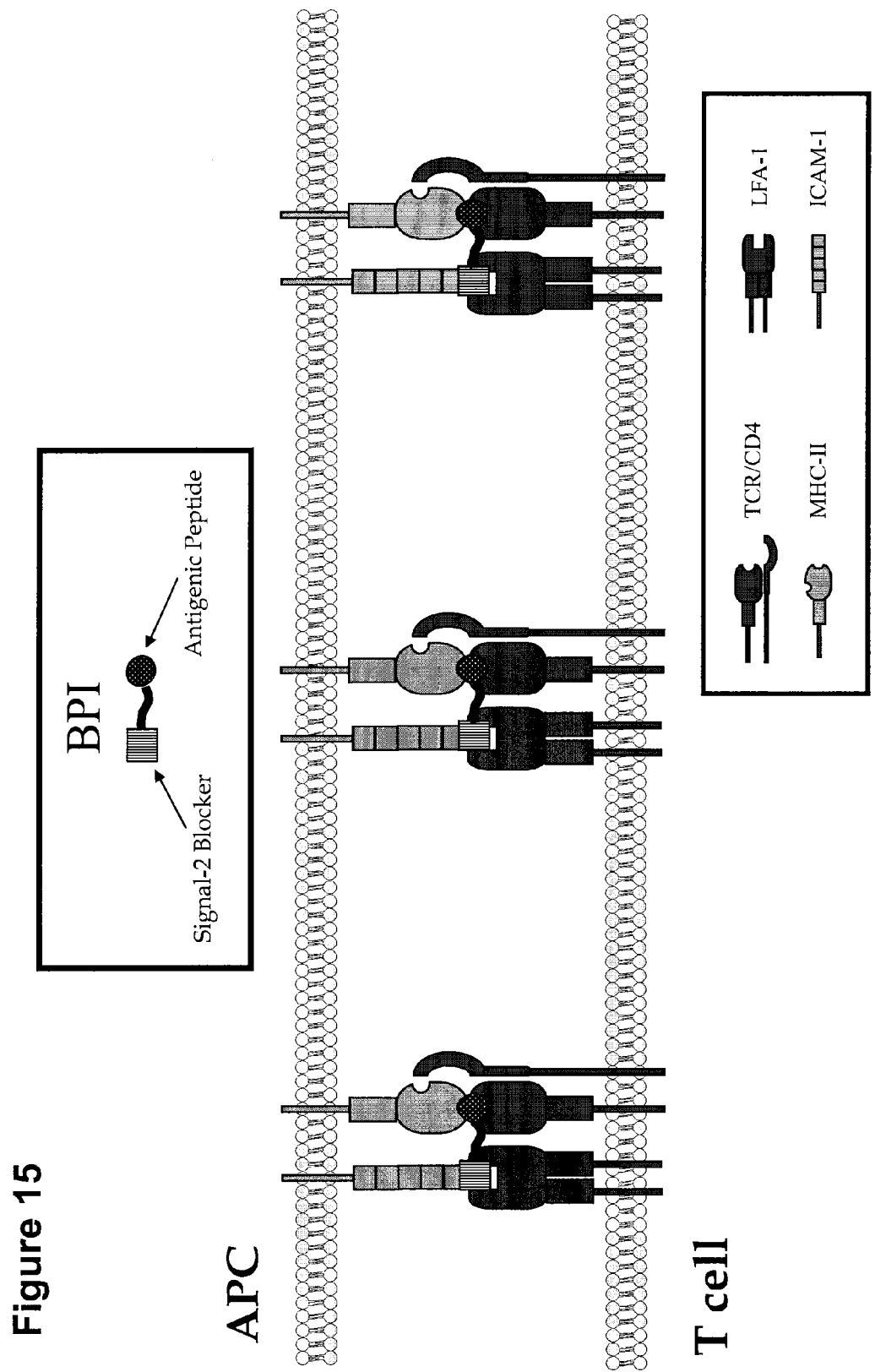
FIG. 15 illustrates the binding of a bifunctional BPI molecule to block signal 2 interaction between APC and T cells.
Figure 16:
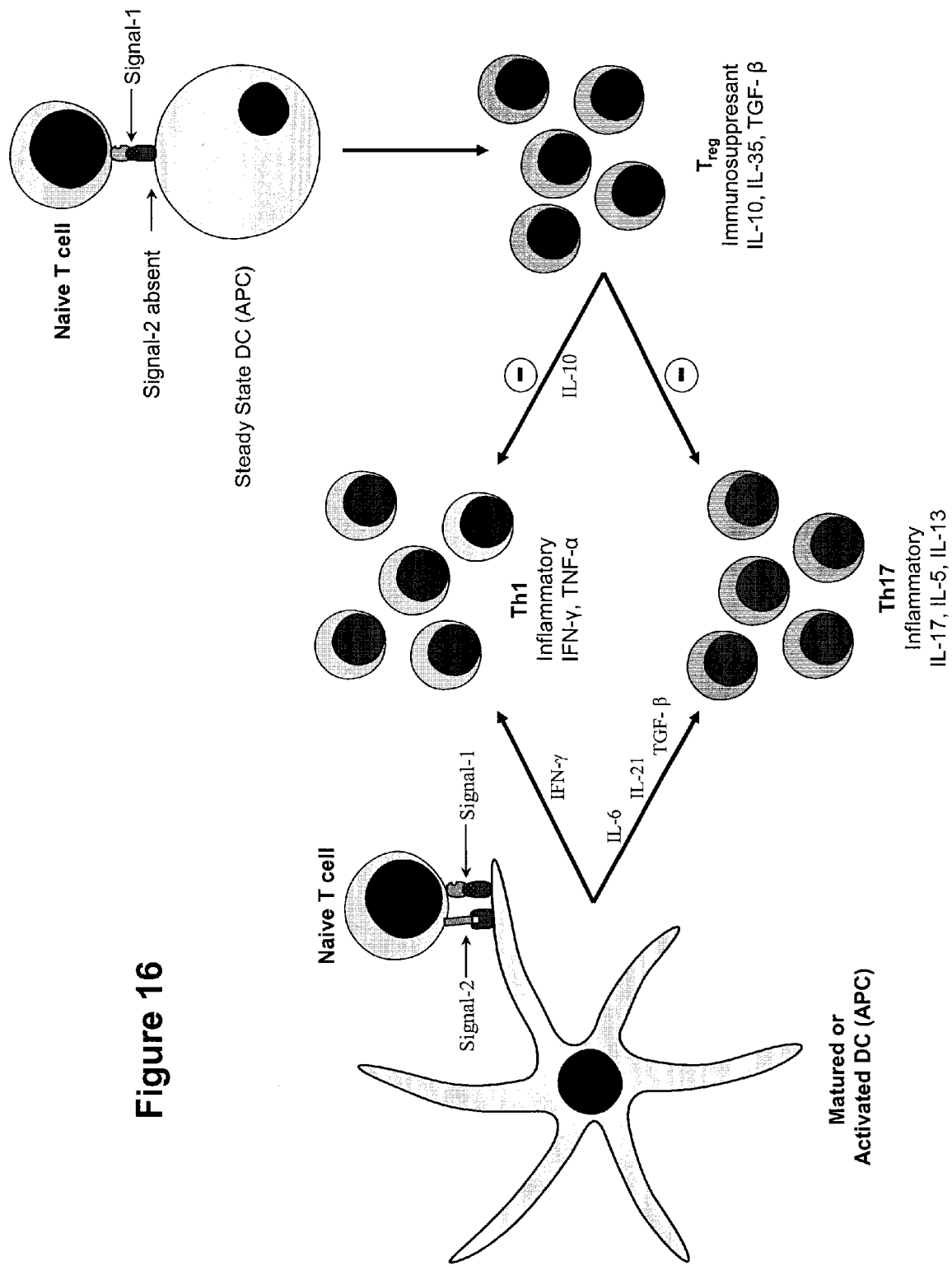
FIG. 16 illustrates interactions between naive T cells and activated DC (APC) vs. steady state DC (APC) to form inflammatory T-cell response.
Figure 17:
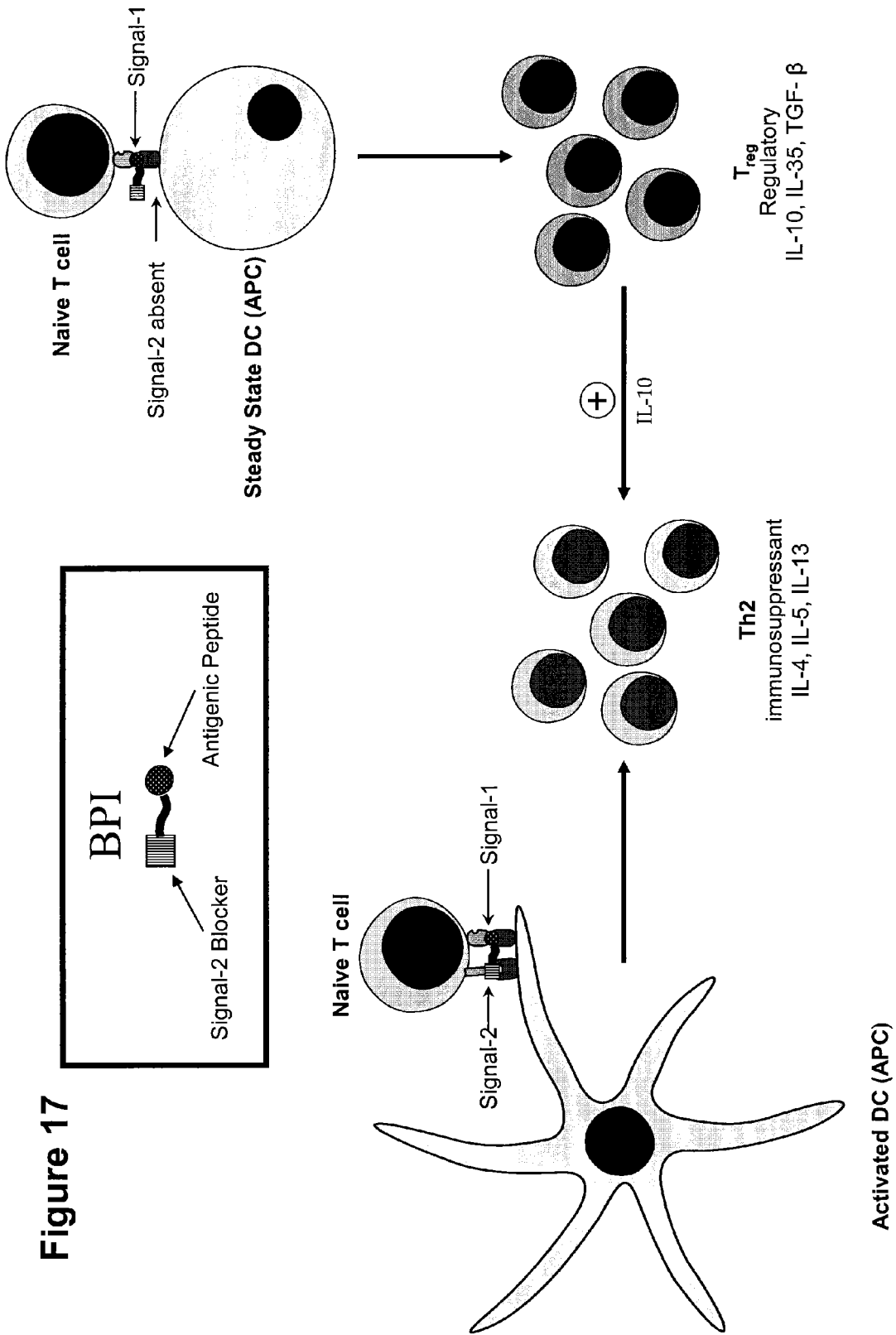
FIG. 17 illustrates the mechanism of blocking inflammatory T-cell response with BPI molecules by blocking signal 2 interaction between T cells and APCs to produce regulatory and immunosuppressant T cells.

In the PBS-treated group, IL-2 cytokine levels were higher than in the IDAC-3-treated group on day 13 ($p<0.05$) whereas no significant difference was observed on day 35 (FIG. 12B). Although there was no significant difference in IL-5 levels on day 13, the IL-5 levels on day 35 were significantly higher in the IDAC-3-treated group than in the PBS-treated group (FIG. 12C, $p<0.0005$). The cytokine levels of IL-10 on day 13 could not be detected; however, once the disease remission plateaued on day 35, the IDAC-3-treated group had significantly higher levels of IL-10 compared to the PBS group (FIG. 12D, $p<0.05$). In the IDAC-3-treated group, the level of IL-12 was significantly lower than in the PBS-treated group on day 35 (FIG. 12E, $p<0.005$).

Discussion

The present example shows the utility of the I-domain as a carrier protein to deliver antigenic peptides to suppress EAE. Previously, peptides derived from the I-domain, namely LABL (CD11a$_{237-246}$), had been conjugated to immunodominant antigenic peptides to suppress various autoimmune diseases in animal models of EAE, type 1 diabetes, and rheumatoid arthritis[7,8,10]. In these studies, LABL was conjugated to a single antigenic peptide (e.g., PLP, collagen-II, or GAD peptide). In the current study, the I-domain lysine residues were conjugated with multiple peptides from a single epitope (PLP$_{139-151}$), which resulted in a variety of different IDAC species. One of the advantages is that the I-domain can be used to simultaneously deliver multiple epitopes of PLP, as well as a mixture of epitopes from the proteolipid protein, myelin oligodendrocyte glycoprotein (MOG), and myelin basic protein (MBP). Another advantage of I-domain over LABL is that the I-domain contains the metal-ion dependent adhesion site (MIDAS) for divalent cation coordination (Ca$^{2+}$, Mg$^{2+}$, or Mn$^{2+}$) to enhance binding selectivity to ICAM-1 on the cell surface[13]. The expression of ICAM-1 is increased on cell surfaces in autoimmune diseases as well as in other diseases[14,15].

The results of the present example suggest that two injections (26 nmol/injection) of IDAC-3 with capped PLP peptide can suppress disease severity more efficiently than IDAC-1 with the uncapped PLP peptide. This corroborates a study in which capped Ac-PLP-BPI-NH$_2$-2 peptide could suppress EAE better than its uncapped counterpart (PLP-BPI)[7]. These results suggest that capped PLP peptide has higher metabolic stability than the uncapped peptide; in other words, the uncapped peptide is prone to exopeptidases (i.e., amino- and carboxy-peptidases). Because SDS-PAGE, CD, and mass spectrometry analyses suggest that IDAC-1 and IDAC-3 are similar, it is plausible that the major difference in their in vivo activity is due to the improved metabolic stability of the peptide and not to the different conformation of the molecule.

IDAC-3 dosed subcutaneously on days 4 and 7 was very effective in suppressing EAE, and one advantage of subcutaneous dosing is that IDAC molecule could drain into the lymph nodes to modulate immune cells[16,17]. The vaccine-like delivery of IDAC-3 has a significant long-term effect in suppressing disease relapse after 55 days compared to PBS, suggesting that IDAC-3 works by tipping the balance of the immune cells from inflammatory to regulatory phenotypes. It also suggests that vaccine-like delivery can alter the balance of the immune cells to regulatory cells prior to the stimulation of the disease. However, IDAC-3 may have a narrow therapeutic index because the third injection of 26 nmol of IDAC-3 on day −5 in vaccine-like delivery appeared to cause adverse events in 2 of the 6 mice. A lower dose of vaccine-like subcutaneous injections of 10 nmol on days −11, −8, and −5 in a separate group did not result in anaphylaxis, but was not as effective as the 26 nmol dose. As controls, I-domain and the GMB-I-domain had slight delays of disease onset, but no significant suppression of disease; this activity is due to the general inhibition of LFA-1/ICAM-1-mediated leukocyte adhesion[11]. Thus, the effect of injections of IDAC-3 and I-domain on the change or differentiation of immune cells will be evaluated in the future. In addition, the effect of increasing the dose while maintaining the schedule of 2 injections as well as multiple injections (greater than 3 injections) at low doses (less than 10 nmol) by spreading the injection over a larger timespan will also be investigated.

During the peak severity of the disease on day 13, splenocytes isolated from the mice treated with PBS and IDAC-3 had similar levels of IL-17 production. However, on day 35, IDAC-3-treated mice were found to have significantly lower levels of IL-17 compared to the PBS group, indicating that IDAC-3 has long-term effects in suppressing EAE. Th17 is a major T cell found to play a large role in the pathogenesis of both EAE and MS[5,18-21]. A significant suppression of disease, coupled with lower levels of IL-17 on day 35, suggests that two injections of IDAC-3 suppressed the disease by modulating the immune system of the mice and shifting the response to the disease from inflammatory to regulatory phenotypes. The higher level of IL-17 on day 35 in the mouse group treated with PBS may suggest an impending relapse of disease. This correlates with our previous observations in mice treated with Ac-PLP-BPI-NH$_2$-2, suggesting the involvement of regulatory cells and the down-regulation of Th17[7,9].

While IL-10 levels were below detection limits on day 13, higher levels of IL-10 production were observed in mice treated with IDAC-3 compared to PBS on day 35, indicating the potential involvement of T-reg cells. Previously, BPI-treated animals also produced IL-10 cytokine[8]. In addition, IDAC-3 induced IL-5, indicating the involvement of Th2 phenotype. A shift away from a Th1-response was observed from the involvement of lower levels of IL-2 in the IDAC-3-treated group compared to the PBS-treated mice. Furthermore, the lower levels of IL-12 in the IDAC-3-treated compared to PBS-treated mice imply that the IDAC-3 induces the differentiation away from a Th1-mediated response to a non-immunogenic response.

The potential mechanisms of action of IDAC-3 could be due to the delivery of the antigenic peptide to APC to alter the differentiation of naïve T cells to regulatory T cells and suppress the proliferation of inflammatory Th17 and Th1. As in BPI molecules, IDAC-3 could bind simultaneously to ICAM-1 and MHC-II to inhibit the formation of the immunological synapse at the interface between T cells and APC. By inhibiting the formation of the immunological synapse, the differentiation of T cells is shifted from inflammatory to immune-regulatory response. Previously, it was found that a BPI molecule (GAD-BPI) that suppressed Type 1 Diabetes could simultaneously bind to MHC-II and ICAM-1 and co-localize them on the surface of B cells isolated from the non-obese diabetic (NOD) mouse[10]. Another possible mechanism by which IDAC could work is that the 1-domain binds to ICAM-1 and the conjugate is internalized[11,22]. Previous studies showed that the 1-domain conjugated to fluorophores at the Lys residues could effectively bind to ICAM-1 and enter leukocytes by receptor-mediated endocytosis despite having a heterogeneous mixture[11,23]. The proposed mechanism is that IDAC-3 binds to ICAM-1 and suppresses the adequate leukocyte adhesion needed to form a steady T cell:APC contact. Once IDAC-3 is internalized into the APC cytoplasm, PLP is loaded onto the MHC-II in the Golgi apparatus and is transported to the cell surface for presentation, while the internalized ICAM-1 is down-regulated and disappears from the cell surface[22]. Therefore, at the time the PLP-MHC-II-complex is presented at the surface of APC, the second signal (ICAM-1:LFA-1) for T cell activation is absent, leading to T-reg differentiation[24,25]. However, the internalized ICAM-1 has been shown to recycle and resurface and, therefore, the absence of the second signal is transient[22]. Along the same line, another proposed mechanism is that IDAC-3, in the intracellular domain prior to recycling to the surface, could bind with empty MHC-II to form a complex of MHC-II/IDAC-3/ICAM-1 followed by presentation to the surface in a co-localized fashion. This co-localization prevents the formation of the immunological synapse. In the future, studies will be carried out to elucidate the potential mechanisms of action of IDAC molecules.

IDAC-3 is a mixture of conjugation products in which several lysine residues are conjugated with PLP peptide. The conditions of conjugation reaction have been optimized to maintain batch-to-batch reproducibility, as determined by mass spectrometry and CD. Using tryptic digest and mass spectrometry the sites of peptide conjugation were determined and the number of conjugations was found to be between one and five peptides per 1-domain. Because IDAC-3 is a mixture, it is possible that not all of the conjugated products have biological activity to suppress EAE. In the future, several individual lysine residues will be mutated to cysteine residues (Cys-I-domain) for selective conjugation of peptides to a selected cysteine residue. It should be noted that the 1-domain does not contain any cysteine residues. Thus, the resulting conjugate will be a single conjugate instead of a mixture of conjugates. Then, the efficacy of each conjugated product will be evaluated in the EAE mouse model. This study will provide us with the conjugation site(s) in the 1-domain that produce biological activity.

In conclusion, IDAC-3 effectively inhibited the onset and severity of EAE in the mouse model. The conjugation of multiple copies of a single antigenic epitope to a single molecule of 1-domain suppresses EAE by shifting the immune response to a regulatory phenotype. IDAC-3 can also suppress the relapse of EAE when delivered in a vaccine-like manner. Further studies using IDAC will involve optimizing the dose and the dosing strategy to lower toxicity and improve efficacy. Finally, the effect of epitope spreading will be addressed by conjugating other immunodominant epitopes, such as MOG and MBP, to the I-domain.

tional peptide inhibitor: structure optimization and pharmacokinetics. *J Pharmacol Exp Ther* 332, 1136-1145, doi:10.1124/jpet.109.161109 (2010).

TABLE 3

List of embodiments of peptides and proteins used in Example 2

| Peptide/Protein | Sequence (SEQ ID NO and/or description of the sequence follows in parenthesis () and/or brackets []) |
|---|---|
| I-domain | MGNVDLVFLFDGSMSLQPDEFQKILDFMKDVMKKLSNTSYQFAAV QFSTSYKTEFDFSDYVKRKDPDALLKHVKHMLLLTNTFGAINYVATE VFREELGARPDATKVLIIITDGEATDSGNIDAAKDIIRYIIGIGKHFQTK ESQETLHKFASKPASEFVKILDTFEKLKDLFTELQKKIY (SEQ ID NO: 1) |
| Ac-PLP-BPI-$NH_2$-2 | *Ac*-HSLGKWLGHPDKF-$(AcpGAcpGAcp)_2$-ITDGEATDSG-$NH_2$ [(SEQ ID NO: 13)-(SEQ ID NO: 29)-(SEQ ID NO: 30)-$NH_2$] |
| Ac-PLP-CIBR1-$NH_2$ | *Ac*-HSLGKWLGHPDKF--$(AcpGAcpGAcp)_2$-Cyclo(1,12)-PenPRGGSVLVTGC-$NH_2$ [(SEQ ID NO: 13)-(SEQ ID NO: 29)-cyclo(1,12)-Pen-(SEQ ID NO: 31)-$NH_2$] |
| IDAC-1 | $(HSLGKWLGHPDKFC)_n$-linker-I-domain [(SEQ ID NO: 2)-linker-(SEQ ID NO: 1)] |
| IDAC-3 | $(Ac\text{-}HSLGKWLGHPDKFC\text{-}NH_2)_n$-linker-I-domain [Ac-(SEQ ID NO: 2-$NH_2$)$_n$-linker- (SEQ ID NO: 1)] |
| GMB-I-domain | [N-(γ-maleimido)-1-oxybutyl]$_n$-I-domain [[N-(γ-maleimido)-1-oxybutyl]$_n$-SEQ ID NO: 1] |

Ac = Acetyl and Acp = Aminocaproic acid

Example 2 References

1 Ascherio, A. & Munger, K. L. Environmental risk factors for multiple sclerosis. Part I: the role of infection. *Ann Neurol* 61, 288-299, doi:10.1002/ana.21117 (2007).

2 Ascherio, A. et al. Epstein-Barr virus antibodies and risk of multiple sclerosis: a prospective study. *Jama* 286, 3083-3088 (2001).

3 Bagert, B. A. Epstein-Barr virus in multiple sclerosis. *Curr Neurol Neurosci Rep* 9, 405-410 (2009).

4 Brennan, R. M. et al. Strains of Epstein-Barr virus infecting multiple sclerosis patients. *Mult Scler* 16, 643-651, doi: 10.1177/1352458510364537 (2010).

5 Fletcher, J. M., Lalor, S. J., Sweeney, C. M., Tubridy, N. & Mills, K. H. T cells in multiple sclerosis and experimental autoimmune encephalomyelitis. *Clin Exp Immunol* 162, 1-11, doi:10.1111/j.1365-2249.2010.04143.x (2010).

6 Manikwar, P., Kiptoo, P., Badawi, A. H., Buyuktimkin, B. & Siahaan, T. J. Antigen-specific blocking of CD4-specific immunological synapse formation using BPI and current therapies for autoimmune diseases. Med Res Rev, doi:10.1002/med.20243 (2011).

7 Kobayashi, N. et al. Prophylactic and therapeutic suppression of experimental autoimmune encephalomyelitis by a novel bifunctional peptide inhibitor. *Clin Immunol* 129, 69-79, doi:10.1016/j.clim.2008.06.002 (2008).

8 Kobayashi, N., Kobayashi, H., Gu, L., Malefyt, T. & Siahaan, T. J. Antigen-specific suppression of experimental autoimmune encephalomyelitis by a novel bifunctional peptide inhibitor. *J Pharmacol Exp Ther* 322, 879-886, doi:10.1124/jpet.107.123257 (2007).

9 Ridwan, R. et al. Antigen-specific suppression of experimental autoimmune encephalomyelitis by a novel bifunc- 10 Murray, J. S. et al. Suppression of type 1 diabetes in NOD mice by bifunctional peptide inhibitor: modulation of the immunological synapse formation. *Chem Biol Drug Des* 70, 227-236, doi:10.1111/j.1747-0285.2007.00552.x (2007).

11 Manikwar, P. et al. Utilization of I-domain of LFA-1 to Target Drug and Marker Molecules to Leukocytes. *Theranostics* 1, 277-289 (2011).

12 Zimmerman, T. et al. ICAM-1 peptide inhibitors of T-cell adhesion bind to the allosteric site of LFA-1. An NMR characterization. *Chem Biol Drug Des* 70, 347-353, doi: 10.1111/j.1399-3011.2007.00566.x (2007).

13 Stanley, P. & Hogg, N. The I domain of integrin LFA-1 interacts with ICAM-1 domain 1 at residue Glu-34 but not Gln-73. *J Biol Chem* 273, 3358-3362 (1998).

14 Lee, S. J. & Benveniste, E. N. Adhesion molecule expression and regulation on cells of the central nervous system. *J Neuroimmunol* 98, 77-88 (1999).

15 Seidel, M. F., Keck, R. & Vetter, H. ICAM-1/LFA-1 expression in acute osteodestructive joint lesions in collagen-induced arthritis in rats. *J Histochem Cytochem* 45, 1247-1253 (1997).

16 Supersaxo, A., Hein, W., Gallati, H. & Steffen, H. Recombinant human interferon alpha-2a: delivery to lymphoid tissue by selected modes of application. *Pharm Res* 5, 472-476 (1988).

17 Supersaxo, A., Hein, W. R. & Steffen, H. Effect of molecular weight on the lymphatic absorption of water-soluble compounds following subcutaneous administration. *Pharm Res* 7, 167-169 (1990).

18 Annunziato, F., Cosmi, L. & Romagnani, S. Human and murine Th17. *Curr Opin HIV AIDS* 5, 114-119, doi: 10.1097/COH.0b013e32833647c2 (2010).

19 Bruno, V., Battaglia, G. & Nicoletti, F. The advent of monoclonal antibodies in the treatment of chronic autoimmune diseases. *Neurol Sci* 31 Suppl 3, 283-288, doi:10.1007/s10072-010-0382-6 (2011).
20 El-behi, M., Rostami, A. & Ciric, B. Current views on the roles of Th1 and Th17 cells in experimental autoimmune encephalomyelitis. *J Neuroimmune Pharmacol* 5, 189-197, doi:10.1007/s11481-009-9188-9 (2010).
21 Haak, S. et al. IL-17A and IL-17F do not contribute vitally to autoimmune neuro-inflammation in mice. *J Clin Invest* 119, 61-69, doi:10.1172/JCI35997 (2009).
22 Muro, S., Gajewski, C., Koval, M. & Muzykantov, V. R. ICAM-1 recycling in endothelial cells: a novel pathway for sustained intracellular delivery and prolonged effects of drugs. *Blood* 105, 650-658, doi:10.1182/blood-2004-05-1714 (2005).
23 Manikwar, P., Zimmerman, T., Blanco, F. J., Williams, T. D. & Siahaan, T. J. Rapid Identification of Fluorochrome Modification Sites in Proteins by LC ESI-Q-TOF Mass Spectrometry. *Bioconjug Chem* 22, 1330-1336, doi:10.1021/bc100560c (2011).
24 Larche, M. & Wraith, D. C. Peptide-based therapeutic vaccines for allergic and autoimmune diseases. *Nat Med* 11, S69-76, doi:10.1038/nm1226 (2005).
25 Wraith, D. C. Therapeutic peptide vaccines for treatment of autoimmune diseases. *Immunol Lett* 122, 134-136, doi:10.1016/j.imlet.2008.11.013 (2009).

Example 3

Synthesis and Characterization of MOG-IDAC and MOG-PEG-IDAC

The present example describes development of conjugates of antigenic peptides that target the antigen-presenting cells (APC) for modulating subpopulations of T cells from inflammatory phenotype to regulatory/suppressor phenotype. This example demonstrates synthesis and evaluation of the efficacy of bi-functional peptide inhibitors (BPI) and I-domain antigenic-peptide conjugates (IDAC). These molecules are designed to simultaneously target the major histocompatibility complex II (MHC II) and adhesion receptors on APC to inhibit the immunological synapse formation and prevent the activation of T cells.

Examples 1 and 2 above showed that PLP-IDAC can significantly suppress PLP-induced EAE in mice when administered in prophylactic and vaccine-like manners. PLP-IDAC decreases the production of inflammatory cytokines (e.g., IL-17) and increases the production of regulatory cytokines (e.g., IL-10), suggesting a shift in T-cell proliferation from an inflammatory to a regulatory phenotype. An embodiment of an IDAC molecule of the present disclsoure contains multiple antigenic peptides ranging from 4 to 8; this property provides a unique opportunity for simultaneously delivering multiple antigenic peptides from PLP, MOG, and MBP to prevent antigenic spreading in MS. However, in carrying out the evaluation of a multiantigen IDAC molecule, the present example demonstrates that an IDAC molecule with another antigen such as MOG or MBP peptides (i.e., MOG-IDAC or MBP-IDAC) could also suppress EAE effectively. In this study, MOG peptide (i.e., MOG-Cys) was conjugated to the I-domain to make MOG-IDAC and MOG-PEG-IDAC. The synthesis of MOG-IDAC was inefficient, and the amount of product could only be used for chemical and physical characterization; there was not a sufficient amount to carry out animal studies. This inefficiency was believed to be due to the insolubility of the MOG-Cys peptide. Therefore, MOG-Cys peptide was modified to MOG-PEG-Cys peptide with polyethylene glycol groups as a spacer in the linker between the MOG peptide sequence and the Cys residue to increase solubility of the peptide. Conjugation of MOG-PEG-Cys and the I-domain successfully produced MOG-PEG-IDAC. The purpose of the second chapter is to describe the synthesis and characterization of MOG-IDAC and MOG-PEG-IDAC molecules.

IDAC molecules have an advantage of delivering multiple antigens due to multiple conjugations of antigen to the I-domain protein [25]. Since the above example demonstrated the synthesis and effectiveness of PLP-IDAC molecules, the present example explored the possibility of conjugating several $MOG_{(38-50)}$ peptides to the I-domain to make MOG-IDAC or MOG-PEG-IDAC molecules for potential evaluation of their efficacies in MOG-stimulated EAE. Thus, the MOG-IDAC and MOG-PEG-IDAC were synthesized by conjugating the multiple MOG-Cys and MOG-PEG-Cys to gamma-maleimido-butyramide (GMB) groups on the lysine residues of the I-domain protein. The resulting MOG-IDAC or MOG-PEG-IDAC was purified using size exclusion chromatography and characterized using SDS-PAGE, mass spectrometry and circular dichroism (CD) spectroscopy.

Experimental Procedures

Materials

Amino acids used in peptide synthesis were purchased from Peptide International Inc. (Louisville, Ky.). GMBS (N-[γ-maleimidobutryloxy]succinimide ester) was purchased from Pierce Inc. (Rockford, Ill.). All other chemicals and solvents used were of analytical grade.

Peptide Synthesis

The MOG-Cys (Ac-GWYRSPFSRVVHLC-NH$_2$) [Ac-(SEQ ID NO: 4)-NH$_2$] and MOG-PEG-Cys (Ac-GWYR-SPFSRVVHL-Peg-C—NH$_2$) [Ac-(SEQ ID NO: 3)-Peg-C—NH$_2$] peptides were synthesized with automated peptide synthesizer (Pioneer; Perceptive Biosystems, Framingham, Mass.) using Fmoc chemistry as previously described (see reference [2]). After peptide cleavage from the resin using trifluoroacetic acid (TFA), the crude peptides were purified by reversed-phase high performance liquid chromatography (HPLC) on a semi-preparative C18 column with a gradient of solvent A (94.9% H$_2$O, 5% Acetonitrile, 0.1% TFA) and solvent B (100% acetonitrile). Analytical HPLC was used to determine the purity of each peptide fraction collected from a semi-preparative HPLC. Fractions that showed high purity were then pooled together and lyophilized. ESI mass spectrometry indicated that the pure MOG-Cys (M+H=1748.075) and MOG-PEG-Cys (M+H=2126.39) have the correct molecular weights.

Preparation of the I-Domain

The I-domain protein was previously overexpressed, refolded, and purified using methods described in earlier work [27]. The purity and structural properties of the I-domain protein were evaluated by mass spectrometry, SDS-PAGE, and CD.

Synthesis of MOG-IDAC and MOG-PEG-IDAC

Figure 18:
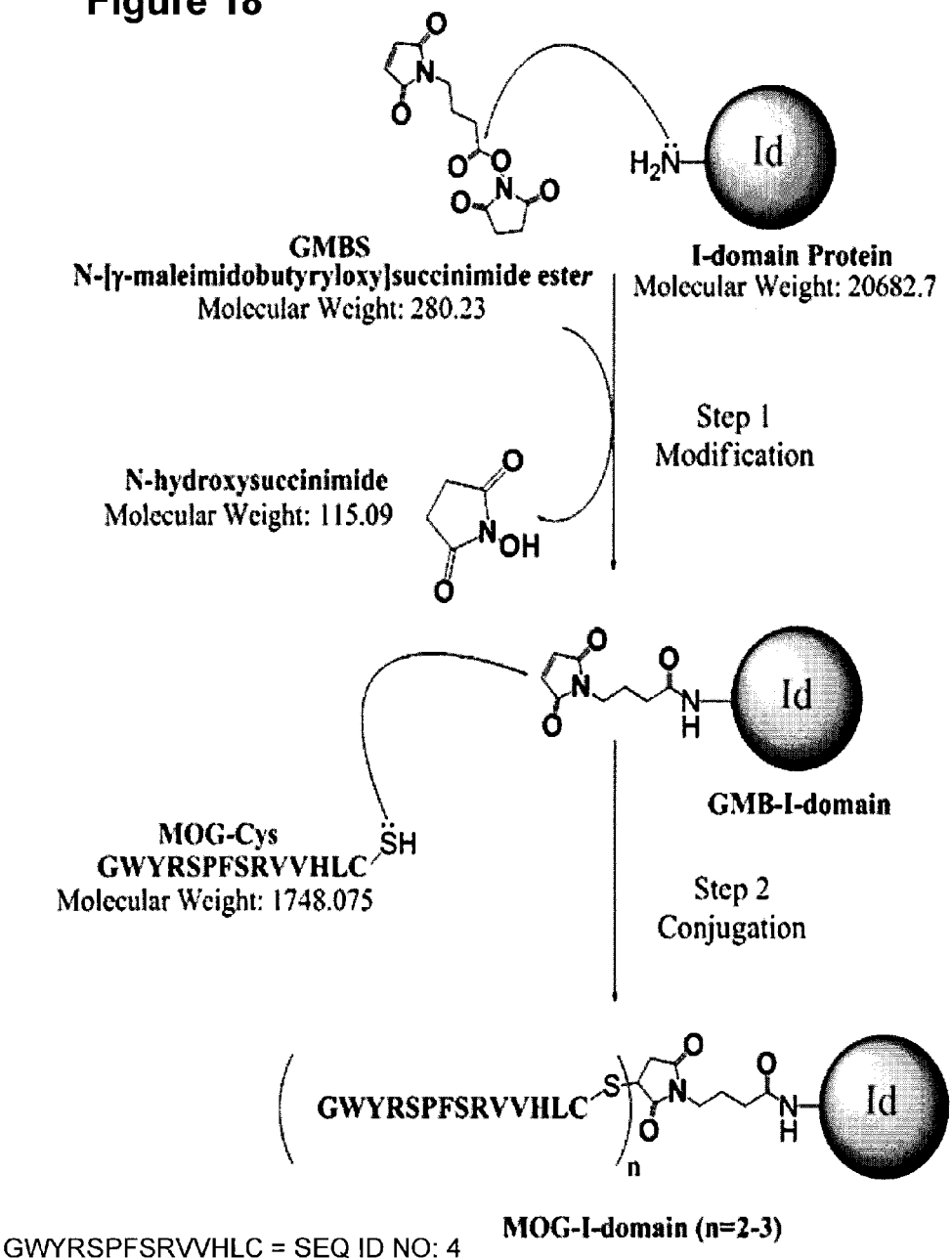
FIG. 18 illustrates the reaction steps used to make MOG-IDAC or MOG-PEG-IDAC. The first step is to derivatize the lysine residues on the 1-domain to gamma-maleimido-butyramide (GMB) groups. Then in step 2, the maleimide groups are reacted with the thiol group of the cysteine residue on the MOG peptide to produce the desired conjugates.

The MOG-IDAC and MOG-PEG-IDAC were synthesized via the formation GMB-I-domain, which was synthesized by reacting several lysine residues with N-[γ-maleimidobutyryloxy]-succinimide ester (GMBS) (FIG. 18). In this case, the 1-domain protein (20 mg) was dissolved in 10 ml of buffer (2 mg/ml) followed by drop-wise addition of 10 fold molar excess of GMBS in 500 μl of DMSO. The mixture was stirred for 1 h at 24° C. in the absence of light and the crude GMB-I-domain was purified using a Superdex 75 size exclusion chromatography (SEC) column in PBS containing 10 mM MgSO$_4$. After combining all SEC fractions containing GMB-I-domain, the solution was concentrated using ultrafiltration. The number of GMB group per I-domain molecules was determined by MALDI-TOF mass spectrometry.

To complete the synthesis of MOG-IDAC or MOG-PEG-IDAC, the maleimide groups on the GMB-I-domain were reacted with the thiol group of MOG-Cys or MOG-PEG-Cys. In this reaction, 15 fold molar excess of the peptide (MOG-Cys or MOG-PEG-Cys) was added drop-wise into a solution of GMB-I-domain (2.0 mg/ml) at pH 7.5; then, the reaction was carried out for 1 hour at 24° C. with constant stirring under dark conditions. The resulting MOG-IDAC or MOG-PEG-IDAC was purified on a Superdex 75 size exclusion column and eluted with PBS containing 10 mM MgSO$_4$. The fractions containing the MOG-IDAC or MOG-PEG-IDAC were collected and concentrated by ultrafiltration and the number of peptides conjugated to the 1-domain was determined by MALDI-TOF mass spectrometry. The purity of the IDAC molecules was confirmed by SDS-PAGE gel and size-exclusion chromatography. The secondary structure was confirmed by far-UV CD and compared to the parent GMB-I-domain and 1-domain.

Gel Electrophoresis

The purity of protein solution of 1-domain, GMB-I-domain, MOG-IDAC, MOG-PEG-IDAC obtained from SEC separation was analyzed by SDS-PAGE. Approximately 100 μg of protein in solution was mixed with 4× Tris-glycine SDS sample buffer without reducing agent and loaded into 1.5 mm thick 10 well NuPAGE Novex 4-12% Bis-Tris gradient gel. The gel was ran for 1 h at 150 V, then was stained with 0.25% Coomassie blue R250 solution (10% acetic acid, 50% ethanol, 40% water) for 30 min followed by destaining (10% acetic acid, 25% ethanol, 65% water) until the bands were visible and the background was completely clear.

Results

Conjugation of GMBS to I-Domain

Figure 19:
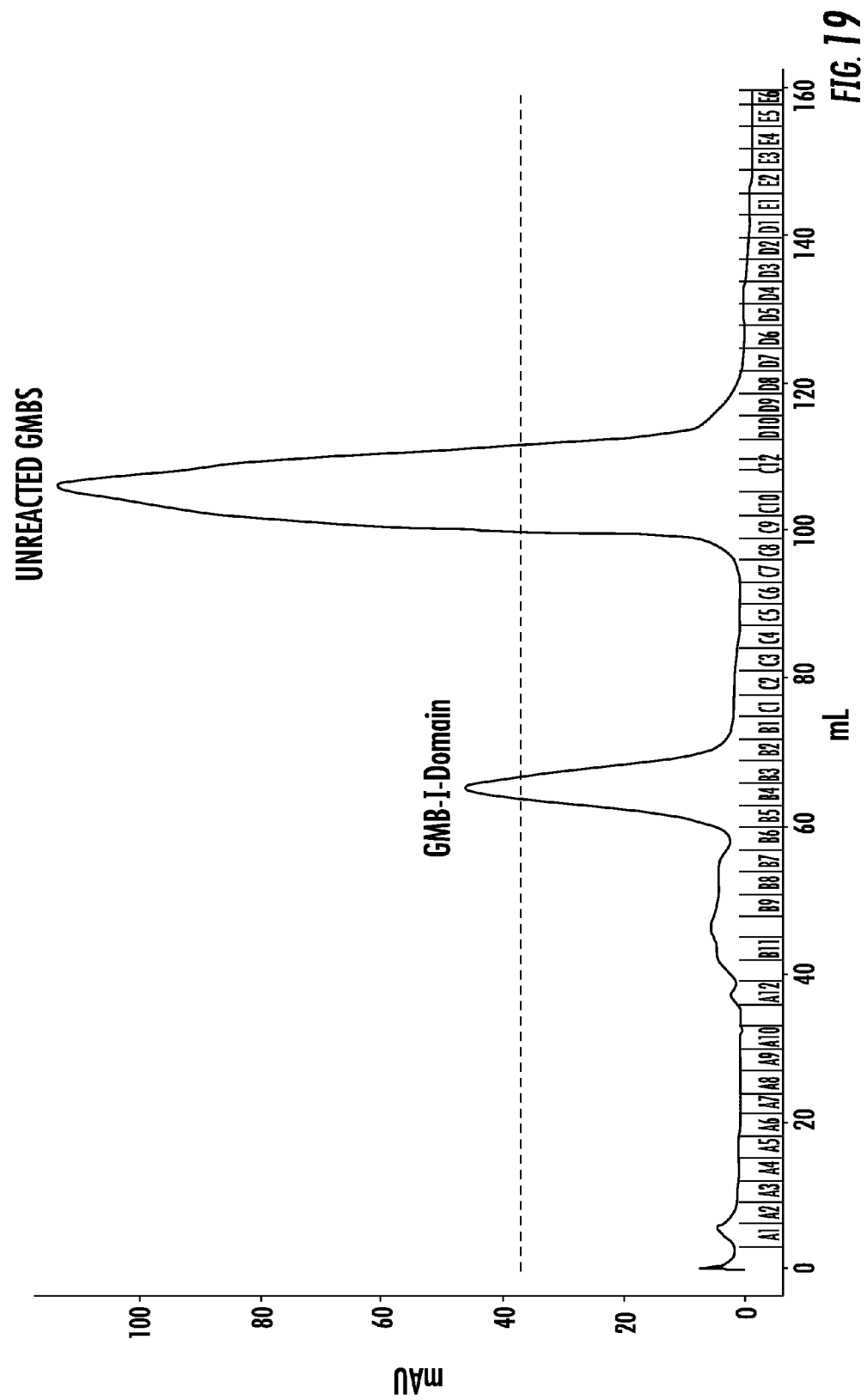
FIG. 19 is a SEC Chromatogram showing the separation between GMB-I-domain and unreacted GMBS. The crude reaction of reaction between GMBS and I-domain was purified using Superdex 75 column eluted with PBS with 10 mM $MgSO_4$.
Figure 20:
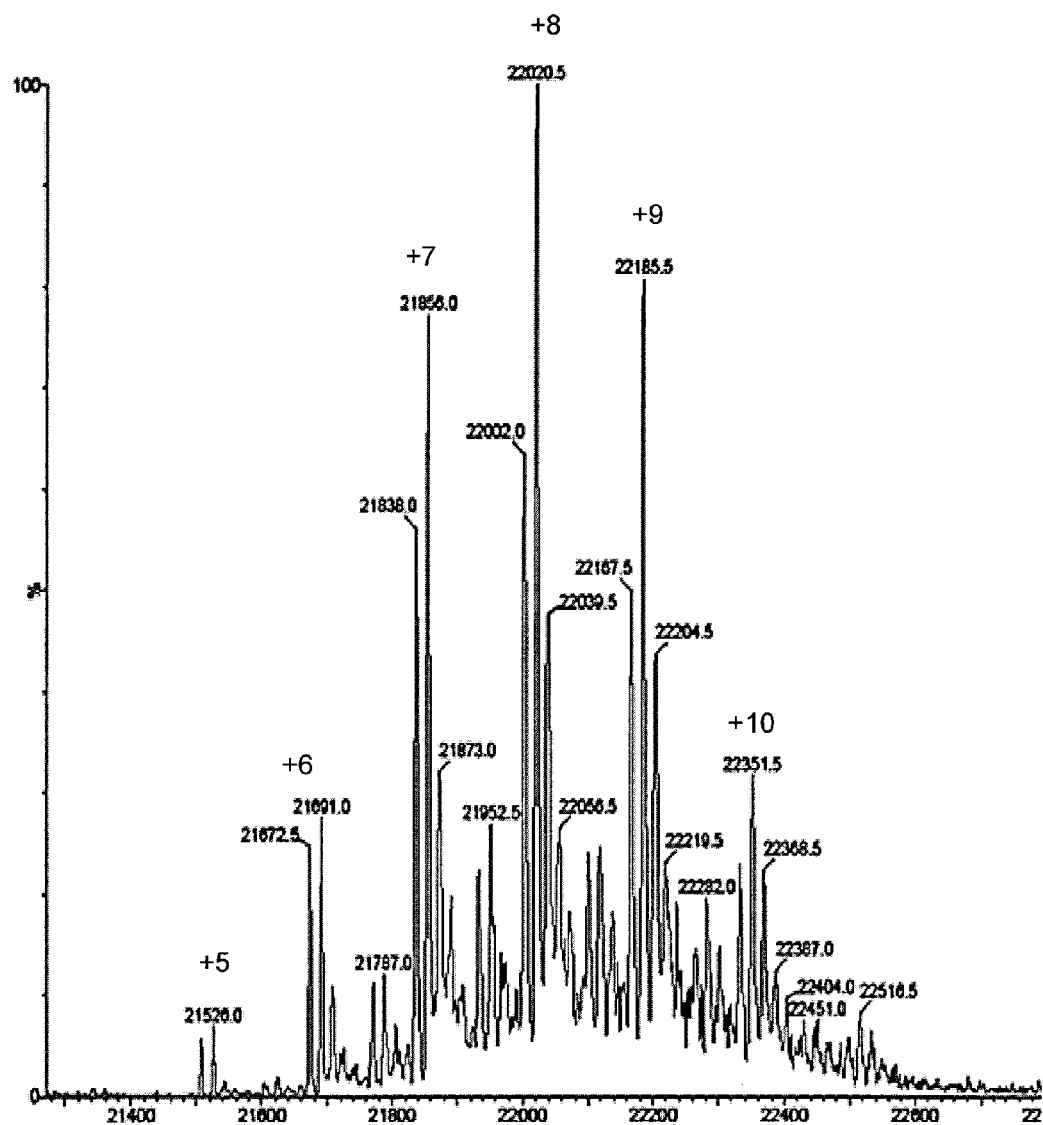
FIG. 20 is a MALDI-TOF mass spectrum of GMB-I-domain protein. The conjugates contain 5 to 10 GMB groups per I-domain molecule.

The formation of GMB-I-domain was very efficient and it can readily be separated from the unreacted GMBS using SEC (FIG. 19). The pure GMB-I-domain has 5 to 10 GMB groups attached per I-domain molecule as determined by MALDI-TOF mass spectrometry (FIG. 20). The parent I-domain with a molecular weight of 20,682 Da (previous data) [25] was not observed in the MS spectra of the GMB-I-domain conjugates. The mass spectrometry demonstrated multiple conjugates of GMB to I-domain protein with molecular weights of 21,526 Da, 21,691 Da, 21,856 Da, 22,020 Da, 22,185 Da, 22,351 Da with a difference of 165 Da for a GMB group (FIG. 20). The first peak with 21,526 Da was from GMB-I-domain with 5 GMB groups; thus, the remaining peaks correspond to GMB-I-domain with 6 to 10 GMB groups, respectively. The mass spectrum of GMB-I-domain also produced peaks with corresponding peaks of 18 Da mass increased (FIG. 20), which were due to the hydrolysis of the attached maleimide groups.

Figure 21:
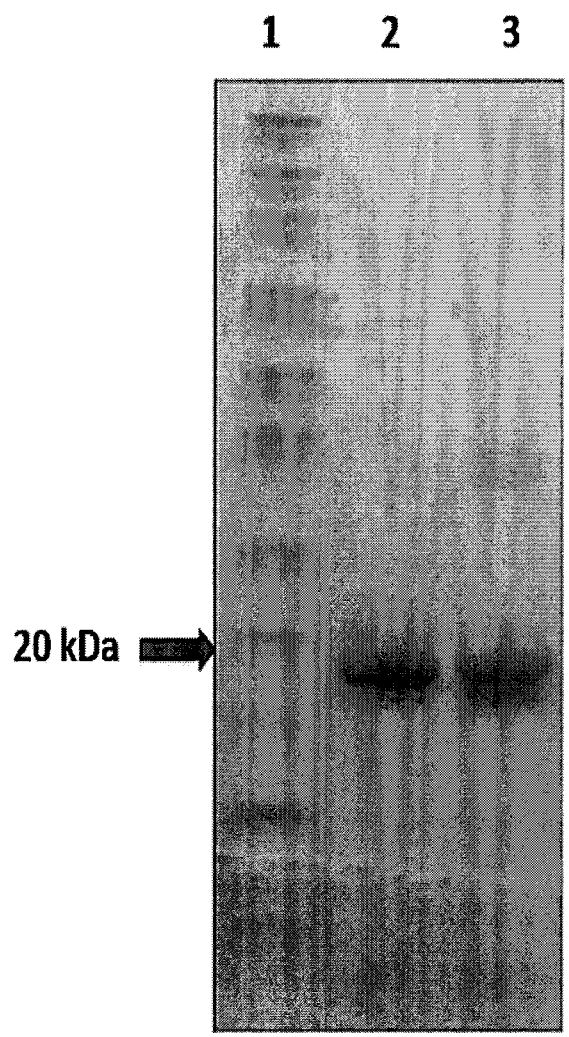
FIG. 21 is a digital image illustrating SDS-PAGE analysis of pure GMB-I-domain compared to the I-domain protein after SEC purification. The gel was stained with staining Coomassie blue: lane 1 for marker molecules, lane 2, for I-domain, and lane 3 for GMB-I-domain.
Figure 22:
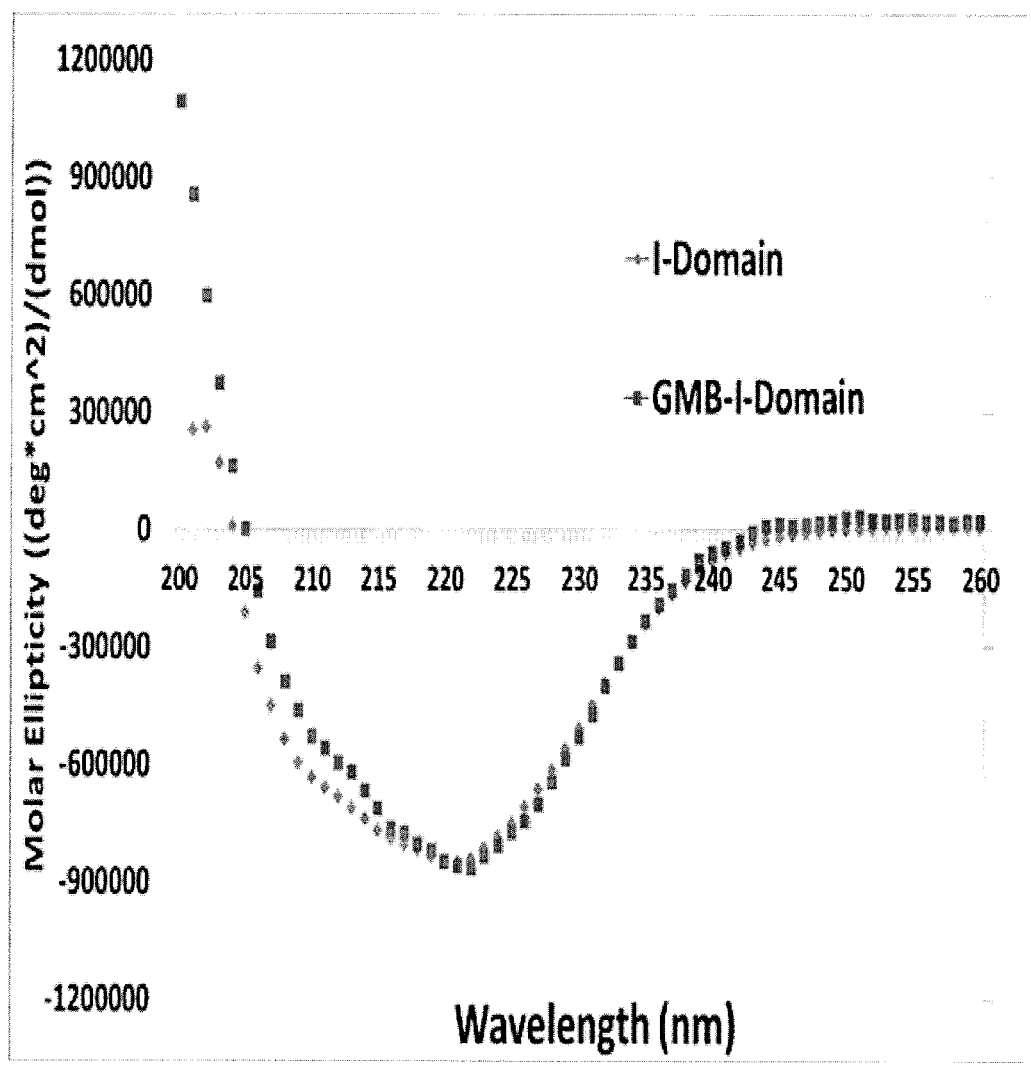
FIG. 22 is a CD Spectra of GMB-I-Domain. GMB-I-domain (diamond) has similar CD spectrum to the parent I-domain (square).

These results are consistent with the SDS PAGE gel that indicates two bands of the desired maleimide conjugate and maleic acid derivatives, which have different electrophoretic mobility (FIG. 21, lane 3). In the case of the parent I-domain, only one band appears on the gel (FIG. 21, lane 2). The formation of hydrolysis products from the GMB-I-domain increases upon storage, so the GMB-I-domain should be used for the next conjugation reaction within 48 hours of SEC purification. In order to better understand the structure of the GMB-I-domain conjugate the secondary structure of GMB-I-domain was compared to the I-domain using CD spectroscopy (FIG. 22) and both molecules have similar secondary structure.

Synthesis of MOG-IDAC

Figure 23:
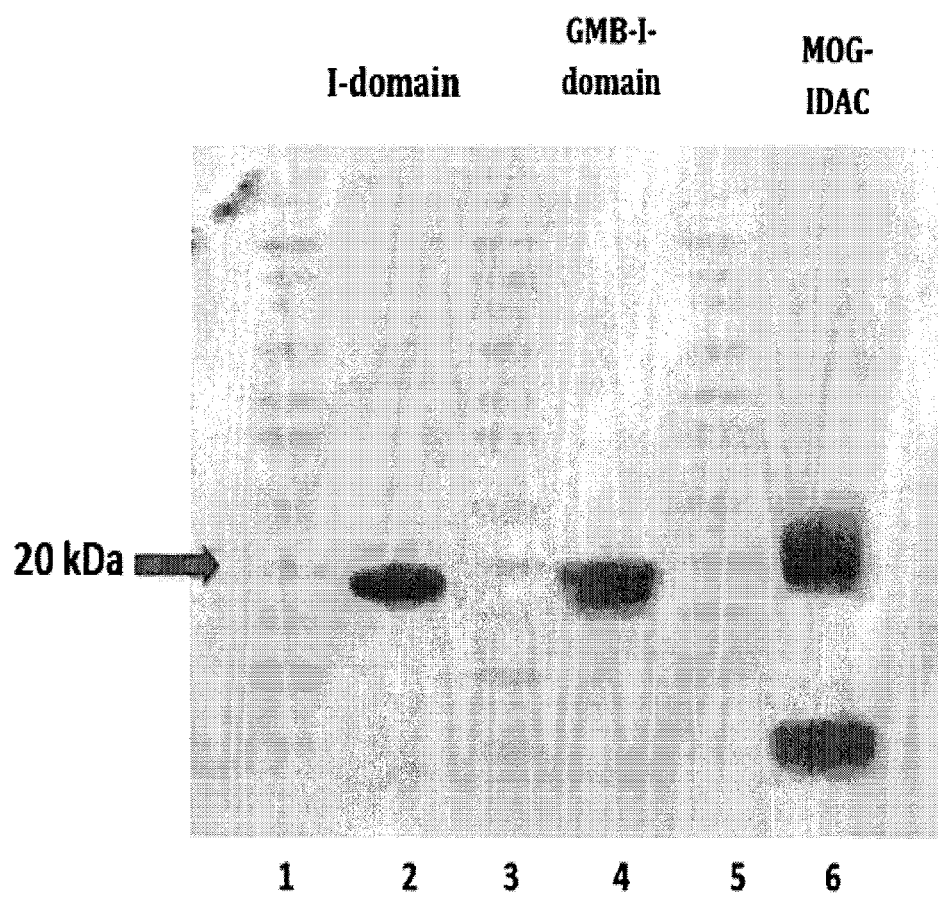
FIG. 23 is a digital image illustrating the SDS-PAGE of the crude reaction to make MOG-IDAC (lane 6), compared to GMB-I-domain (lane 4) and I-domain (lane 2). In lane 6, the MOG-IDAC shows multiple products around 20 kDa with different number of conjugated peptides. The crude also shows peptide band at a low molecular weight.

MOG-IDAC was synthesized by conjugating MOG-Cys to the GMB-I-domain at pH 7.5 using previously described method [25]. MOG-Cys is the MOG$_{(38-50)}$ peptide with an additional cysteine amino acid at the C-terminus and the peptide was also amidated and acetylated at the N- and C-terminus. The peptide conjugation is via nucleophilic attack on the maleimide groups of the GMB-I-domain by the thiol group of the Cys residue on MOG-Cys (Step 2, FIG. 18). The crude sample of the MOG-IDAC was analyzed by SDS-PAGE against the parent I-domain and GMB-I-domain (FIG. 23). The gel of the crude product of MOG-IDAC (lane 6, FIG. 23) shows multiple bands at around 20 kDa, indicating the protein is a mixture of conjugates different amount of conjugated peptides. Lane 6 also illustrates the presence of a lower MW bands corresponding to excess MOG-Cys peptide. The parent I-domain (lane 2) shows one single band with lower molecular weight than GMB-I-domain (lane 4) and MOG-IDAC (lane 6).

Figure 24:
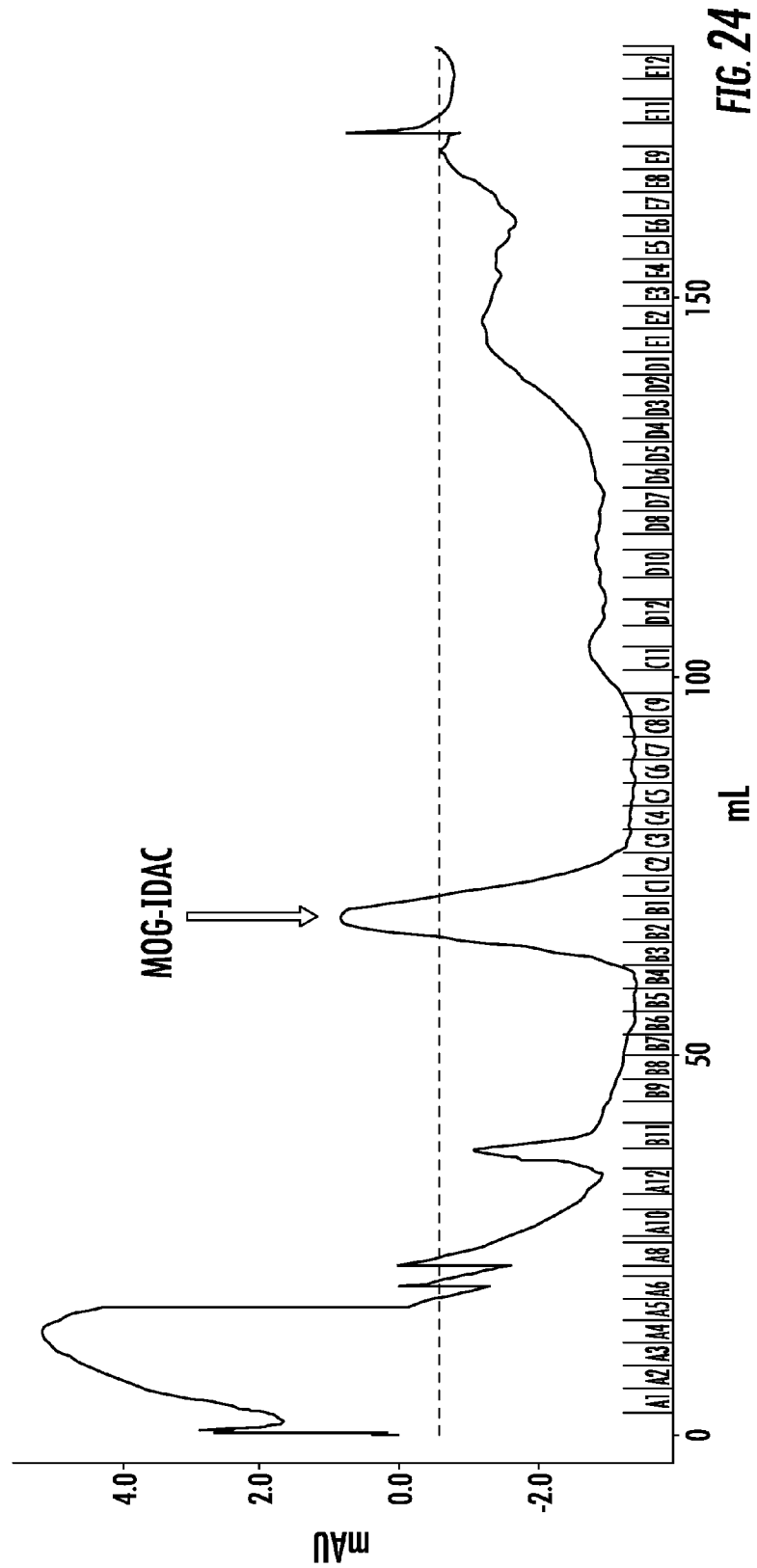
FIG. 24 is an analytical SEC chromatogram of MOG-IDAC after purification using Superdex 75 column eluted with PBS with 10 mM $MgSO_4$. The chromatogram did not show any peak for the left over MOG-Cys peptide.
Figure 25:
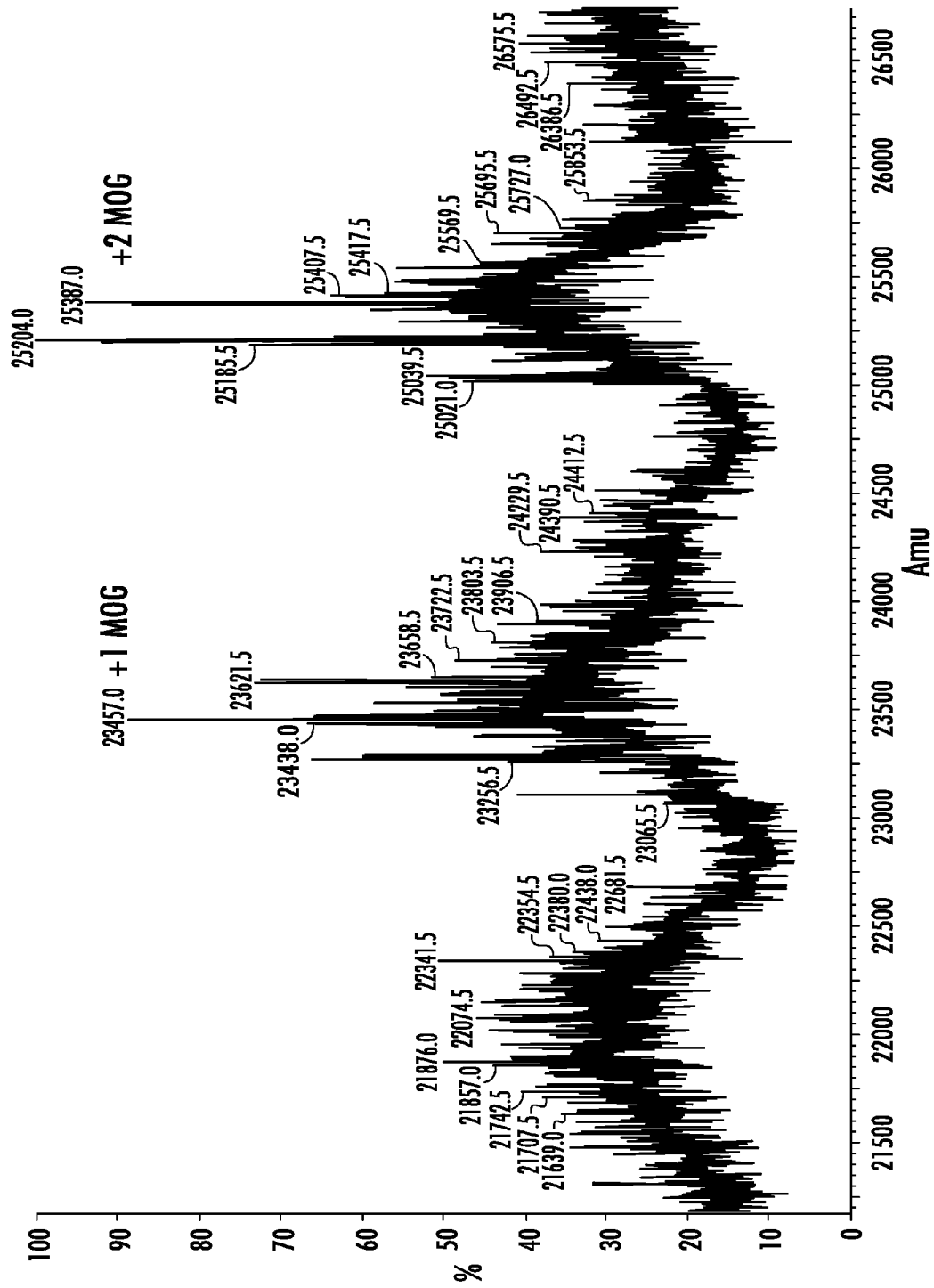
FIG. 25 illustrates a MALDI-TOF mass spectrum of MOG-IDAC conjugates with one or two peptides per molecule I-domain.
Figure 26:
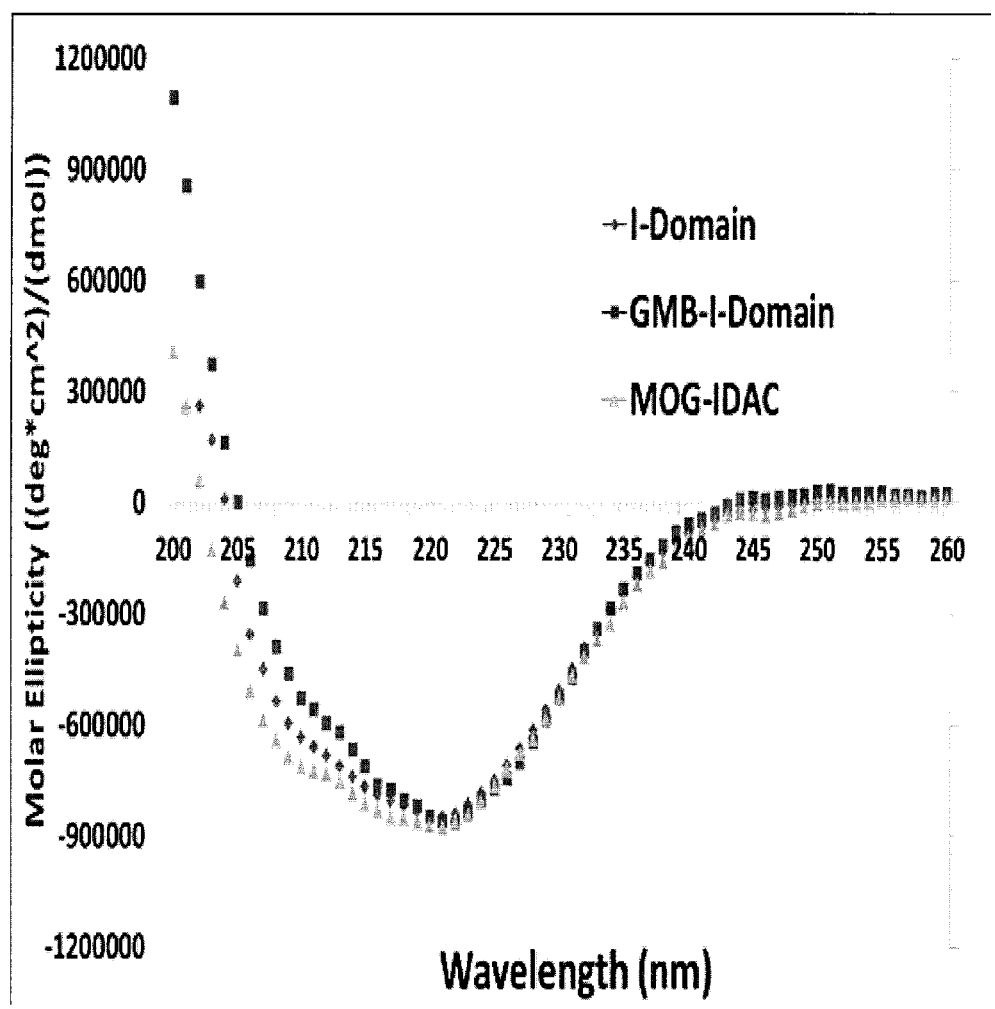
FIG. 26 is a graph illustrating a comparison of CD spectra of parent I-domain (diamond), GMB-I-domain (square), and MOG-IDAC (triangle). The spectrum of MOG-IDAC was not dramatically altered upon peptide conjugation, suggesting that the I-domain in the conjugate maintains its secondary structure.

The reaction mixture was purified through SEC and the eluted fractions of desired pure MOG-IDAC were pooled and concentrated. Unlike the SDS-PAGE of the crude product, the pure fraction shows a single peak at the desired product without the presence of MOG-Cys peptide peak (FIG. 24). The pure product was subjected to MALDI-TOF MS analysis and multiple peaks were observed to indicate 1 to 2 of MOG-Cys peptides conjugated to a molecule of 1-domain (FIG. 25). Finally, the CD spectrum of MOG-IDAC was compared to GMB-I-domain and parent I-domain (FIG. 26) and the results confirm that MOG-IDAC has similar secondary structure with GMB-I-domain and I-domain.

Synthesis of MOG-PEG-IDAC

Figure 27:
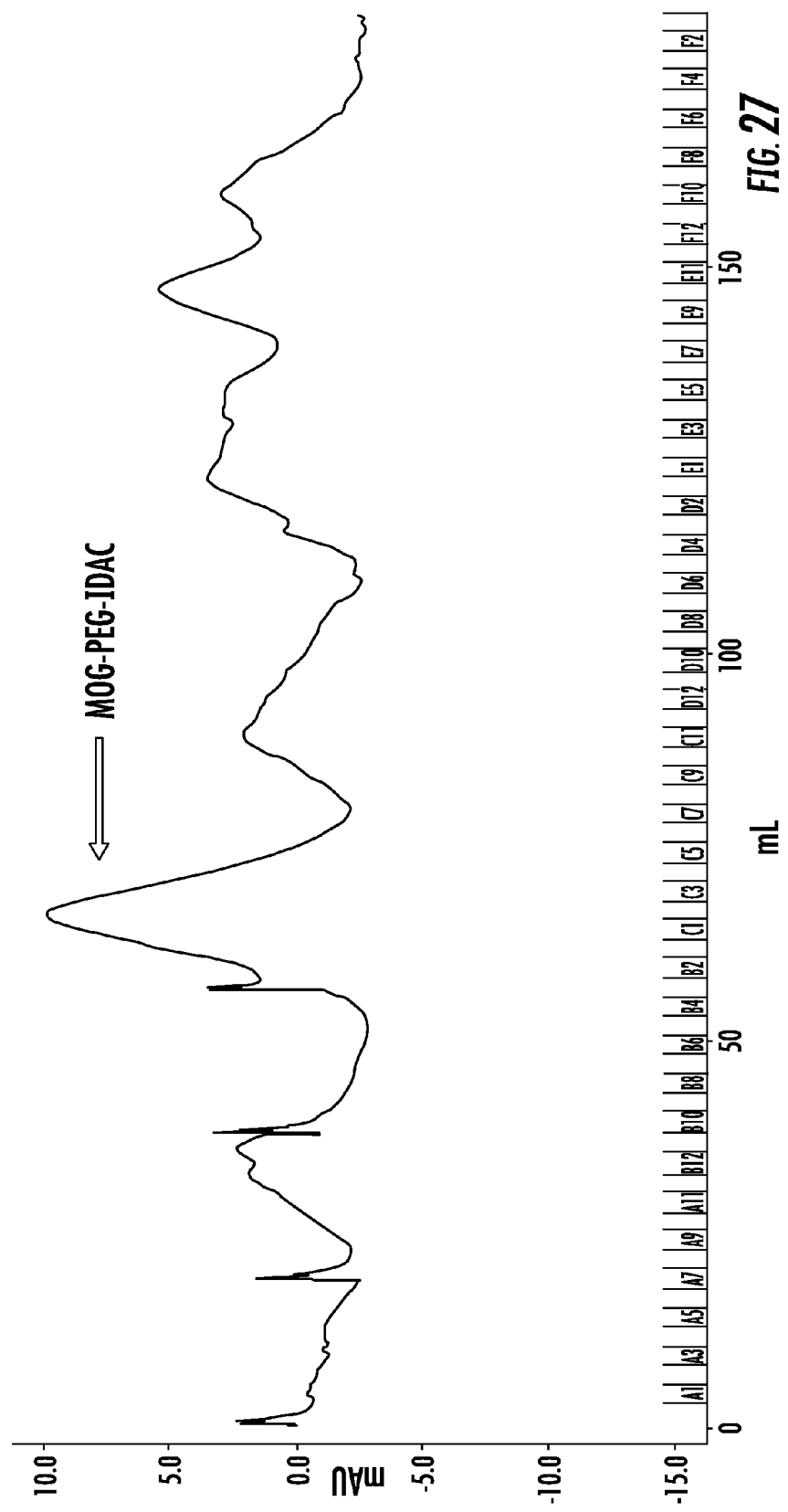
FIG. 27 illustrates the SEC chromatogram of MOG-PEG-IDAC. The conjugate appears in a single peak; however, conjugation still yields some protein precipitation, causing a somewhat low absorbance reading of MOG-PEG-IDAC in UV detection during SEC.
Figure 28:
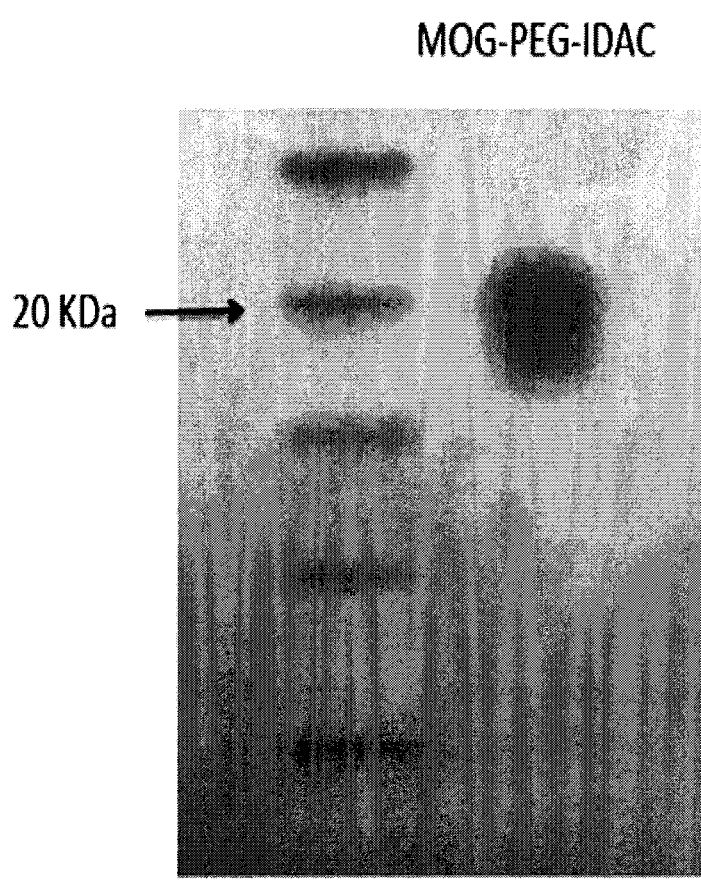
FIG. 28 is a digital image of a SDS PAGE of MOG-PEG-IDAC showing a broad band of the desired product without the presence of precursor MOG-PEG-Cys peptide.
Figure 29:
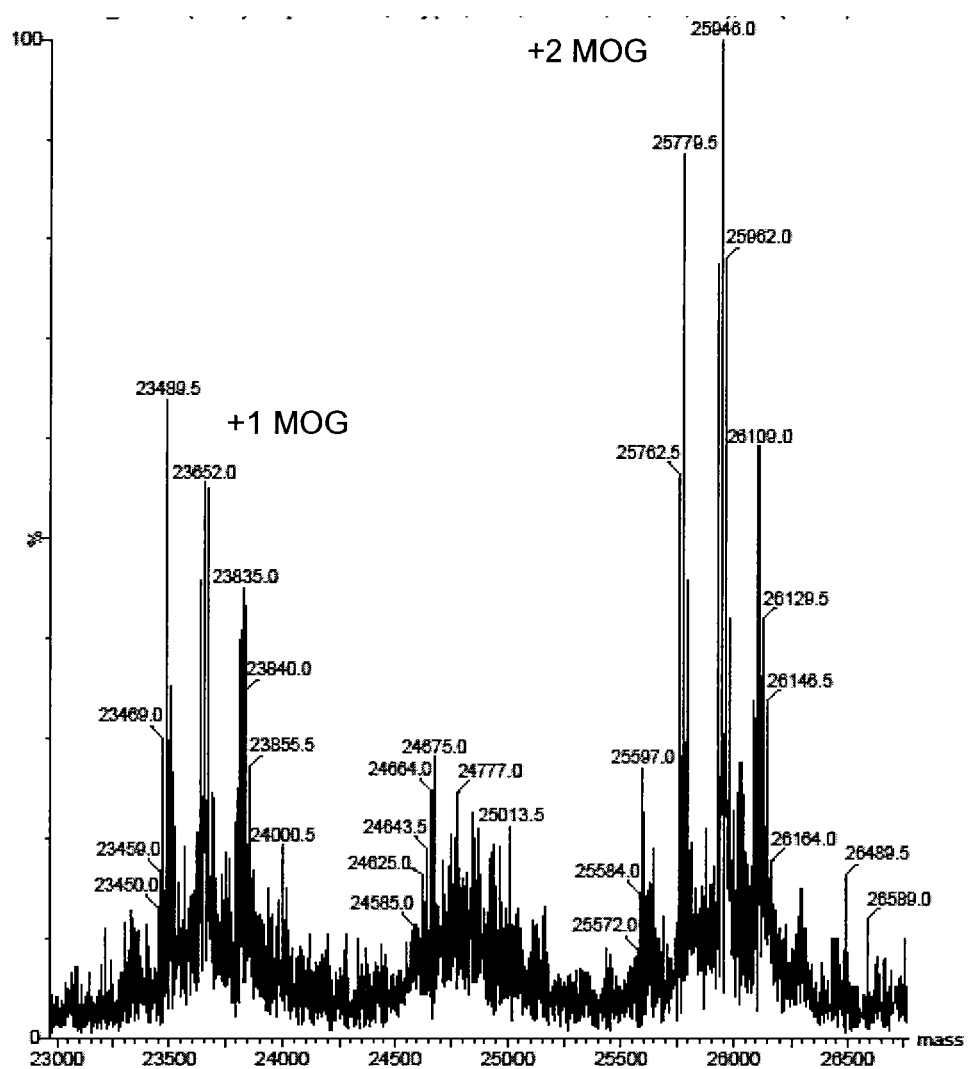
FIG. 29 illustrates a mass spectrum of MOG-PEG-IDAC indicating that there are one to two peptides conjugated to the I-domain.
Figure 30:
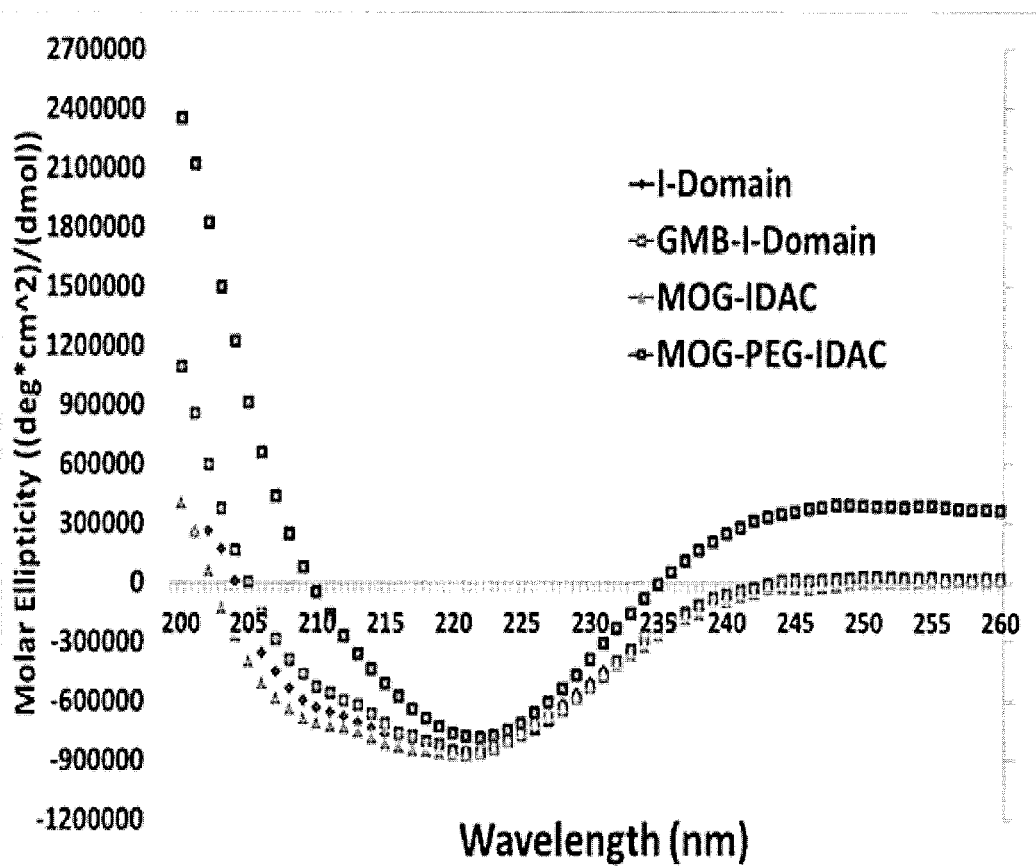
FIG. 30 illustrates the CD spectra of parent I domain (diamond), GMB-I-Domain (square), MOG-IDAC (triangle), MOG-PEG-IDAC (X-square). There is a significant change in the CD spectrum of MOG-PEG-IDAC, suggesting there is some alteration of the secondary structure of the conjugate.

During synthesis of the MOG-IDAC molecule it was found that the MOG peptide had low solubility limiting the conjugation efficiency. In an attempt to increase the solubility of the peptide, two poly-ethylene glycol amino acids (i.e., 11-amino-3,6,9-trioxaundecanoic acid) were inserted between the C-terminus of the MOG peptide and the cysteine C-terminal amino acid to give MOG-PEG-Cys peptide. Conjugation of the MOG-PEG-Cys to GMB-I-Domain was completed in the same manner as MOG-IDAC; the reaction yielded the MOG-PEG-IDAC conjugate. The molecule was purified with SEC (FIG. 27) and SDS-PAGE of the pure product of MOG-PEG-IDAC shows a broad band similar to that of MOG-IDAC (FIG. 28). The number of conjugated peptide was determined by MALDI-TOF MS (FIG. 29), and there are 1 to 2 conjugated peptides per one molecule of I-domain. CD spectral analysis was carried out to compare the secondary structure of MOG-PEG-IDAC to MOG-IDAC, GMB-I-domain and 1-domain (FIG. 30). There appears to be a change in the secondary structure of MOG-PEG-IDAC compared to that of MOG-IDAC.

Discussion

Today, patients with autoimmune diseases such as rheumatoid arthritis, multiple sclerosis, and psoriasis are currently being treated with protein derived drugs such as peptide and monoclonal antibodies to modulate their immune systems. Multiple sclerosis patients are currently being treated with Copaxone® and Tysabri®, along with other anti-inflammatory agents (e.g., mitoxantrone, and Beta-interferon 1a). One common monoclonal antibody treatment is Tysabri, which binds to the α4 subunit of the α4β1 and α4β7 integrins on the surface of leukocytes.

Blocking of the α4 subunit prevents leukocyte adhesion to endothelial cells and subsequent infiltration of T cells and other immune cells into the CNS. Unfortunately, some patients treated with Tysabri have develop progressive multifocal leukoencephalopathy (PML) conditions, a life threatening complication with no available cure [14]. A monoclonal antibody, Raptiva (Efalizumab, CD11a mAB) for cell adhesion molecules has been used to treat psoriasis, but due to PML complications, this drug was withdrawn from the U.S. market [28, 29]. In addition to blocking T-cell adhesion to endothelial cells, Tysabri and Raptiva can also block signal 2 recognition between the APC and T-cell. As a result, it may cause a general suppression of T-cell activation and prevents T-cells from responding to pathogens like JC virus, which is responsible for the appearance of PML. With this knowledge, there is a need to develop a new therapy that does not suppress the general immune response but is more specific to regulating a certain population of immune cells.

To generate a more antigen-specific immune suppression, one approach has been to develop BPI molecules such as PLP-BPI, GAD-BPI, and CII-BPI that suppress MS, Type 1 Diabetes, and rheumatoid arthritis in animal models [2, 17, 20-22]. In conjunction with the BPI molecules, PLP-IDAC molecules were also developed with several antigenic PLP peptides to a single I-domain [25]. Following induction with one antigen, the disease could exacerbate to include multiple antigens, a phenomenon termed "antigenic spreading" [30]. Since the IDAC molecules of the present disclsoure can deliver multiple and different antigenic peptides from different myelin sheath proteins (i.e., PLP, MOG, and MBP) their use may help in slowing and/or preventing antigenic spreading in autoimmune diseases. Thus, it may provide a unique approach to treating MS and another autoimmune disorders. Another advantage is that both BPI and IDAC molecules can suppress the disease when administered as "vaccine like" treatments; in this case, the molecules are delivered several days before induction of the disease [25]. The proposed mechanism of action of PLP-IDAC molecules is similar to that of BPI molecule in which they inhibit the formation of the immunological synapse by simultaneous binding to ICAM-1 and MHC-II on the surface of APC. This inhibition prevents the activation of T cell and/or alters the differentiation of inflammatory to regulatory T cells.

Although MOG-IDAC was successfully produced, the production yield was lower than desired and was not sufficient quantity for animal studies. However, the amount was sufficient to characterized the molecules by SDS-PAGE, mass spectrometry, and CD spectroscopy [25]. Due to the low solubility of MOG-Cys peptide, MOG-Cys peptide was dissolved in DMSO before adding to the reaction mixture for conjugation. This conjugation reaction was less efficient than conjugation between PLP-Cys and GMB-I-domain to make PLP-IDAC as in Example 1. Different reaction conditions were explored including changing the pH and buffers to improve the efficiency of the reaction; unfortunately, these changes did not change reaction efficiency sufficiently to make MOG-IDAC. The best reaction condition was by adding the dissolved MOG peptide in DMSO drop wise to the GMB-I-domain reaction mixture. At pH 7.4, the reaction mixture still produces slight cloudiness in the solution; however, upon filtration, the filtrate showed successful conjugation in SEC. This inefficiency was also reflected by the low number of peptides conjugated to the I-domain in MOG-IDAC compared to PLP-IDAC. It should be noted that the PLP-IDAC had about five peptides per-molecule of I-domain. It is interesting to find that adding MOG peptides did not dramatically alter the CD spectra MOG-IDAC compared to the I-domain, suggesting that the MOG peptide has low contribution to the secondary structure of the conjugates.

Due to the difficulty of producing sufficient quantity, the animal studies were not carried out with MOG-IDAC. To improve the synthesis of the conjugate, solubility of the peptide was improved by adding PEG groups between MOG peptide and the cysteine residue to make MOG-PEG-Cys. It has been shown that PEGylation of proteins and peptides improves the biopharmaceutical properties, through increase in solubility, increase in half-life, and decrease in immunogenicity [31, 32]. PEGylation has been shown to be safe and non-toxic. For example, certolizumab pegol is a TNFα antibody; this molecule is a humanized Fab' antibody fragment conjugated to PEG to increase the half-life and decrease immunogenicity [33]. This drug has been used in the clinic for the treatment of RA. Our group had also utilized PEG group as a linker to make PLP-PEG-BPI and the use of PEG in PLP-PEG-BPI lowered the anaphylaxis incidence compared to PLP-BPI molecules in the EAE mouse model [21]. Besides increasing solubility, the hope is that adding PEG groups as a linker could also lower the toxicity profile (i.e., anaphylaxis reaction) of MOG-PEG-IDAC [25]. Although some precipitation was still observed during conjugation reaction at neutral pH, enough MOG-PEG-IDAC could be synthesized for animal studies (see Example 4, below). The secondary structure of MOG-PEG-IDAC was also altered to increase the beta-sheet structure compared to the MOG-IDAC and the I-domain as shown in the CD spectra (FIG. 30). The beta-sheet structure in the MOG-PEG-IDAC may lead to aggregation of the conjugate, contributing to the insolubility of the MOG-PEG-IDAC. It is not clear whether the increase in beta sheet structure is due to the contribution of the MOG peptide to the secondary structure of the conjugate or it is due to the change of random coil or alpha helix structure to beta sheet within the I-domain protein of the conjugate.

In conclusion, the present example demonstrates production of a new IDAC molecule (MOG-IDAC and MOG-PEG-IDAC) and successfully purification and characterization it using SEC, SDS-PAGE, Mass Spectrometry, and CD.

Example 3 References

1. Fletcher J M, Lalor S J, Sweeney C M, Tubridy N, Mills K H. T cells in multiple sclerosis and experimental autoimmune encephalomyelitis. Clin Exp Immunol. 2010; 162: 1-11.
2. Kobayashi N, Kobayashi H, Gu L, Malefyt T, Siahaan T J. Antigen-specific suppression of experimental autoimmune encephalomyelitis by a novel bifunctional peptide inhibitor. J Pharmacol Exp Ther. 2007; 322: 879-886.
3. Serafini B, Severa M, Columba-Cabezas S, Rosicarelli B, Veroni C, Chiappetta G, Magliozzi R, Reynolds R, Coccia E M, Aloisi F. Epstein-Barr virus latent infection and BAFF expression in B cells in the multiple sclerosis brain: implications for viral persistence and intrathecal B-cell activation. J Neuropathol Exp Neurol. 2010; 69: 677-693.
4. Ebers G C. Environmental factors and multiple sclerosis. Lancet Neurology. 2008; 7: 268-277.
5. Haines J L, Ter-Minassian M, Bazyk A, Gusella J F, Kim D J, Terwedow H, Pericak-Vance M A, Rimmler J B, Haynes C S, Roses A D, Lee A, Shaner B, Menold M, Seboun E, Fitoussi R P, Gartioux C, Reyes C, Ribierre F, Gyapay G, Weissenbach J, Hauser S L, Goodkin D E, Lincoln R, Usuku K, Oksenberg J R, et al. A complete genomic screen for multiple sclerosis underscores a role for the major histocompatability complex. The Multiple Sclerosis Genetics Group. Nat Genet. 1996; 13: 469-471.
6. Mohr D C, Hart S L, Julian L, Cox D, Pelletier D. Association between stressful life events and exacerbation in multiple sclerosis: a meta analysis. British Medical Journal. 2004; 328: 731-736.
7. Whitacre C C. Sex differences in autoimmune disease. Nat Immunol. 2001; 2: 777-780.
8. Manikwar P, Kiptoo P, Badawi A H, Buyuktimkin B, Siahaan T J. Antigen-specific blocking of CD4-specific immunological synapse formation using BPI and current therapies for autoimmune diseases. Med Res Rev. 2012; 32: 727-764.
9. Matsushita T, Yanaba K, Bouaziz J D, Fujimoto M, Tedder T F. Regulatory B cells inhibit EAE initiation in mice while other B cells promote disease progression. J Clin Invest. 2008; 118: 3420-3430.
10. Kappos L, Antel J, Comi G, Montalban X, O'Connor P, Polman C H, Haas T, Korn A A, Karlsson G, Radue E W. Oral fingolimod (FTY720) for relapsing multiple sclerosis. New Engl J Med. 2006; 355: 1124-1140.
11. Arnon R. The development of Cop 1 (Copaxone®), and innovative drug for the treatment of multiple sclerosis personal reflections. Immunol Lett. 1996; 50: 1-15.
12. Marriott J J, Miyasaki J M, Gronseth G, O'Connor P W. Evidence Report: The efficacy and safety of mitoxantrone (Novantrone) in the treatment of multiple sclerosis. Report of the Therapeutics and Technology Assessment Subcommittee of the American Academy of Neurology. Neurology. 2010; 74: 1463-1470.
13. Cadavid D, Wolansky L J, Skurnick J, Lincoln J, Cheriyan J, Szczepanowski K, Kamin S S, Pachner A R, Halper J, Cook S D. Efficacy of treatment of MS with IFN beta-1b or glatiramer acetate by monthly brain MRI in the BECOME study. Neurology. 2009; 72: 1976-1983.
14. Goodin D S, Cohen B A, O'Connor P, Kappos L, Stevens J C. Assessment: The use of natalizumab (Tysabri) for the treatment of multiple sclerosis (an evidence-based review)—Report of the therapeutics and technology assessment subcommittee of the American Academy of Neurology. Neurology. 2008; 71: 766-773.
15. Kress-Bennett J M, Ehrlich G D, Bruno A, Post J C, Hu F Z, Scott T F. Preliminary study: treatment with intramuscular interferon beta-1a results in increased levels of IL-12Rbeta2+ and decreased levels of IL23R+CD4+T—Lymphocytes in multiple sclerosis. BMC Neurol. 2011; 11: 155.
16. Badawi A H, Kiptoo P, Wang W T, Choi I Y, Lee P, Vines C M, Siahaan T J. Suppression of EAE and prevention of blood-brain barrier breakdown after vaccination with novel bifunctional peptide inhibitor. Neuropharmacology. 2012; 62: 1874-1881.
17. Murray J S, Oney S, Page J E, Kratochvil-Stava A, Hu Y, Makagiansar I T, Brown J C, Kobayashi N, Siahaan T J. Suppression of type 1 diabetes in NOD mice by bifunctional peptide inhibitor: modulation of the immunological synapse formation. Chem Biol Drug Des. 2007; 70: 227-236.
18. Badawi A H, Siahaan T J. Immune modulating peptides for the treatment and suppression of multiple sclerosis. Clin Immunol. 2012; 144: 127-138.
19. Buyuktimkin B, Wang Q, Kiptoo P, Stewart J M, Berkland C, Siahaan T J. Vaccine-like controlled-release delivery of an immunomodulating peptide to treat experimental autoimmune encephalomyelitis. Mol Pharm. 2012; 9: 979-985.
20. Kobayashi N, Kiptoo P, Kobayashi H, Ridwan R, Brocke S, Siahaan T J. Prophylactic and therapeutic suppression of experimental autoimmune encephalomyelitis by a novel bifunctional peptide inhibitor. Clin Immunol. 2008; 129: 69-79.
21. Ridwan R, Kiptoo P, Kobayashi N, Weir S, Hughes M, Williams T, Soegianto R, Siahaan T J. Antigen-specific suppression of experimental autoimmune encephalomyelitis by a novel bifunctional peptide inhibitor: structure optimization and pharmacokinetics. J Pharmacol Exp Ther. 2010; 332: 1136-1145.
22. Zhao H, Kiptoo P, Williams T D, Siahaan T J, Topp E M. Immune response to controlled release of immunomodulating peptides in a murine experimental autoimmune encephalomyelitis (EAE) model. J Control Release. 2010; 141: 145-152.
23. Schmidt S. Candidate autoantigens in multiple sclerosis. Multiple sclerosis. 1999; 5: 147-160.
24. Higgins P J, Weiner H L. Suppression of experimental autoimmune encephalomyelitis by oral administration of myelin basic protein and its fragments. J Immunol. 1988; 140: 440-445.
25. Manikwar P, Buyuktimkin B, Kiptoo P, Badawi A H, Galeva N A, Williams T D, Siahaan T J. I-domain-antigen conjugate (IDAC) for delivering antigenic peptides to APC: synthesis, characterization, and in vivo EAE suppression. Bioconjug Chem. 2012; 23: 509-517.
26. Büyüktimkin B, Manikwar P, Kiptoo P K, Badawi A H, Jr. J M S, Siahaan T J. Vaccine-like and Prophylactic Treatments of EAE with Novel I-Domain Antigen Conjugates (IDAC): Targeting Multiple Antigenic Peptides to APC. Mol Pharm. 2012; November.
27. Zimmerman T, Oyarzabal J, Sebastian E S, Majumdar S, Tejo B A, Siahaan T J, Blanco F J. ICAM-1 peptide inhibitors of T-cell adhesion bind to the allosteric site of LFA-1. An NMR characterization. Chem Biol Drug Des. 2007; 70: 347-353.
28. Carson K R, Focosi D, Major E O, Petrini M, Richey E A, West D P, Bennett C L. Monoclonal antibody-associated progressive multifocal leucoencephalopathy in patients treated with rituximab, natalizumab, and efalizumab: a Review from the Research on Adverse Drug Events and Reports (RADAR) Project. Lancet Oncol. 2009; 10: 816-824.
29. Pugashetti R, Koo J. Efalizumab discontinuation: a practical strategy. J Dermatolog Treat. 2009; 20: 132-136.
30. McRae B L, Vanderlugt C L, Dal Canto M C, Miller S D. Functional evidence for epitope spreading in the relapsing pathology of experimental autoimmune encephalomyelitis. J Exp Med. 1995; 182: 75-85.
31. Mehvar R. Modulation of the pharmacokinetics and pharmacodynamics of proteins by polyethylene glycol conjugation. J Pharm Pharm Sci. 2000; 3: 125-136.
32. Caliceti P, Veronese F M. Pharmacokinetic and biodistribution properties of poly(ethylene glycol)-protein conjugates. Adv Drug Deliv Rev. 2003; 55: 1261-1277.
33. Barnes T, Moots R. Targeting nanomedicines in the treatment of rheumatoid arthritis: focus on certolizumab pegol. Int J Nanomedicine. 2007; 2: 3-7.

Example 4

Animal Studies with MOG-PEG-IDAC

The present example describes development of I-domain antigen conjugate (IDAC) molecules derived from the I-domain protein and conjugated with multiple MOG peptides to treat experimental autoimmune encephalomyelitis (EAE) in an animal model using prophylactic method. The I-domain is derived from a binding region of LFA-1, which interacts with the first domain (D1) of ICAM-1[11]. Because the I-domain has multiple lysine residues, several MOG peptides can be conjugated to one molecule of the I-domain. In this study, MOG-PEG-IDAC molecules were synthesized as described above in Example 3. The purified MOG-IDAC and MOG-PEG-IDAC molecules were characterized as described above, and their efficacies were evaluated in the EAE mouse model and compared to negative controls (i.e., PBS, MOG). In prophylactic delivery method, MOG-PEG-IDAC molecules effectively suppressed EAE compared to PBS and MOG.

Materials & Methods
Animals

C57BL/6 mice were purchased from Jackson Laboratory (Bar Harbor, Me.) and subsequently housed under specific pathogen-free conditions at the animal facility at The University of Kansas approved by the Association for Assessment and Accreditation of Laboratory Animal Care (AAALAC). All experimental procedures using live mice were approved by the Institutional Animal Care and Use Committee (IACUC) at The University of Kansas.

Peptide, I-Domain, and IDAC Synthesis

Peptides (MOG peptides and modified I-domain peptides) were synthesized as described in Example 3 above. MOG-PEG-IDAC molecules were also synthesized as described in Example 3.

Induction of EAE and Efficacy Studies

To induce MOG-stimulated EAE in mice, four-to-six week old C57BL/6 female mice were immunized subcutaneously with 200 μg of $MOG_{38-50}$ peptide in a 0.2 ml emulsion consisting of equal volumes of PBS and complete Freund's adjuvant (CFA) containing killed *mycobacterium tuberculosis* strain H37RA at a final concentration of 4 mg/ml (Difco, Detroit, Mich.). The MOG/CFA emulsion was administered to regions above the shoulder and the flanks (total of 4 sites, 50 μl at each injection site). In addition, 400 ng of pertussis toxin was injected intraperitoneally on the day of immunization (day 0) and 2 days post-immunization.

The mice then received subcutaneous injections of MOG-PEG-IDAC (26 nmol/injection) or peptides (100 nmol/injection for PBS and MOG). The prophylactic disease suppression was carried out with subcutaneous injections of IDAC molecules on days 4 and 7, or PBS or MOG molecules on days 4, 7, and 10. Disease progression was evaluated by monitoring the change in weight of the mice and clinical scoring based on the severity of nerve damage ranging from 0 to 5: 0—no clinical symptoms of disease; 1—tail weakness or limp tail; 2—paraparesis (weakness or partial paralysis of one or two hind limbs); 3—paraplegia (complete paralysis of two hind limbs); 4—paraplegia with forelimb weakness or paralysis; 5—moribund (at this point, the affected mice were euthanized).

Statistical Analysis

Statistical differences among the groups in clinical disease scores were determined by calculating the average score for each mouse from day 9 to day 25 by one-way analysis of variance followed by Fisher's least significant difference. Statistical differences in body weight among groups were also analyzed in the same fashion, but from day 1 to day 25. All analyses were performed using StatView (SAS Institute, Cary, N.C.).

Results
Suppression of EAE by IDAC-1 and -3

Figure 31C:
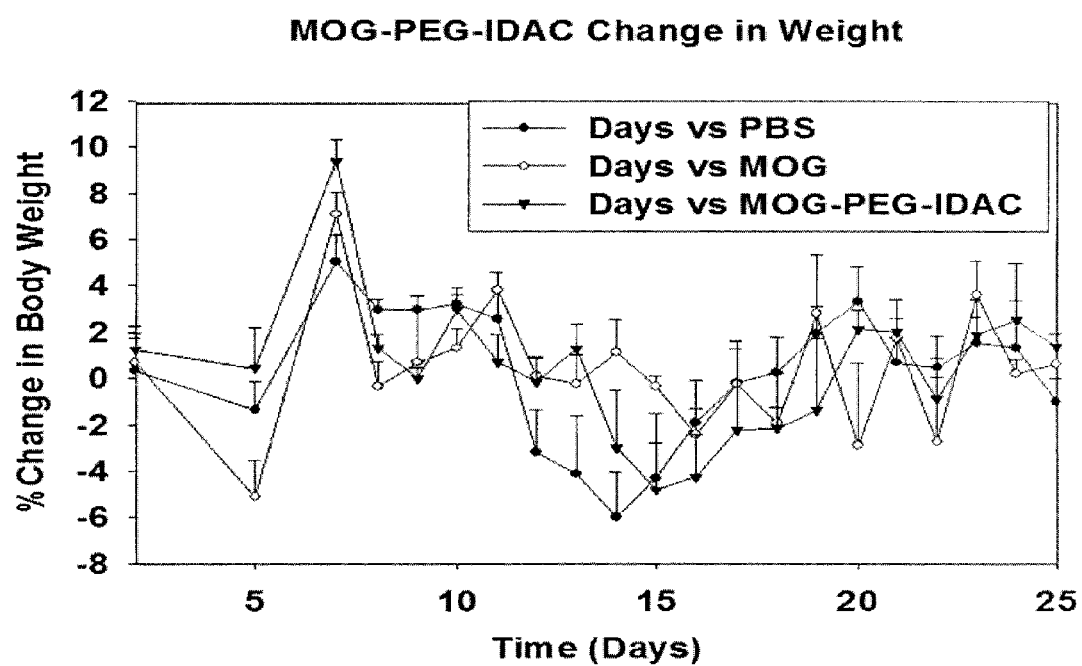

To test whether the MOG-PEG-IDAC molecules have in vivo efficacy, three groups of mice were treated with two injections of the MOG-PEG-IDAC (26 nmol/injection) on days 4 and 7. Control groups were treated with three injection of 100 nmol of PBS or MOG on days 4, 7, and 10. Using the clinical scores (FIG. 31A), MOG-PEG-IDAC delayed the onset of disease and was significantly better at suppressing EAE than PBS or MOG alone (through days 9-25) (n=3, $p<0.05$ for MOG-PEG-IDAC; n=6, $p<0.0001$ for PBS and MOG). There were delays in disease incidence in MOG-PEG-IDAC treated animals (FIG. 31B) (n=3). The body weight change for MOG-PEG-IDAC treated animals (n=3), MOG (n=6) and PBS (n=7) treated animals supported the clinical score data (p=0.003) (FIG. 31C). Thus, the results show that two injections of MOG-PEG-IDAC were more effective than PBS or MOG in suppressing disease results.

Discussion

The present example shows the utility of the I-domain as a carrier protein to deliver antigenic peptides, such as MOG peptides, to suppress EAE. The results of the present example suggest that two injections (26 nmol/injection) of MOG-PEG-IDAC can suppress disease onset and severety. This corroborates the above examples with PLP-IDAC, showing that IDAC conjugated peptides can suppress onset and symptoms of autoimmune disorders in an EAE model.

In conclusion, MOG-PEG-IDAC effectively inhibited the onset and severity of EAE in the mouse model. The conjugation of multiple copies of a single antigenic epitope to a single molecule of I-domain suppresses EAE by shifting the immune response to a regulatory phenotype. Along with the data from Examples 1 and 2 above, these studies demonstrate successful disease suppression with both MOG- and PLP-IDAC molecules. The studies indicate that conjugating multiple immunodominant epitopes, such as MOG, PLP and MBP, to the I-domain will also suppress disease and may inhibit or reduce the epitope spreading phenomenon.

TABLE 4

List of amino acid sequences used in the present disclsoure

| SEQ ID NO | Sequence | Source/description |
|---|---|---|
| 1 | MGNVDLVFLFDGSMSLQPDEFQKILDFMKDVMKK LSNTSYQFAAVQFSTSYKTEFDFSDYVKRKDPDAL LKHVKHMLLLTNTFGAINYVATEVFREELGARPDAT KVLIIITDGEATDSGNIDAAKDIIRYIIGIGKHFQTKES QETLHKFASKPASEFVKILDTFEKLKDLFTELQKKIY | *homo sapiens* I-domain |

TABLE 4-continued

List of amino acid sequences used in the present disclsoure

| SEQ ID NO | Sequence | Source/description |
|---|---|---|
| 2 | HSLGKWLGHPDKFC | Artificial/chemically synthesized signal 1 moiety peptide with amino acids 139-151 of PLP protein modified with a terminal cysteine |
| 3 | GWYRSPFSRVVHL | Source: *homo sapiens* MOG 38-50 |
| 4 | GWYRSPFSRVVHLC | Artificial/chemically synthesized signal 1 moiety peptide with amino acids 38-50 of MOG protein modified with a terminal cysteine |
| 5 | LTGTEKLIETYFSKNYQDYEY | Source: *homo sapiens* PLP 40-60 |
| 6 | LTGTEKLIETYFSKNYQDYEYC | Artificial/chemically synthesized signal 1 moiety peptide with amino acids 40-60 of PLP protein modified with a terminal cysteine |
| 7 | ASQKRPSQR | Source: *homo sapiens* MBP 1-9 |
| 8 | PRHRDTGILDSIGRF | Source: *homo sapiens* MBP30-40 |
| 9 | ENPVVHFFKNIVTPRTP | Source: *homo sapiens* MBP83-99 |
| 10 | ASDYKSAHKGFKGVD | Source: *homo sapiens* MBP131-145 |
| 11 | GFKGVDAQGTLSKIF | Source: *homo sapiens* MBP140-154 |
| 12 | HCLGKWLGHPDKF | Source: *homo sapiens* PLP 139-151 |
| 13 | HSLGKWLGHPDKF | Artificial/chemically synthesized signal 1 moiety peptide with amino acids 139-151 of PLP protein modified with C>S at 2 |
| 14 | HSLGKQLGHPDKF | Artificial/chemically synthesized signal 1 moiety peptide with amino acids 139-151 of PLP protein modified with C>S at 2 and W>Q at 6. |
| 15 | HSLGKLLGRPDKF | Artificial/chemically synthesized signal 1 moiety peptide with amino acids 139-151 of PLP protein modified with C>S at 2, W>Q at 6, and H>R at 9 |
| 16 | HSLGKWDGHPDKF | Artificial/chemically synthesized signal 1 moiety peptide with |

TABLE 4-continued

List of amino acid sequences used in the present disclsoure

| SEQ ID NO | Sequence | Source/description |
|---|---|---|
| | | amino acids 139-151 of PLP protein modified with C>S at 2 and L>D at 7 |
| 17 | EGYTTGAVRQIFGDYKT | Source: homo sapiens PLP 89-106 |
| 18 | CFFGVALFCGCGHEALTGTEKLIETYFSKNYQ | Source: homo sapiens PLP 25-26 |
| 19 | GKVCGSNLLSICKTAEFQMTFHLFIAAFVGAA | Source: homo sapiens PLP 217-248 |
| 20 | FMIAATYNFAVLKLMGRGTK | Source: homo sapiens PLP 257-276 |
| 21 | FYTTGAVRQIFGDYKTTICG | Source: homo sapiens PLP 91-110 |
| 22 | TEKLIETYFSKNYQDYEYLINV | Source: homo sapiens PLP 43-64 |
| 23 | KTTICGKGLSATVT | Source: homo sapiens PLP 104-117 |
| 24 | DYEYLINVIHAFQYV | Source: homo sapiens PLP 56-70 |
| 25 | NTWTTCQSIAFPSK | Source: homo sapiens PLP 178-191 |
| 26 | PGYPIRALVGDEAE | Source: homo sapiens MOG 8-21 |
| 27 | MEVGWYRSPFSRVVHLYRNGK | Source: rattus norvegicus/Mus musculus MOG 35-55 |
| 28 | TCFFRDHSYQEE | Source: homo sapiens MOG 97-108 |
| 29 | XaaGlyXaaGlyXaa (AcpGlyAcpGlyAcp) | Artificial/Chemically Synthesized linker sequence, where Xaa = Acp |
| 30 | ITDGEATDSG | Source: homo sapiens BPI |
| 31 | PRGGSVLVTGC | Source: homo sapiens CIBR1 |

The invention claimed is:

1. A compound comprising:
a modified I-domain peptide comprising SEQ ID NO: 1 that is capable of binding a D1 domain of ICAM-1, the modified I-domain peptide having two or more modified lysine residues; and
two or more signal 1 moieities conjugated to the modified lysine residues of the I-domain peptide, wherein the two or more signal 1 moieities are the same or different and wherein the two or more signal 1 moieties are chosen from epitopes of proteolipid protein (PLP), myelin basic protein (MBP), myelin oligodendrocyte glycoprotein (MOG), and a combination thereof, wherein the epitopes of PLP, MBP, and MOG are chosen from peptide sequences selected from the group consisting of: SEQ ID NOs: 2-28, and wherein any signal 1 moiety comprising an epitope of MOG also comprises a poly-ethylene glycol (PEG) spacer.

2. The compound of claim 1, wherein the signal 1 moieities are conjugated to the modified lysine residues of the I-domain peptide via linkers.

3. The compound of claim 2, wherein the linker comprises a maleimido group capable of conjugating a cysteine residue of the signal 1 moiety to a lysine residue of the I-domain peptide.

4. The compound of claim 1, wherein if the peptide sequence of the signal 1 moieties does not include a terminal cysteine residue, the signal 1 moiety is further modified to include a terminal cysteine residue.

5. The compound of claim 1, wherein at least one signal 1 moiety comprises amino acids 139-151 of PLP having a terminal cysteine (SEQ ID No. 2).

6. The compound of claim 1, wherein the modified I-domain has about two to 20 modified lysine residues.

7. The compound of claim 3, wherein the linker comprises one or more spacers to extend the length of the linker.

8. The compound of claim 7, wherein the spacer is chosen from poly-ethylene glycol (PEG) and poly-Gly.

9. The compound of claim 1, wherein the modified lysine residues of the I-domain peptide comprise mutation of the lysine residue to a cysteine residue, wherein a thiol group of the cysteine residue is capable of being conjugated to a maleimide residue of a signal 1 moiety.

10. The compound of claim 3, wherein the maleimido group linker is conjugated to a cysteine residue of the signal 1 moiety and wherein the cysteine residue is chosen from a C-terminal cysteine residue, an N-terminal cysteine residue, or both.

11. A compound comprising:

a modified I-domain peptide comprising SEQ ID NO: 1, wherein two or more lysine residues are modified with a maleimido group, and two or more signal 1 moieties conjugated to the modified lysine residues of the I-domain peptides, wherein the signal 1 moieties are chosen from epitopes of proteolipid protein (PLP), myelin basic protein (MBP), myelin oligodendrocyte glycoprotein (MOG) modified with poly-ethylene glycol (PEG), and combinations thereof, wherein the epitopes of PLP, MBP, and MOG are chosen from peptide sequences selected from the group consisting of: SEQ ID NOs: 2-28, and further comprising a terminal cysteine residue.

12. The compound of claim 11, wherein at least two signal 1 moieties are different.

13. The compound of claim 1, wherein the epitopes of PLP, MBP, and MOG are chosen from peptide sequences selected from the group consisting of: SEQ ID NO: 2, SEQ ID NO: 4, and SEQ ID NO: 7, wherein SEQ ID NO: 7 is further modified to comprise a terminal cysteine residue.

* * * * *

UNITED STATES PATENT AND TRADEMARK OFFICE
CERTIFICATE OF CORRECTION

PATENT NO. : 9,573,983 B2  
APPLICATION NO. : 13/733991  
DATED : February 21, 2017  
INVENTOR(S) : Teruna J. Siahaan et al.

Page 1 of 1

It is certified that error appears in the above-identified patent and that said Letters Patent is hereby corrected as shown below:

STATEMENT REGARDING FEDERALLY SPONSORED RESEARCH OR DEVELOPMENT should read:
This invention was made with government support under grant number R01 AI063002 awarded by the National Institutes of Health. The government has certain rights in the invention.

Signed and Sealed this
Eighth Day of May, 2018

Andrei Iancu
*Director of the United States Patent and Trademark Office*

SEQUENCE LISTING

<160> NUMBER OF SEQ ID NOS: 31

<210> SEQ ID NO 1
<211> LENGTH: 181
<212> TYPE: PRT
<213> ORGANISM: Homo sapiens

<400> SEQUENCE: 1

Met Gly Asn Val Asp Leu Val Phe Leu Phe Asp Gly Ser Met Ser Leu
1               5                   10                  15

Gln Pro Asp Glu Phe Gln Lys Ile Leu Asp Phe Met Lys Asp Val Met
            20                  25                  30

```
Lys Lys Leu Ser Asn Thr Ser Tyr Gln Phe Ala Ala Val Gln Phe Ser
        35                  40                  45

Thr Ser Tyr Lys Thr Glu Phe Asp Phe Ser Asp Tyr Val Lys Arg Lys
    50                  55                  60

Asp Pro Asp Ala Leu Leu Lys His Val Lys His Met Leu Leu Leu Thr
65                  70                  75                  80

Asn Thr Phe Gly Ala Ile Asn Tyr Val Ala Thr Glu Val Phe Arg Glu
                85                  90                  95

Glu Leu Gly Ala Arg Pro Asp Ala Thr Lys Val Leu Ile Ile Ile Thr
                100                 105                 110

Asp Gly Glu Ala Thr Asp Ser Gly Asn Ile Asp Ala Ala Lys Asp Ile
                115                 120                 125

Ile Arg Tyr Ile Ile Gly Ile Gly Lys His Phe Gln Thr Lys Glu Ser
            130                 135                 140

Gln Glu Thr Leu His Lys Phe Ala Ser Lys Pro Ala Ser Glu Phe Val
145                 150                 155                 160

Lys Ile Leu Asp Thr Phe Glu Lys Leu Lys Asp Leu Phe Thr Glu Leu
                165                 170                 175

Gln Lys Lys Ile Tyr
            180

<210> SEQ ID NO 2
<211> LENGTH: 14
<212> TYPE: PRT
<213> ORGANISM: Artificial Sequence
<220> FEATURE:
<223> OTHER INFORMATION: Chemically synthesized signal 1 moiety peptide
      with amino acids 139-151 of PLP protein modified with a terminal
      cysteine

<400> SEQUENCE: 2

His Ser Leu Gly Lys Trp Leu Gly His Pro Asp Lys Phe Cys
1               5                   10

<210> SEQ ID NO 3
<211> LENGTH: 13
<212> TYPE: PRT
<213> ORGANISM: Homo sapiens

<400> SEQUENCE: 3

Gly Trp Tyr Arg Ser Pro Phe Ser Arg Val Val His Leu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Chemically synthesized signal 1 moiety peptide
      with amino acids 38-50 of MOG protein modified with a terminal
      cysteine

<400> SEQUENCE: 4

Gly Trp Tyr Arg Ser Pro Phe Ser Arg Val Val His Leu Cys
1               5                   10

<210> SEQ ID NO 5
<211> LENGTH: 21
<212> TYPE: PRT
<213> ORGANISM: Homo sapiens

<400> SEQUENCE: 5
```

```
Leu Thr Gly Thr Glu Lys Leu Ile Glu Thr Tyr Phe Ser Lys Asn Tyr
1               5                   10                  15

Gln Asp Tyr Glu Tyr
            20
```

<210> SEQ ID NO 6
<211> LENGTH: 22
<212> TYPE: PRT
<213> ORGANISM: Artificial Sequence
<220> FEATURE:
<223> OTHER INFORMATION: Chemically synthesized signal 1 moiety peptide
      with amino acids 40-60 of PLP protein modified with a terminal
      cysteine

<400> SEQUENCE: 6

```
Leu Thr Gly Thr Glu Lys Leu Ile Glu Thr Tyr Phe Ser Lys Asn Tyr
1               5                   10                  15

Gln Asp Tyr Glu Tyr Cys
            20
```

<210> SEQ ID NO 7
<211> LENGTH: 9
<212> TYPE: PRT
<213> ORGANISM: Homo sapiens

<400> SEQUENCE: 7

```
Ala Ser Gln Lys Arg Pro Ser Gln Arg
1               5
```

<210> SEQ ID NO 8
<211> LENGTH: 15
<212> TYPE: PRT
<213> ORGANISM: Homo sapiens

<400> SEQUENCE: 8

```
Pro Arg His Arg Asp Thr Gly Ile Leu Asp Ser Ile Gly Arg Phe
1               5                   10                  15
```

<210> SEQ ID NO 9
<211> LENGTH: 17
<212> TYPE: PRT
<213> ORGANISM: Homo sapiens

<400> SEQUENCE: 9

```
Glu Asn Pro Val Val His Phe Phe Lys Asn Ile Val Thr Pro Arg Thr
1               5                   10                  15

Pro
```

<210> SEQ ID NO 10
<211> LENGTH: 15
<212> TYPE: PRT
<213> ORGANISM: Homo sapiens

<400> SEQUENCE: 10

```
Ala Ser Asp Tyr Lys Ser Ala His Lys Gly Phe Lys Gly Val Asp
1               5                   10                  15
```

<210> SEQ ID NO 11
<211> LENGTH: 15
<212> TYPE: PRT
<213> ORGANISM: Homo sapiens

<400> SEQUENCE: 11

Gly Phe Lys Gly Val Asp Ala Gln Gly Thr Leu Ser Lys Ile Phe
1               5                   10                  15

<210> SEQ ID NO 12
<211> LENGTH: 13
<212> TYPE: PRT
<213> ORGANISM: Homo sapiens

<400> SEQUENCE: 12

His Cys Leu Gly Lys Trp Leu Gly His Pro Asp Lys Phe
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Chemically synthesized signal 1 moiety peptide
      with amino acids 139-151 of PLP protein modified with C>S at 2

<400> SEQUENCE: 13

His Ser Leu Gly Lys Trp Leu Gly His Pro Asp Lys Phe
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Chemically synthesized signal 1 moiety peptide
      with amino acids 139-151 of PLP protein modified with C>S at 2 and
      W>Q at 6.

<400> SEQUENCE: 14

His Ser Leu Gly Lys Gln Leu Gly His Pro Asp Lys Phe
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Chemically synthesized signal 1 moiety peptide
      with amino acids 139-151 of PLP protein modified with C>S at 2,
      W>Q at 6, and H>R at 9

<400> SEQUENCE: 15

His Ser Leu Gly Lys Leu Leu Gly Arg Pro Asp Lys Phe
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Chemically synthesized signal 1 moiety peptide
      with amino acids 139-151 of PLP protein modified with C>S at 2 and
      L>D at 7

<400> SEQUENCE: 16

His Ser Leu Gly Lys Trp Asp Gly His Pro Asp Lys Phe
1               5                   10

<210> SEQ ID NO 17
<211> LENGTH: 17
<212> TYPE: PRT
<213> ORGANISM: Homo sapiens

```
<400> SEQUENCE: 17

Glu Gly Tyr Thr Thr Gly Ala Val Arg Gln Ile Phe Gly Asp Tyr Lys
1               5                   10                  15

Thr

<210> SEQ ID NO 18
<211> LENGTH: 32
<212> TYPE: PRT
<213> ORGANISM: Homo sapiens

<400> SEQUENCE: 18

Cys Phe Phe Gly Val Ala Leu Phe Cys Gly Cys Gly His Glu Ala Leu
1               5                   10                  15

Thr Gly Thr Glu Lys Leu Ile Glu Thr Tyr Phe Ser Lys Asn Tyr Gln
            20                  25                  30

<210> SEQ ID NO 19
<211> LENGTH: 32
<212> TYPE: PRT
<213> ORGANISM: Homo sapiens

<400> SEQUENCE: 19

Gly Lys Val Cys Gly Ser Asn Leu Leu Ser Ile Cys Lys Thr Ala Glu
1               5                   10                  15

Phe Gln Met Thr Phe His Leu Phe Ile Ala Ala Phe Val Gly Ala Ala
            20                  25                  30

<210> SEQ ID NO 20
<211> LENGTH: 20
<212> TYPE: PRT
<213> ORGANISM: Homo sapiens

<400> SEQUENCE: 20

Phe Met Ile Ala Ala Thr Tyr Asn Phe Ala Val Leu Lys Leu Met Gly
1               5                   10                  15

Arg Gly Thr Lys
            20

<210> SEQ ID NO 21
<211> LENGTH: 20
<212> TYPE: PRT
<213> ORGANISM: Homo sapiens

<400> SEQUENCE: 21

Phe Tyr Thr Thr Gly Ala Val Arg Gln Ile Phe Gly Asp Tyr Lys Thr
1               5                   10                  15

Thr Ile Cys Gly
            20

<210> SEQ ID NO 22
<211> LENGTH: 22
<212> TYPE: PRT
<213> ORGANISM: Homo sapiens

<400> SEQUENCE: 22

Thr Glu Lys Leu Ile Glu Thr Tyr Phe Ser Lys Asn Tyr Gln Asp Tyr
1               5                   10                  15

Glu Tyr Leu Ile Asn Val
            20

<210> SEQ ID NO 23
```

```
<211> LENGTH: 14
<212> TYPE: PRT
<213> ORGANISM: Homo sapiens

<400> SEQUENCE: 23

Lys Thr Thr Ile Cys Gly Lys Gly Leu Ser Ala Thr Val Thr
1               5                   10

<210> SEQ ID NO 24
<211> LENGTH: 15
<212> TYPE: PRT
<213> ORGANISM: Homo sapiens

<400> SEQUENCE: 24

Asp Tyr Glu Tyr Leu Ile Asn Val Ile His Ala Phe Gln Tyr Val
1               5                   10                  15

<210> SEQ ID NO 25
<211> LENGTH: 14
<212> TYPE: PRT
<213> ORGANISM: Homo sapiens

<400> SEQUENCE: 25

Asn Thr Trp Thr Thr Cys Gln Ser Ile Ala Phe Pro Ser Lys
1               5                   10

<210> SEQ ID NO 26
<211> LENGTH: 14
<212> TYPE: PRT
<213> ORGANISM: Homo sapiens

<400> SEQUENCE: 26

Pro Gly Tyr Pro Ile Arg Ala Leu Val Gly Asp Glu Ala Glu
1               5                   10

<210> SEQ ID NO 27
<211> LENGTH: 21
<212> TYPE: PRT
<213> ORGANISM: Rattus norvegicus

<400> SEQUENCE: 27

Met Glu Val Gly Trp Tyr Arg Ser Pro Phe Ser Arg Val Val His Leu
1               5                   10                  15

Tyr Arg Asn Gly Lys
            20

<210> SEQ ID NO 28
<211> LENGTH: 12
<212> TYPE: PRT
<213> ORGANISM: Homo sapiens

<400> SEQUENCE: 28

Thr Cys Phe Phe Arg Asp His Ser Tyr Gln Glu Glu
1               5                   10

<210> SEQ ID NO 29
<211> LENGTH: 5
<212> TYPE: PRT
<213> ORGANISM: Artificial Sequence
<220> FEATURE:
<223> OTHER INFORMATION: Chemically Synthesized linker sequence
<220> FEATURE:
<221> NAME/KEY: Xaa
<222> LOCATION: (1)..(1)
<223> OTHER INFORMATION: Xaa=Acp
<220> FEATURE:
```

```
<221> NAME/KEY: Xaa
<222> LOCATION: (3)..(3)
<223> OTHER INFORMATION: Xaa=Acp
<220> FEATURE:
<221> NAME/KEY: Xaa
<222> LOCATION: (5)..(5)
<223> OTHER INFORMATION: Xaa=Acp

<400> SEQUENCE: 29

Xaa Gly Xaa Gly Xaa
1               5

<210> SEQ ID NO 30
<211> LENGTH: 10
<212> TYPE: PRT
<213> ORGANISM: Homo sapiens

<400> SEQUENCE: 30

Ile Thr Asp Gly Glu Ala Thr Asp Ser Gly
1               5                   10

<210> SEQ ID NO 31
<211> LENGTH: 11
<212> TYPE: PRT
<213> ORGANISM: Homo sapiens

<400> SEQUENCE: 31

Pro Arg Gly Gly Ser Val Leu Val Thr Gly Cys
1               5                   10
```